(12) United States Patent
Garbaccio et al.

(10) Patent No.: US 10,550,190 B2
(45) Date of Patent: Feb. 4, 2020

(54) PHOSPHATE BASED LINKERS FOR INTRACELLULAR DELIVERY OF DRUG CONJUGATES

(71) Applicants: Merck Sharp & Dohme Corp., Rahway, NJ (US); Ambrx, Inc., La Jolla, CA (US)

(72) Inventors: Robert M. Garbaccio, Lansdale, PA (US); Jeffrey Kern, Gilbertsville, PA (US); Philip E. Brandish, Needham, MA (US); Sanjiv Shah, Wakefield, MA (US); Linda Liang, Mountain View, CA (US); Ying Sun, San Diego, CA (US); Jianing Wang, San Diego, CA (US); Nick Knudsen, Escondido, CA (US); Andrew Beck, San Diego, CA (US); Anthony Manibusan, San Diego, CA (US); Dennis Gately, San Diego, CA (US)

(73) Assignees: Merck Sharp & Dohme Corp., Rahway, NJ (US); Ambrx, Inc., La Jolla, CA (US)

( * ) Notice: Subject to any disclaimer, the term of this patent is extended or adjusted under 35 U.S.C. 154(b) by 348 days.

(21) Appl. No.: 15/301,564

(22) PCT Filed: Mar. 30, 2015

(86) PCT No.: PCT/US2015/023247
§ 371 (c)(1),
(2) Date: Oct. 3, 2016

(87) PCT Pub. No.: WO2015/153401
PCT Pub. Date: Oct. 8, 2015

(65) Prior Publication Data
US 2017/0182181 A1    Jun. 29, 2017

Related U.S. Application Data

(60) Provisional application No. 62/112,222, filed on Feb. 5, 2015, provisional application No. 61/975,407, filed on Apr. 4, 2014.

(51) Int. Cl.
| | |
|---|---|
| *C07J 71/00* | (2006.01) |
| *A61K 47/54* | (2017.01) |
| *C07F 9/09* | (2006.01) |
| *C07K 16/28* | (2006.01) |

(52) U.S. Cl.
CPC .............................. *C07K 16/2866* (2013.01)

(58) Field of Classification Search
None
See application file for complete search history.

(56) References Cited

U.S. PATENT DOCUMENTS

| | | | |
|---|---|---|---|
| 5,094,848 | A | 3/1992 | Brixner |
| 5,621,002 | A | 4/1997 | Bosslet et al. |
| 6,214,345 | B1 | 4/2001 | Firestone et al. |
| 6,218,519 | B1 | 4/2001 | Kenten et al. |
| 6,268,488 | B1 | 7/2001 | Barbas, III |
| 6,677,435 | B2 | 1/2004 | Barbas, III et al. |
| 6,759,509 | B1 | 7/2004 | Kotani et al. |
| 6,835,807 | B1 | 12/2004 | Susaki et al. |
| 2002/0102590 | A1 | 8/2002 | Taing et al. |
| 2003/0096743 | A1 | 5/2003 | Senter et al. |
| 2003/0130189 | A1 | 7/2003 | Senter et al. |
| 2004/0018194 | A1 | 1/2004 | Francisco et al. |
| 2004/0052793 | A1 | 3/2004 | Carter et al. |
| 2004/0121940 | A1 | 6/2004 | De Groot et al. |
| 2006/0122143 | A1 | 6/2006 | Boyer et al. |
| 2007/0048773 | A1 | 3/2007 | Lee et al. |
| 2010/0249072 | A1 | 9/2010 | Borch et al. |
| 2012/0058473 | A1 | 3/2012 | Yue et al. |

FOREIGN PATENT DOCUMENTS

| | | |
|---|---|---|
| WO | 199813059 | 4/1998 |
| WO | 2004032828 | 4/2004 |

OTHER PUBLICATIONS

Pub Chem Compound Summary, CID21125146, 2007, pp. 1 and 2.
Alley et al., Bioconjugate Chem. vol. 19, 2008, pp. 759-765.
Austin et al., Proc. Natl. Acad. Sci. USA, vol. 102, 2005, pp. 17987-17992.
Blather et al., Biochem. vol. 24, 1985, pp. 1517-1524.
Carl et al., J. Med. Chem. vol. 24, 1981, pp. 479-480.
Chakravarty et al., J. Med. Chem. vol. 26, 1983, pp. 638-644.
Chari, Adv. Drug Delivery Rev. vol. 31, 1998, pp. 89-104.
De Groot, et al., J. Med. Chem. vol. 42, 1999, pp. 5277-5283.
De Groot, et al., Molecular Cancer Therapeutics vol. 1, 2002, pp. 901-911.
De Groot, et al., Journal of Organic Chemistry vol. 66, 2001, pp. 8815-8830.
Doronina et al., Bioconj. Chem. vol. 17, 2006, pp. 114-124.
Erickson et al., Cancer Res. vol. 66, 2006, pp. 4426-4433.
Hamann et al., Bioconj. Chem. vol. 16, 2005, pp. 346-353.
Hashimoto et al., Biochem. Biophys. Res. Commun. vol. 283, 2001, pp. 334-339.

(Continued)

*Primary Examiner* — Mark Halvorson
*Assistant Examiner* — Kauser M Akhoon
(74) *Attorney, Agent, or Firm* — David Van Goor; Anna Cocuzzo

(57) ABSTRACT

Phosphate-based linkers with tunable stability for intracellular delivery of drug conjugates are described. The phosphate-based linkers comprise a monophosphate, diphosphate, triphosphate, or tetraphosphate group (phosphate group) and a linker arm comprising a tuning element and optionally a spacer. A payload is covalently linked to the phosphate group at the distal end of the linker arm and the functional group at the proximal end of the linker arm is covalently linked to a cell-specific targeting ligand such as an antibody. These phosphate-based linkers have a differentiated and tunable stability in blood vs. an intracellular environment (e.g. lysosomal compartment).

4 Claims, 9 Drawing Sheets

Specification includes a Sequence Listing.

(56) References Cited

OTHER PUBLICATIONS

King et al., J. Med. Chem. vol. 45, 2002, pp. 4336-4343.
Lewis et al., Cancer Res. vol. 68, 2008, pp. 9280-9290.
Sinha et al., Prostate vol. 49, 2001, pp. 172-184.
Widdeson et al., J. Med. Chem. vol. 49, 2006, pp. 4392-4408.
Hong et al., Nucleoside conjugates as potential antitumor agents. 2. Synthesis and Biological Activity of 1-.beta.-D-arabinofuranosyl cytosine conjugates of prednisolone and prednisone, Journal of Medicinal Chemistry, vol. 22, No. 11, 1979, pp. 1428-1432.

SEQUENCE LISTING

<160> NUMBER OF SEQ ID NOS: 4

<210> SEQ ID NO 1
<211> LENGTH: 447
<212> TYPE: PRT

```
<213> ORGANISM: artificial sequence
<220> FEATURE:
<223> OTHER INFORMATION: Anti-CD70 2H5 IgG1
<220> FEATURE:
<221> NAME/KEY: MOD_RES
<222> LOCATION: (119)..(119)
<223> OTHER INFORMATION: Xaa is para-azido-phenylalanine (pAF)

<400> SEQUENCE: 1
```

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
            100                 105                 110

Leu Val Thr Val Ser Ser Xaa Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370             375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Anti-CD70 Kappa Light chain

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 438
<212> TYPE: PRT
<213> ORGANISM: artificial Sequence
<220> FEATURE:
<223> OTHER INFORMATION: Anti-murine CD25 muIgG1 D265A
<220> FEATURE:
<221> NAME/KEY: MOD_RES
<222> LOCATION: (115)..(115)
<223> OTHER INFORMATION: Xaa is para-azido-phenylalanine (pAF)

```
<400> SEQUENCE: 3

Gln Val Lys Leu Leu Gln Ser Gly Ala Ala Leu Val Lys Pro Gly Ala
1               5                   10                  15

Ser Val Lys Met Ser Cys Lys Ala Ser Gly Tyr Ser Phe Pro Asp Ser
            20                  25                  30

Trp Val Thr Trp Val Lys Gln Ser His Gly Lys Ser Leu Glu Trp Ile
        35                  40                  45

Gly Asp Ile Phe Pro Asn Ser Gly Ala Thr Asn Phe Asn Glu Lys Phe
    50                  55                  60

Lys Gly Lys Ala Thr Leu Thr Val Asp Lys Ser Thr Ser Thr Ala Tyr
65                  70                  75                  80

Met Glu Leu Ser Arg Leu Thr Ser Glu Asp Ser Ala Ile Tyr Tyr Cys
                85                  90                  95

Thr Arg Leu Asp Tyr Gly Tyr Trp Gly Gln Gly Val Met Val Thr Val
            100                 105                 110

Ser Ser Xaa Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
    210                 215                 220

Val Pro Glu Val Ser Ser Val Phe Ile Phe Pro Pro Lys Pro Lys Asp
225                 230                 235                 240

Val Leu Thr Ile Thr Leu Thr Pro Lys Val Thr Cys Val Val Val Ala
                245                 250                 255

Ile Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe Asn
        275                 280                 285

Ser Thr Phe Arg Ser Val Ser Glu Leu Pro Ile Met His Gln Asp Trp
    290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Lys Glu Gln Met Ala Lys Asp
            340                 345                 350

Lys Val Ser Leu Thr Cys Met Ile Thr Asp Phe Phe Pro Glu Asp Ile
        355                 360                 365
```

```
Thr Val Glu Trp Gln Trp Asn Gly Gln Pro Ala Glu Asn Tyr Lys Asn
    370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
            420                 425                 430

Ser His Ser Pro Gly Lys
        435

<210> SEQ ID NO 4
<211> LENGTH: 219
<212> TYPE: PRT
<213> ORGANISM: Artificial Sequence
<220> FEATURE:
<223> OTHER INFORMATION: Anti-murine CD25 muKappa

<400> SEQUENCE: 4

Asp Val Val Leu Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Asn Gly Asn Thr Tyr Leu Asn Trp Leu Leu Gln Arg Pro Gly Gln Pro
        35                  40                  45

Pro Gln Leu Leu Ile Tyr Leu Ala Ser Arg Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Val Gln Ser
                85                  90                  95

Ser His Phe Pro Asn Thr Phe Gly Val Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

PHOSPHATE BASED LINKERS FOR INTRACELLULAR DELIVERY OF DRUG CONJUGATES

CROSS REFERENCE TO RELATED APPLICATIONS

This application is the National Stage of International Application No. PCT/US2015/023247 filed on Mar. 30, 2015, which claims the benefit under 35 U.S.C. 119(e) of U.S. Provisional Application Nos. 62/112,222, filed Feb. 5, 2015, and 61/975,407, filed Apr. 4, 2014, both which are herein incorporated by reference in their entirety.

REFERENCE TO SEQUENCE LISTING SUBMITTED ELECTRONICALLY

The sequence listing of the present application is submitted electronically via EFS-Web as an ASCII formatted sequence listing with a file name "23596_US_PCT_SE-QLIST.txt", creation date of Sep. 15, 2016, and a size of 13 KB. This sequence listing submitted via EFS-Web is part of the specification and is herein incorporated by reference in its entirety.

BACKGROUND OF THE INVENTION (1) Field of the Invention

The present invention relates to phosphate-based linkers with tunable stability for intracellular delivery of drug conjugates. The phosphate-based linkers comprise a monophosphate, diphosphate, triphosphate, or tetraphosphate group (phosphate group) and a linker arm comprising a tuning element and optionally a spacer. A payload is covalently linked to the phosphate group at the distal end of the linker arm and the functional group at the proximal end of the linker arm is covalently linked to a cell-specific targeting ligand such as an antibody. These phosphate-based linkers have a differentiated and tunable stability in blood vs. an intracellular environment (e.g. lysosomal compartment). Thus, conjugates that comprise these phosphate-based linkers are stable in circulation (plasma/blood) but reactive or cleavable in intracellular compartments (lysosome) making them useful for intracellular delivery of drug conjugates, the rate being dependent on the structure of the tuning element.

(2) Description of Related Art

Antibody drug conjugates (ADC) are targeted chemotherapeutic molecules combining the ideal properties of both antibodies and cytotoxic drugs by targeting potent cytotoxic drugs to the antigen-expressing tumor cells, internalizing the ADC, and releasing the drug from the ADC, thereby enhancing the drug's anti-tumor activity. This strategy has met limited success in part because many cytotoxic drugs tend to be inactive or less active when conjugated to large antibodies or protein receptor ligands. Promising advancements with immunoconjugates has seen cytotoxic drugs linked to antibodies through a linker that is cleaved at the tumor site or inside tumor cells.

The successful ADC development for a given target antigen depends on optimization of antibody selection, linker design and stability, drug potency and mode of drug and linker conjugation to the antibody. Linker properties of pH and redox sensitivities and protease susceptibility influence circulatory stability and release of the drug moiety. The intracellular cleavage of disulfide containing linkers of an ADC is limited by the oxidizing potential of endosomes and lysosomes and are probably not released by reductive cleavage within the endocytic pathway (Austin et al., Proc. Natl. Acad. Sci. USA 102: 17987-17992 (2005)). Reductive cleavage may occur at the cell membrane and impart a bystander killing effect of tumor and susceptible normal cells by free drug. Inappropriate release of drug likely contributes to toxicity. Once internalized, ADC efficacy is dependent on proteolytic cleavage for drug activity. Linker stability plays an important role in both the efficacy and toxicity of ADC (Alley et al., Bioconjugate Chem. 19:759-765 (2008)). Stable linkers such as mcc are more efficacious and safer than unstable, disulfide linkers, widening the therapeutic window. However, while mcc linkers are more stable than disulfides, they can only be used for drugs that can tolerate residual linker on it and still be potent. Thus, self-immolative linkers are needed for drugs that do not have this flexible structure activity relationship (SAR).

A chemical solution to targeted delivery of cytotoxic or cytostatic drugs conjugated to cell-specific ligands is the "self-immolative linker", PABC or PAB (para-aminobenzyloxycarbonyl) linker, attaching the drug moiety to the ligand in the conjugate (Carl et al., J. Med. Chem. 24: 479-480 (1981); Chakravarty et al., J. Med. Chem. 26: 638-644 (1983)). The PAB linker unit is also referred to as an electronic cascade spacer. The amide bond linking the carboxy terminus of a peptide unit and the para-aminobenzyl of PAB may be a substrate and cleavable by certain proteases. The aromatic amine becomes electron-donating and initiates an electronic cascade that leads to the expulsion of the leaving group, which releases the free drug after elimination of carbon dioxide (de Groot, et al. Journal of Organic Chemistry 66: 8815-8830 (2001)). Cathepsin B is a ubiquitous cysteine protease with increasing activity within low pH environments (i.e. lysosomes). It is an intracellular enzyme, except in pathological conditions, such as metastatic tumors (Sinha et al., Prostate 49: 172-184 (2001)) or rheumatoid arthritis (Hashimoto et al., Biochem. Biophys. Res. Commun. 283: 334-339 (2001)). Therefore, conjugates produced with cathepsin B-cleavable linkers are likely to be stable in circulation. Upon cleavage of a peptide bond adjacent to the PABC, i.e. by an intracellular enzyme, the drug is released from the ligand whereby no remaining portion of the linker is bound (de Groot et al., Molecular Cancer Therapeutics 1: 901-911 (2002); de Groot et al., J. Med. Chem. 42: 5277-5283 (1999)).

Linkers containing the para-aminobenzyloxycarbonyl (PAB or PABC) unit, in conjunction with a peptide unit, have been developed with a "self-immolating" or "self-immolative" mechanism of 1,6 elimination and fragmentation under enzymatic, hydrolytic, or other metabolic conditions to release a drug moiety from a targeting ligand, such as an antibody (U.S. Pat. Nos. 6,214,345; 6,677,435 5,621, 002; 6,218,519; 6,835,807; 6,268,488; and 6,759,509; US Pat. Pub. Nos. 20030130189; 20030096743; 20040052793; 20040018194; 20040052793; and 20040121940; PCT Pub. Nos. WO 98/13059 and WO2004/032828).

Limitations of the PAB type self-immolating linkers are the propensity to cause poor solubility and aggregation of the conjugates. In addition, some PAB-containing conjugates may not be suitable substrates for certain cleaving enzymes or cleave too slowly to achieve efficacy. While the PAB/PABC linkers have been exemplified for amine-terminus payloads that form stable carbamate bonds, for payloads that do not contain a linkable amine, the carbonate that is formed may not be stable and so there is a need for self-immolative linkers that can handle payloads with an oxygen terminus, for example, dexamethasone.

In light of the above, there is a need for linkers for constructing drug-ligand conjugates with improved therapeutic efficacy.

BRIEF SUMMARY OF THE INVENTION

The present invention provides phosphate-based linkers with tunable stability for intracellular delivery of drug conjugates. The phosphate-based linkers comprise a monophosphate, diphosphate, triphosphate, or tetraphosphate group (phosphate group) covalently linked to the distal end of a linker arm comprising from the distal to the proximal direction a tuning element, optionally a spacer element, and a reactive functional group. The phosphate group of the phosphate-based linker is capable of being conjugated to a payload and the reactive functional group is capable of being conjugated to a cell-specific targeting ligand such as an antibody. The general structure of the phosphate-based linkers is:

Phosphate group-Tuning element-Optional spacer element-Functional reactive group A phosphate-based linker conjugated to a payload has the general structure:

Payload-Phosphate group-Tuning element-Optional spacer element-Functional reactive group and when conjugated to a targeting ligand has the general structure Payload-Phosphate group-Tuning element-Optional spacer element-Targeting ligand These phosphate-based linkers have a differentiated and tunable stability in blood vs. an intracellular environment (e.g. lysosomal compartment). The inventors have discovered that the rate at which the phosphate group is cleaved in the intracellular environment to release the payload in its native or active form may be affected by the structure of the tuning element with further effects mediated by substitutions of the phosphate group as well as whether the phosphate group is a monophosphate, diphosphate, triphosphate, or tetraphosphate. The inventors further discovered that these phosphate-based linkers provide the ability to construct conjugates such as antibody-drug conjugates in which the propensity of the conjugate to form aggregates is reduced compared to conjugates in which the same payload is conjugated to the antibody or targeting ligand using a linker that is not a phosphate-based linker as disclosed herein.

In particular embodiments, the phosphate-based linker is a compound that has the following formula (I)

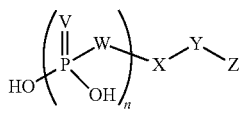

wherein V is selected from O and S; W is selected from O, N, and CH$_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is optional but when present it is selected from a covalent bond or a bivalent, straight or branched, saturated or unsaturated, optionally substituted C1-30 hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, methyl ketone, azide, hydrazine, pentafluorophenyl, haloacetamide, maleimide, hydroxylamine, strained cycloalkyne, heterocycloalkyne, alkyne, diene, azadiene, and heterocyclic azadiene, wherein halo is iodine (I), bromine (Br), fluorine (F), or chlorine (Cl) and hetero is N, O, or S; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4. In particular embodiments, when Y is a covalent bond, X is not a covalent bond.

In particular aspect, the reactive group Z has the structure

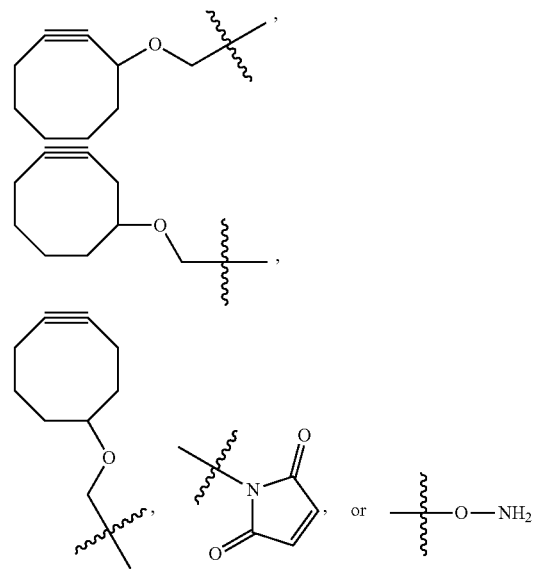

wherein the wavy line marks the covalent bond between Z and Y, or X when Y is a covalent bond, or W when Y and X are a covalent bond.

In a further embodiment, the distal end of the phosphate group is covalently linked to a payload, which may be a therapeutic agent such as a drug moiety or peptide, a radionuclide, or a protecting element, to provide a payload-phosphate-based linker compound comprising formula (II)

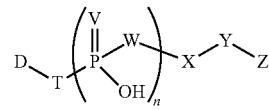

wherein V is selected from O and S; W is selected from O, N, and CH$_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group;

Y is optional but when present is selected from a covalent bond or a bivalent, straight or branched, saturated or unsaturated, optionally substituted C1-30 hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; Z is a reactive functional group selected from the group consisting of N-hydroxysuccinimidyl ester, para-nitrophenyl carbonate, para-nitrophenyl carbamate, methyl ketone, azide, hydrazine, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4. In particular embodiments, when Y is a covalent bond, X is not a covalent bond.

In particular aspect, the reactive group Z has the structure

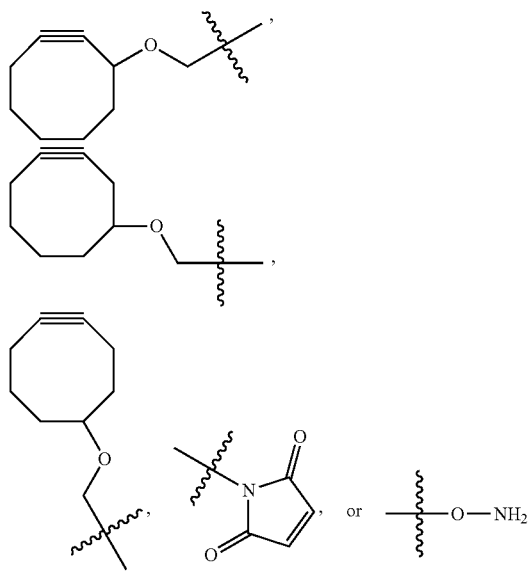

wherein the wavy line marks the covalent bond between Z and Y, or X when Y is a covalent bond, or W when Y and X are a covalent bond.

In a further embodiment, the reactive functional group at the proximal end of the payload-phosphate-based linker may be covalently linked to a ligand or targeting moiety to provide a conjugate wherein in particular embodiments, the ligand is capable of targeting the conjugate to a particular cellular target when administered to a subject in need of the payload to provide a compound having formula (III)

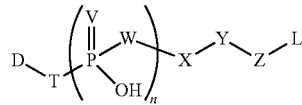

wherein V is selected from O and S; W is selected from O, N, and CH$_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is selected from a covalent bond or a bivalent, straight or branched, saturated or unsaturated, optionally substituted C$_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4. In particular embodiments, when Y is a covalent bond, X is not a covalent bond.

In particular aspects, the linkage Z has the structure

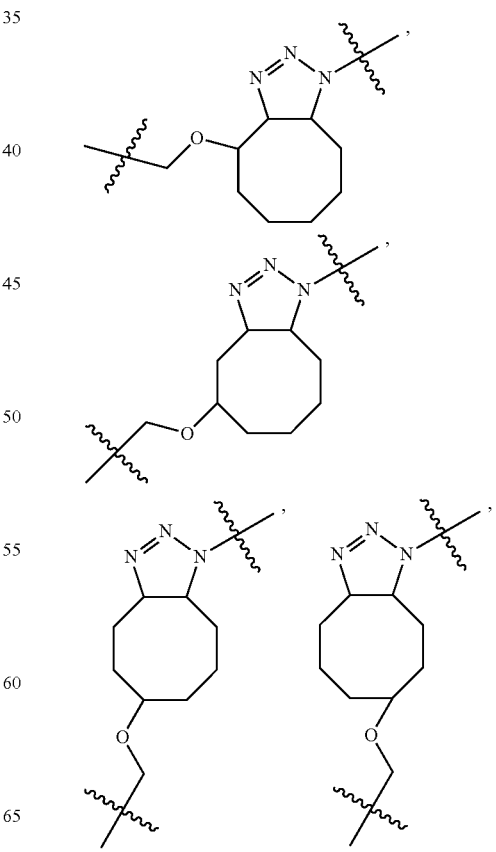

-continued

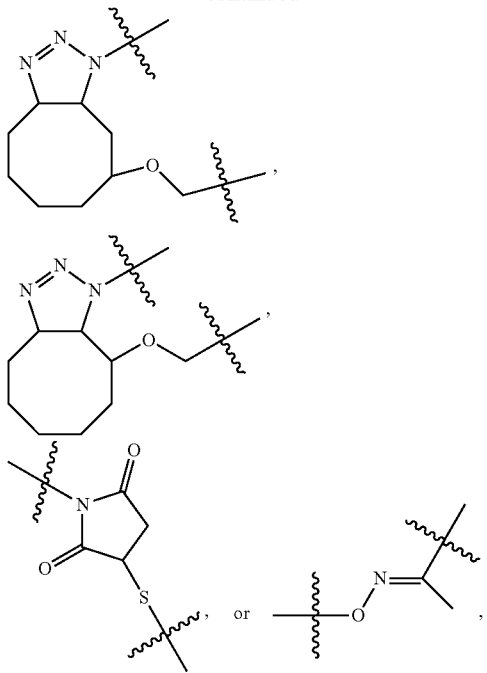

wherein the wavy lines represent the covalent bond between Z and Y, or X when Y is a covalent bond, or W when Y and X are a covalent bond (on the left) and Z and L (on the right), respectively.

In particular embodiments, the payload is a therapeutic agent, a detectable label, radionuclide, or protecting group. The therapeutic agent may be any molecule that alters, inhibits, activates, or otherwise affects a biological event. Examples of a therapeutic agent include but are not limited to, cytotoxic agent, an anti-inflammatory agent, peptide, a nucleic acid or nucleic acid analog, a small molecule, and a biomolecule.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclopropa[c]benz[e]-indol-4-one)-based analogues of the duocarmycins and CC-1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogs.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

In particular embodiments, the targeting ligand is an antibody or monoclonal antibody (e.g., chimeric, humanized, or human), ligand for a receptor, lectin, saccharide, poly(ethylene glycol), polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides a composition comprising a compound having formula (III)

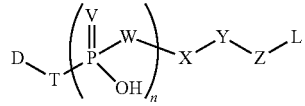

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4; and a pharmaceutically acceptable salt or carrier. In particular aspects, the composition is aqueous or lyophilized. In particular embodiments, when Y is a covalent bond, X is not a covalent bond.

In particular aspects, the linkage Z has the structure

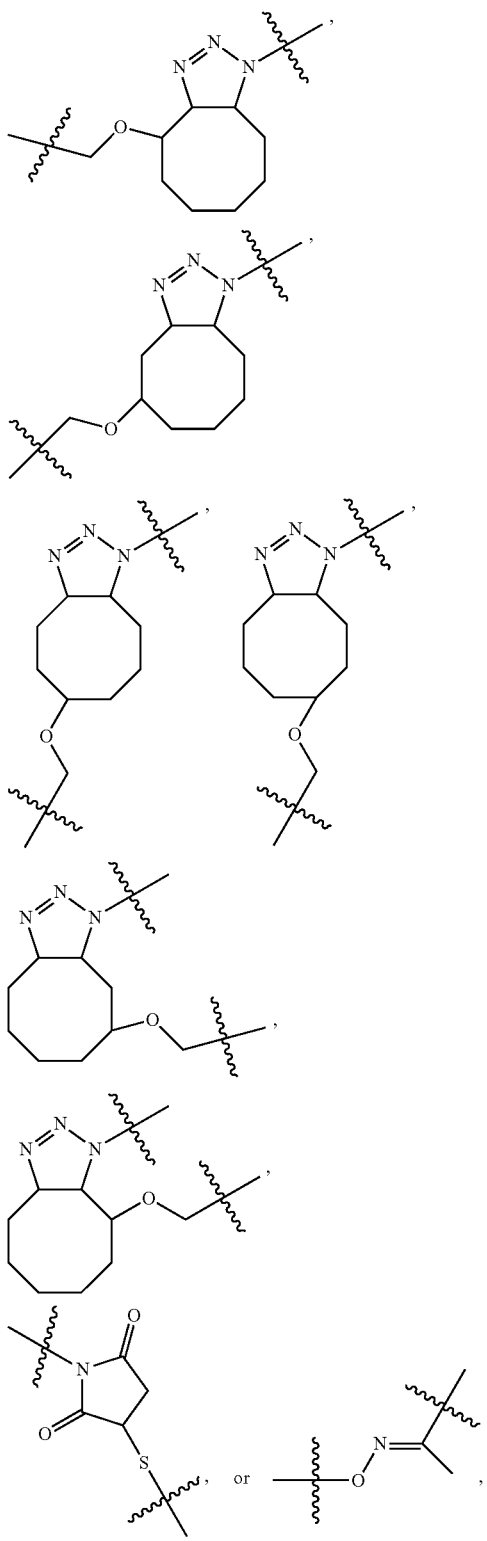

wherein the wavy lines mark the covalent bond between Z and Y, or X when Y is a covalent bond, or W when Y and X are a covalent bond (on the left) and Z and L (on the right), respectively.

In particular embodiments, the payload is a therapeutic agent, a detectable label, radionuclide, or protecting group. The therapeutic agent may be cytotoxic agent, an anti-inflammatory agent, peptide, or nucleic acid or nucleic acid analog.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues of the duocarmycins and CC— 1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogs.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

In particular embodiments, the targeting ligand is an antibody or monoclonal antibody (e.g., chimeric, humanized, or human) or fragment thereof, ligand for a receptor, lectin; saccharide, poly(ethylene glycol); polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides a method for treating a disease or disorder by providing to a subject having the disease or disorder a composition comprising a compound having formula (III)

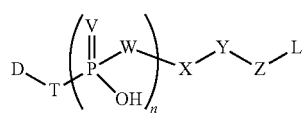

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4; and a pharmaceutically acceptable salt or carrier. In particular embodiments, when Y is a covalent bond, X is not a covalent bond.

In particular aspects, the linkage Z has the structure

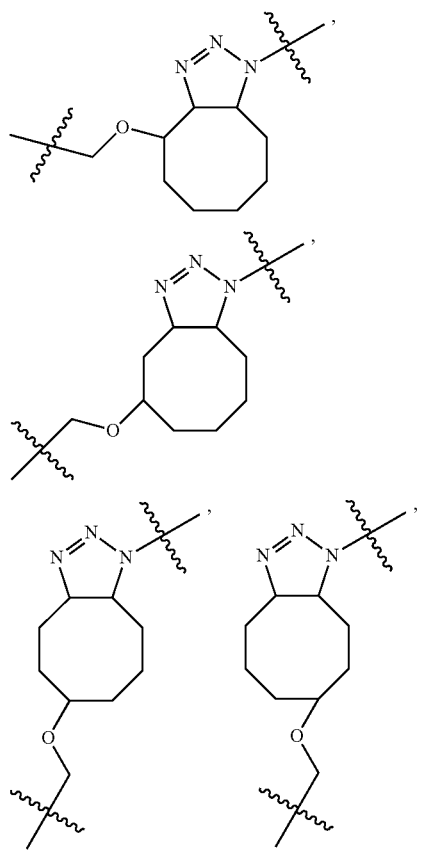

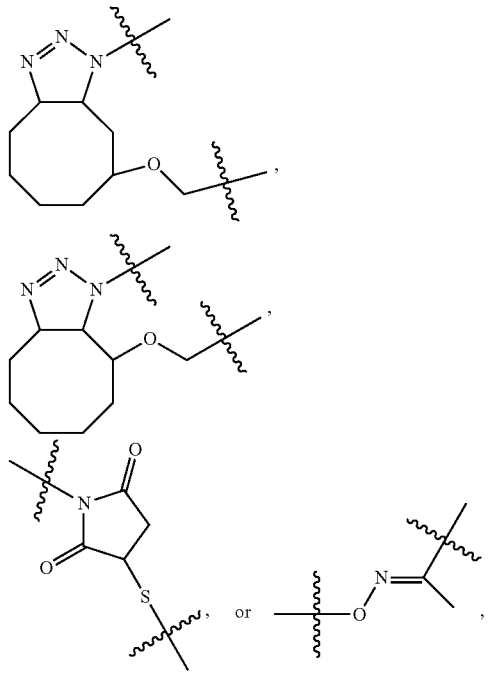

wherein the wavy lines mark the covalent bond between Z and Y, or X when Y is a covalent bond, or W when Y and X are a covalent bond (on the left) and Z and L (on the right), respectively.

In particular aspects, the disease or disorder is an inflammatory disease or cancer.

In particular embodiments, the payload is a therapeutic agent, which may be a cytotoxic agent, an anti-inflammatory agent, peptide, or nucleic acid or nucleic acid analog.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues of the duocarmycins and CC— 1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogs.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

In particular embodiments, the targeting ligand is an antibody or monoclonal antibody (e.g., chimeric, humanized, or human) or fragment thereof, ligand for a receptor, lectin, saccharide, poly(ethylene glycol), polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides for the use of composition comprising a compound having formula (III)

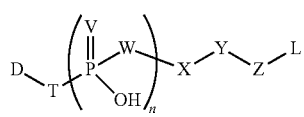

wherein V is selected from O and S; W is selected from O, N, and CH$_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is selected from a covalent bond or a bivalent, straight or branched, saturated or unsaturated, optionally substituted C$_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4; and a pharmaceutically acceptable salt or carrier for the treatment of a disease or disorder. In particular embodiments, when Y is a covalent bond, X is not a covalent bond.

In particular aspects, the linkage Z has the structure

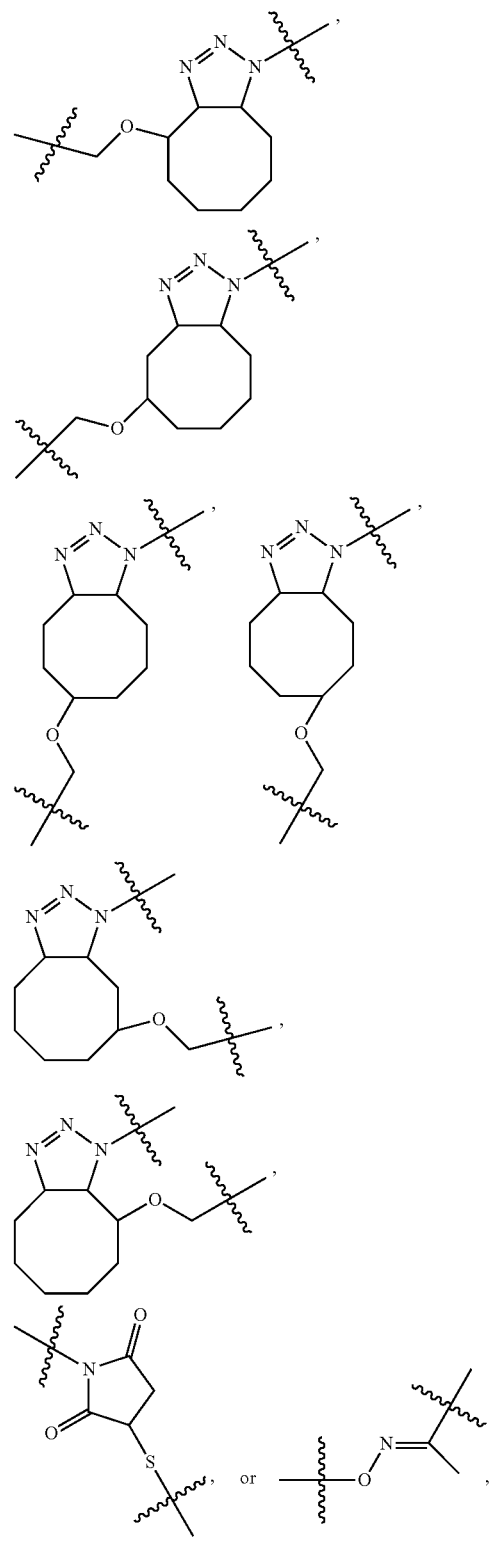

wherein the wavy lines mark the covalent bond between Z and Y, or X when Y is a covalent bond, or W when Y and X are a covalent bond (on the left) and Z and L (on the right), respectively.

In particular aspects, the disease or disorder is an inflammatory disease or cancer.

In particular embodiments, the payload is a therapeutic agent such as a cytotoxic agent, an anti-inflammatory agent, peptide, or nucleic acid or nucleic acid analog.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues of the duocarmycins and CC—1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogues.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

In particular embodiments, the targeting ligand is an antibody or monoclonal antibody (e.g., chimeric, humanized, or human), ligand for a receptor, lectin, saccharide, poly(ethylene glycol), polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides an anti-inflammatory compound comprising the formula

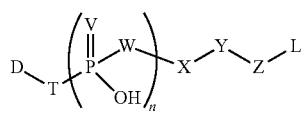

wherein
V is selected from O and S;
W is selected from O, N, and CH2;
X is selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group;

Y is selected from a covalent bond or a bivalent, straight or branched, saturated or unsaturated, optionally substituted C1-30 hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

T is an NR, CR2, O, or S;

D is an anti-inflammatory agent;

Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on the cell-specific targeting ligand (L);

Each occurrence of R is independently hydrogen, a suitable protecting group, an acyl moiety, arylalkyl moiety, aliphatic moiety, aryl moiety, heteroaryl moiety, or heteroaliphatic moiety;

L is a cell-specific targeting ligand; and n is 1, 2, 3, or 4. In particular embodiments, when Y is a covalent bond, X is not a covalent bond.

In further aspects, the anti-inflammatory agent is a glucocorticoid receptor agonist.

In further aspects, the anti-inflammatory agent is Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD11a antibody, anti-CTLA4 antibody, or anti-BLys antibody.

In particular aspects, the linkage Z has the structure

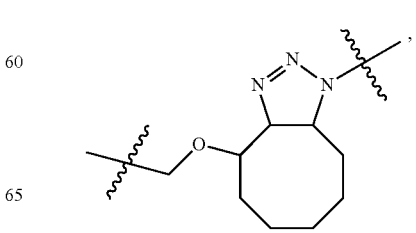

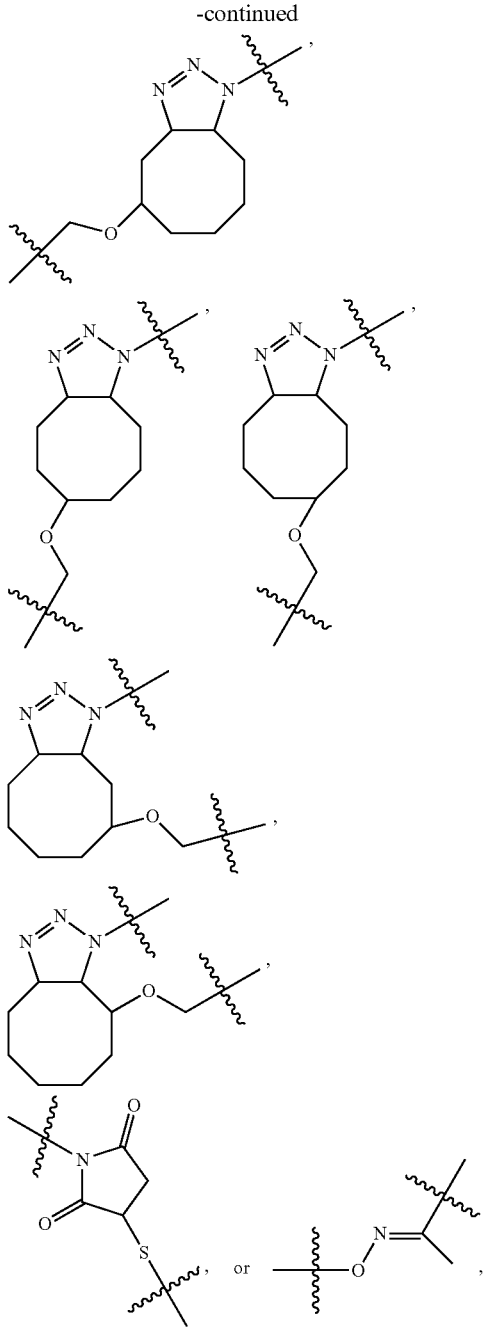

wherein the wavy lines mark the covalent bond between Z and Y, or X when Y is a covalent bond, or W when Y and X are a covalent bond (on the left) and Z and L (on the right), respectively.

The present invention further provides an anti-cancer compound comprising the formula

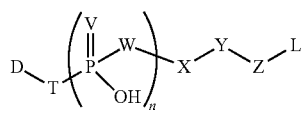

wherein
V is selected from O and S;
W is selected from O, N, and CH2;
X is selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group;
Y is selected from a covalent bond or a bivalent, straight or branched, saturated or unsaturated, optionally substituted C1-30 hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;
T is an NR, CR2, O, or S;
D is a cytotoxic agent;
Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on the cell-specific targeting ligand (L);
Each occurrence of R is independently hydrogen, a suitable protecting group, an acyl moiety, arylalkyl moiety, aliphatic moiety, aryl moiety, heteroaryl moiety, or heteroaliphatic moiety;
L is a cell-specific targeting ligand; and
n is 1, 2, 3, or 4. In particular embodiments, when Y is a covalent bond, X is not a covalent bond.

In further aspects, wherein the cytotoxic agent is selected from duocarmycins and CC-1065;

28. The compound of claim 26, wherein the cytotoxic agent is selected from a CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetrahydrocyclo-propa[c]benz[e]-indol-4-one)-based analogue of the duocarmycins and CC— 1065.

In further aspects, the cytotoxic agent is selected from doxorubicin and doxorubicin conjugates such as morpholino-doxorubicin and cyanomorpholino-doxorubicin.

In further aspects, the cytotoxic agent is selected from dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and analogs thereof.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD11a antibody, anti-CTLA4 antibody, or anti-BLys antibody.

In particular aspects, the linkage Z has the structure

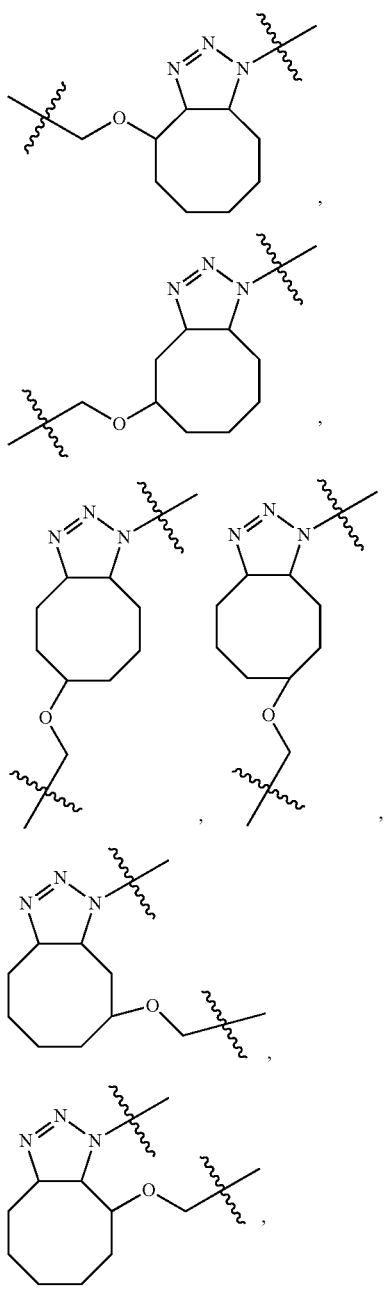

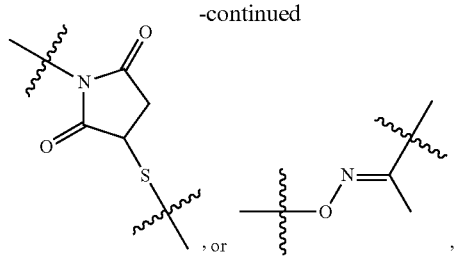

wherein the wavy lines mark the covalent bond between Z and Y, or X when Y is a covalent bond, or W when Y and X are a covalent bond (on the left) and Z and L (on the right), respectively.

The present invention further provides a method for making an antibody-drug conjugate that has reduced propensity for forming aggregates comprising:

(a) providing a compound comprising the formula

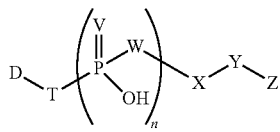

wherein
V is selected from O and S;
W is selected from O, N, and CH2;
X is selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group;
Y is selected from a covalent bond or a bivalent, straight or branched, saturated or unsaturated, optionally substituted C1-30 hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;
T is an NR, CR2, O, or S;
Z is a reactive functional group selected from the group consisting of N-hydroxysuccinimidyl ester, para-nitrophenyl carbonate, para-nitrophenyl carbamate, methyl ketone, azide, hydrazine, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S;
D is a payload;
Each occurrence of R is independently hydrogen, a suitable protecting group, an acyl moiety, arylalkyl moiety, aliphatic moiety, aryl moiety, heteroaryl moiety, or heteroaliphatic moiety; and
n is 1, 2, 3, or 4; and
(b) conjugating the compound to an antibody to make the antibody-drug conjugate that has reduced propensity for forming aggregates compared to an antibody-drug conjugate not conjugated to the compound.

In further aspects, the payload is a therapeutic agent, a detectable label, radionuclide, or protecting group. In particular embodiments, when Y is a covalent bond, X is not a covalent bond.

In further aspects, the therapeutic agent is a cytotoxic agent, an anti-inflammatory agent, peptide, or nucleic acid or nucleic acid analog.

In further aspects, the anti-inflammatory agent is a glucocorticoid receptor agonist.

In further aspects, the anti-inflammatory agent is Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

In further aspects, the cytotoxic agent is selected from duocarmycins and CC-1065.

In further aspects, the cytotoxic agent is selected from a CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogue of the duocarmycins and CC—1065.

In further aspects, the cytotoxic agent is selected from doxorubicin and doxorubicin conjugates such as morpholino-doxorubicin and cyanomorpholino-doxorubicin.

In further aspects, the cytotoxic agent is selected from dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and analogs thereof.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

In particular aspect, the reactive group Z has the structure

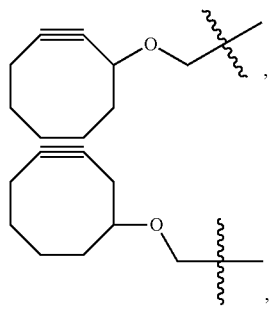

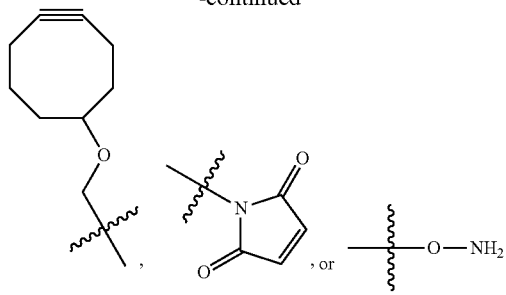

wherein the wavy line is the covalent bond between Z and Y, or X when Y is a covalent bond, or W when Y and X are a covalent bond.

The present invention further provides a method for making a composition of antibody-drug conjugates in which the propensity of the antibody-drug conjugates in the composition to form aggregates is reduced comprising:

(a) providing a multiplicity of compounds comprising the formula

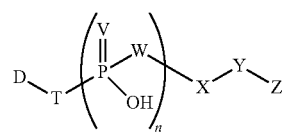

wherein

V is selected from O and S;

W is selected from O, N, and CH2;

X is selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group;

Y is selected from a covalent bond or a bivalent, straight or branched, saturated or unsaturated, optionally substituted C1-30 hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

T is an NR, CR2, O, or S;

Z is a reactive functional group selected from the group consisting of N-hydroxysuccinimidyl ester, para-nitrophenyl carbonate, para-nitrophenyl carbamate, methyl ketone, azide, hydrazine, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S;

D is a payload;

each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4; and (b) conjugating the compounds to a multiplicity of antibodies to make the composition in which the propensity of the antibody-drug conjugates therein to form aggregates is reduced compared to an antibody-drug conjugate that are not conjugated to the compound. In particular embodiments, when Y is a covalent bond, X is not a covalent bond.

In further aspects, the payload is a therapeutic agent, a detectable label, radionuclide, or protecting group.

In further aspects, the therapeutic agent is a cytotoxic agent, an anti-inflammatory agent, peptide, or nucleic acid or nucleic acid analog.

In further aspects, the anti-inflammatory agent is a glucocorticoid receptor agonist.

In further aspects, the anti-inflammatory agent is Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

In further aspects, the cytotoxic agent is selected from duocarmycins and CC-1065.

In further aspects, the cytotoxic agent is selected from a CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogue of the duocarmycins and CC—1065.

In further aspects, the cytotoxic agent is selected from doxorubicin and doxorubicin conjugates such as morpholino-doxorubicin and cyanomorpholino-doxorubicin.

In further aspects, the cytotoxic agent is selected from dolestatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and analogs thereof.

In further aspects, the percent of aggregated antibody-drug-conjugate in the composition is 2% or less, 1.5% or less, 1.0% or less, 5% or less, 1% or less, or undetectable.

In further aspects, at least 90%, 95%, 96%, 97% 98%, 99%, 99.5%, 99.4%, 99.3%, or 99.2% of the antibody-drug conjugates in the composition is not aggregated.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

In particular aspect, the reactive group Z has the structure

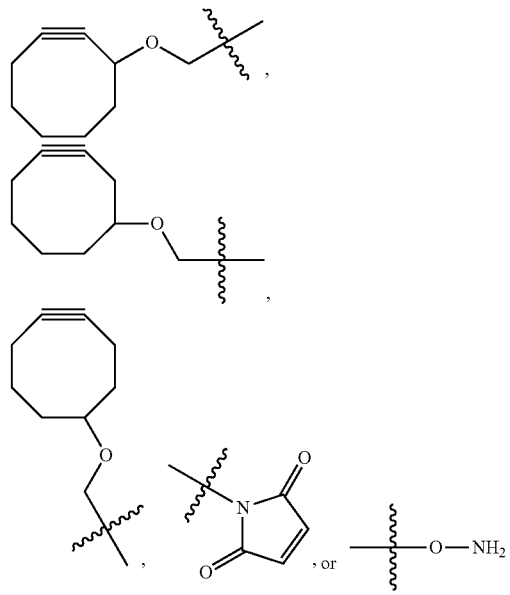

wherein the wavy line marks the covalent bond between Z and Y, or X when Y is a covalent bond, or W when Y and X are a covalent bond.

Definitions

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

Acyl—As used herein, the term "acyl," refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)ORX$^1$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., —(CH$_2$)$_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic.

The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$R; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR; —(CH$_2$)$_{0-4}$C(O)OSiR°$_3$; —(CH$_2$)$_{0-4}$OC(O)R; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR$_2$; —(CH$_2$)$_{0-4}$S(O)R°; —N(R°)S(O)$_2$NR°$_2$; —N(R°)S(O)$_2$R; —N(OR)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R˙, -(haloR˙), —(CH$_2$)$_{0-2}$OH, —(CH$_2$)$_{0-2}$OR˙, —(CH$_2$)$_{0-2}$CH(OR)$_2$; —O(haloR˙), —CN, —N$_3$, —(CH$_2$)$_{0-2}$C(O)R˙, —(CH$_2$)$_{0-2}$C(O)OH, —(CH$_2$)$_{0-2}$C(O)OR˙, —(CH$_2$)$_{0-2}$SR˙, —(CH$_2$)$_{0-2}$SH, —(CH$_2$)$_{0-2}$NH$_2$, —(CH$_2$)$_{0-2}$NHR˙, —(CH$_2$)$_{0-2}$NR˙$_2$, —NO$_2$, —SiR˙$_3$, —OSiR˙$_3$, —C(O)SR˙, —(C$_{1-4}$ straight or branched alkylene)C(O)OR˙, or —SSR˙ wherein each R˙ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of Rt are independently halogen, —R˙, -(haloR˙), OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in Protecting Groups in Organic Synthesis, T. W. Greene and P. G. M. Wuts, 3$^{rd}$ edition, John Wiley & Sons, 1999.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)

acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl) bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Antibody—As used herein the term "antibody" includes monoclonal antibodies, polyclonal antibodies, monospecific antibodies, and multispecific antibodies (e.g., bispecific antibodies) and the term "antibody" is used interchangeably with the terms "immunoglobulin," "immunoglobulins" and "immunoglobulin molecule". Each antibody molecule has a unique structure that allows it to bind its specific antigen, but all antibodies have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD and IgE, respectively. Thus, an antibody as defined herein can be of any type or class (e.g., IgG, IgE, IgM, IgD, and IgA) or subclass (e.g., IgG1, IgG2, IgG3, IgG4, IgA1 and IgA2).

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3 and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the $C_H2$ domain of the heavy chain immunoglobulin constant region which comprises an N-linked glycosylation site of the $C_H2$ domain, or a variant thereof. Included within the terms are molecules comprising only the Fc region, such as immunoadhesins (U.S. Published Patent Application No. 20040136986), Fc fusions, and antibody-like molecules. Alternatively, these terms can refer to an antibody fragment of at least the Fab region that at least contains an N-linked glycosylation site.

The term "Fc" fragment refers to the 'fragment crystallized' C-terminal region of the antibody containing the CH2 and CH3 domains. The term "Fab" fragment refers to the 'fragment antigen binding' region of the antibody containing the $V_H$, $C_H1$, $V_L$ and $C_L$ domains.

The term "antibodies" further includes chemical analogues and derivatives of antibodies and antibody fragments, provided that the antibody or antibody fragment maintains its ability to bind specifically to its target antigen. Thus, for example, chemical modifications are possible (e.g., glycosylation, acetylation, PEGylation and other modifications without limitation) provided specific binding ability of the antibody is retained. An antibody may be, for example, human, humanized, or chimeric A "monoclonal antibody" is an antibody obtained from a population of substantially homogeneous antibodies, i.e., individual antibodies comprising the population are identical except for possible naturally-occurring mutations that may be present in minor amounts. Monoclonal antibodies (mAbs) are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be synthesized by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567 to Cabilly et al.).

Monoclonal antibodies further include chimeric antibodies in which a portion of the heavy and/or light chain is identical to or homologous with the corresponding s of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one that comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains such as human native sequence constant domains or amino acid sequence variants thereof. An intact antibody may or may not have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, camelids, or an epitope-binding fragments of any of the above which immunospecifically bind to a target antigen (e.g., a cancer cell antigen).

"Humanized" forms of non-human (e.g., rodent) antibodies are chimeric antibodies that contain minimal sequence derived from non-human immunoglobulin. The term "capable of specific binding" refers to protein or peptide (e.g., antibody) binding to a predetermined target substance (e.g., an antigen and/or groups of antigens), e.g. a target substance that is expressed on the surface of a cell; thus the term "binding to a target cell" or "binding to a cancer cell" is to be understand as referring to protein or peptide (e.g., antibody) binding to a predetermined target substance (e.g. antigen or antigens) that is expressed on such a cell.

Typically, the protein or peptide (e.g., antibody) binds with an affinity of at least about $1 \times 10^7$ M$^1$, and/or binds to the predetermined target substance (e.g., antigen, antigens or cell) with an affinity that is at least two-fold greater than its affinity for binding to a non-specific control substance (e.g., BSA, casein, non-cancer cells) other than the predetermined target substance or a closely-related target substance.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes, cancer, inflammatory disease), a symptom or symptoms of a condition (e.g., hyperglycemia), or the predisposition toward a condition.

DETAILED DESCRIPTION OF THE INVENTION

Figure 1:
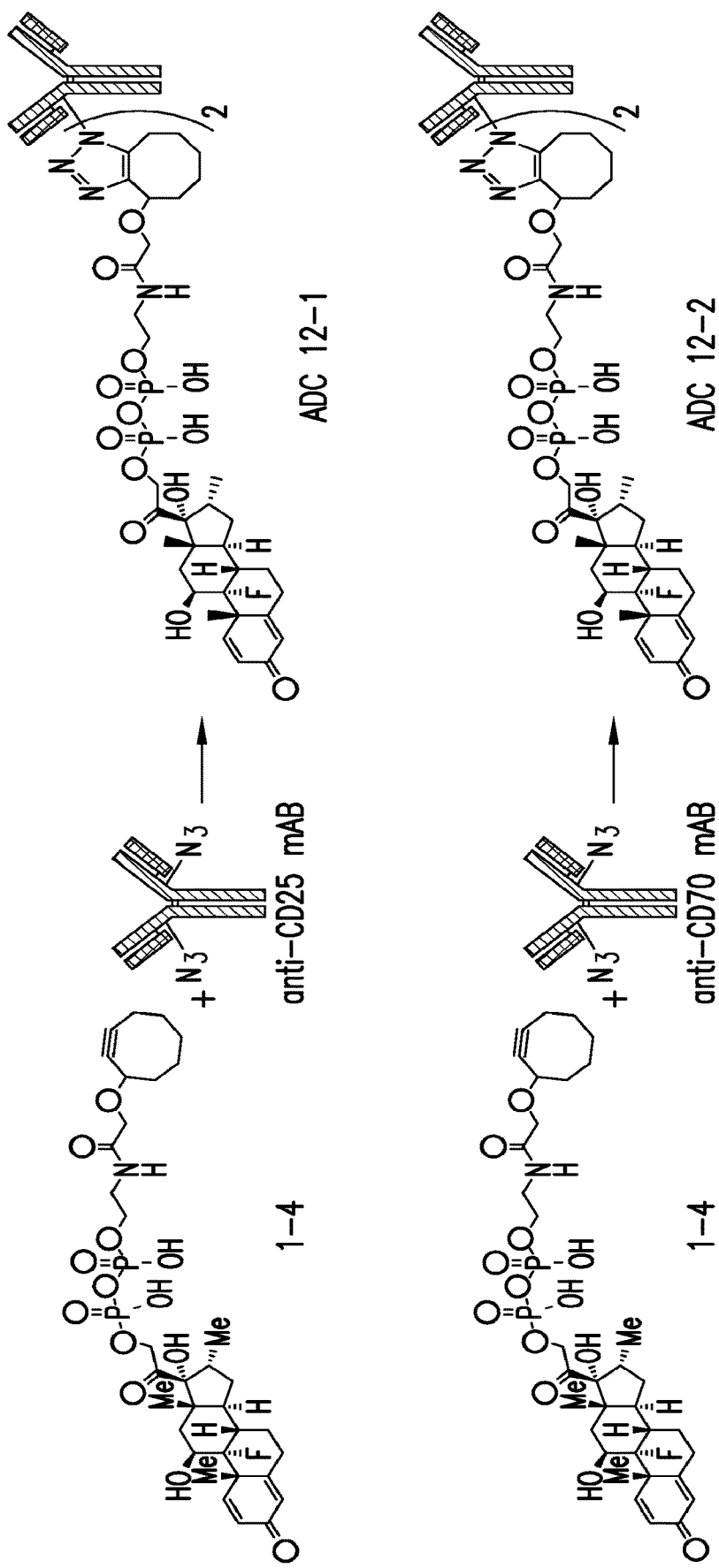
FIG. 1 shows a scheme for synthesis of ADC 12-1 and ADC 12-2.

The present invention provides phosphate-based linkers comprising a monophosphate, diphosphate, triphosphate, or tetraphosphate group and a linker arm comprising a tuning element, an optional spacer element, and a reactive functional group. The phosphate-based linkers have a distal end and a proximal end. The distal end of the phosphate-based linker comprises a monophosphate, diphosphate, or triphosphate group (phosphate group) linked to the distal end of the tuning element comprising the linker arm. The proximal end of the linker arm comprises a reactive functional group capable of reacting with a group on a ligand or targeting moiety to covalently link the phosphate-based linker to the ligand or targeting moiety. Interspersed between the tuning element and the reactive functional group of the linker arm may be an optional spacer element.

In general, the phosphate-based linker is a compound that has the following formula (I)

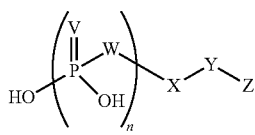

Wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is optional but when present it is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, methyl ketone, azide, hydrazine, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In particular aspect, the reactive group Z has the structure

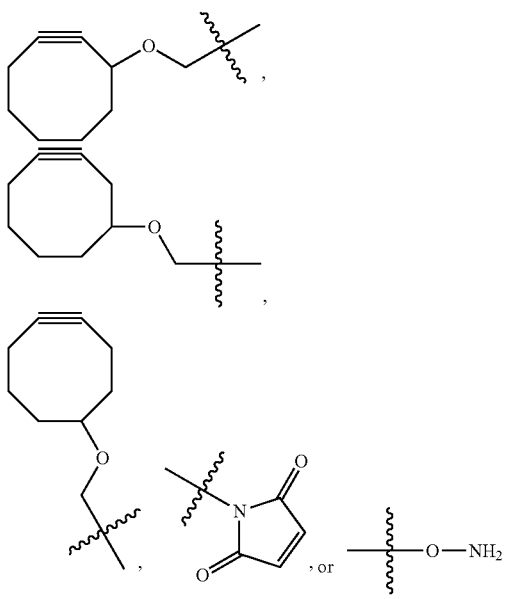

wherein the wavy line marks the bond between Z and Y, or X when Y is a covalent bond, or W when Y and X are a covalent bond.

In a further embodiment, the distal end of the phosphate group is covalently linked to a payload, which may be a therapeutic agent such as a drug moiety or peptide, a radionuclide, or a protecting element, to provide a payload-phosphate-based linker compound comprising formula (II)

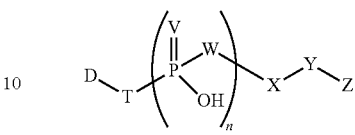

Wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; Z is a reactive functional group selected from the group consisting of N-hydroxysuccinimidyl ester, para-nitrophenyl carbonate, para-nitrophenyl carbamate, methyl ketone, azide, hydrazine, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In particular aspect, the reactive group Z has the structure

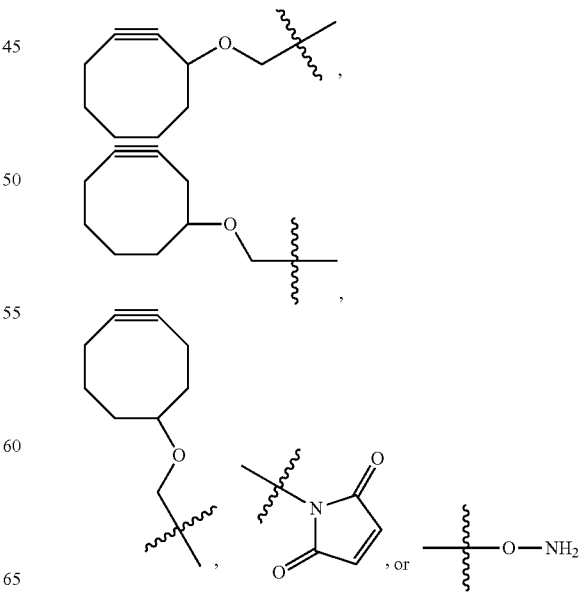

wherein the wavy line marks the covalent bond between Z and Y, or X when Y is a covalent bond, or W when Y and X are a covalent bond.

In a further embodiment, the reactive functional group at the proximal end of the payload-phosphate-based linker may be covalently linked to a ligand or targeting moiety to provide a conjugate wherein in particular embodiments, the ligand is capable of targeting the conjugate to a particular cellular target when administered to a subject in need of the payload.

Such a compound comprises formula (III)

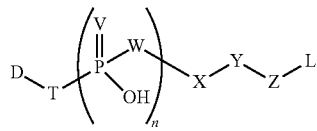

Wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin K sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4.

In particular aspects, the linkage Z has the structure

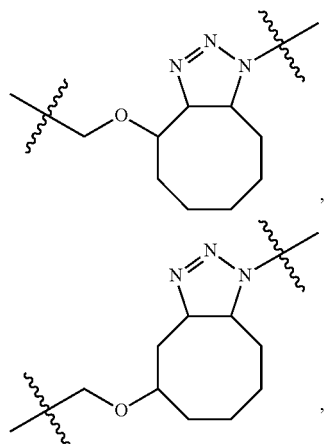

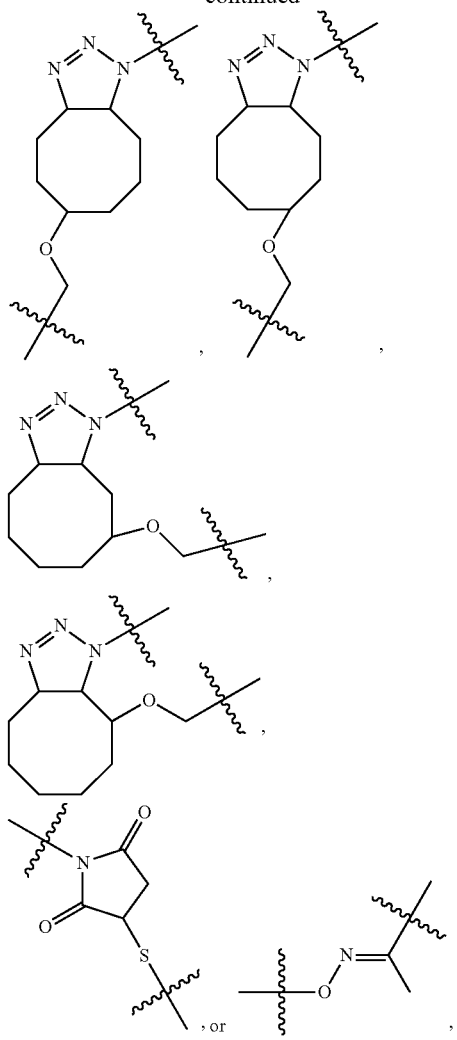

wherein the wavy lines mark the covalent bond between Z and Y, or X when Y is a covalent bond, or W when Y and X are a covalent bond (on the left) and Z and L (on the right), respectively.

In particular embodiments, the payload-ligand conjugate compound comprising a cell-specific targeting ligand conjugated to a drug moiety comprises the formula (IV)

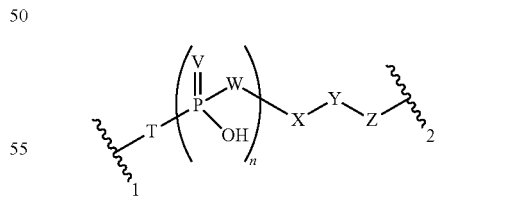

wherein wavy line 1 indicates the covalent attachment site to the payload and wavy line 2 indicates the covalent attachment site of the cell-specific targeting ligand and wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S of the payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S, and (ii) an S, NR, or O group on the cell-specific targeting ligand; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In particular aspects, the linkage Z has the structure

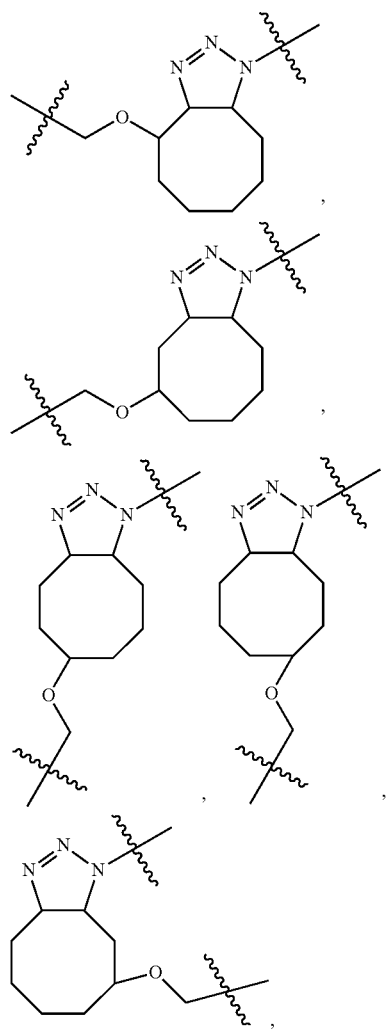

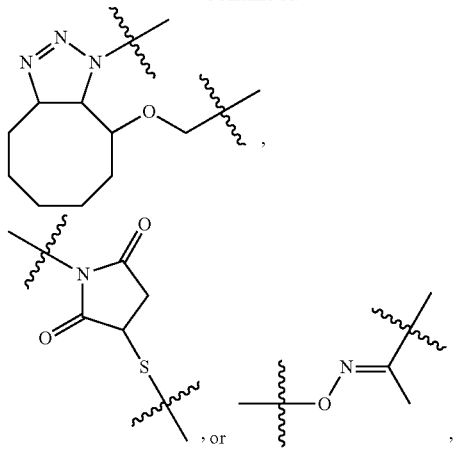

wherein the wavy lines mark the covalent bond between Z and Y, or X when Y is a covalent bond, or W when Y and X are a covalent bond (on the left) and Z and L (on the right), respectively.

The phosphate-payload linkage is stabile extracellularly and labile intracellularly, for example, when present in the lysosomal compartment of the target cell. The tuning element provides a tunable stability to the phosphate-drug linkage when the conjugate is within the lysosomal compartment of the target cell. The intracellular stability of the phosphate-payload linkage or rate of intracellular release of the payload from the conjugate may be adjusted or tuned by the particular tuning element adjacent to the phosphate group and/or by adjusting the number of the phosphate groups. The conjugates disclosed herein are particularly useful in embodiments in which the ligand is an antibody or antibody fragment and the payload is a therapeutic agent, for example, a cytotoxin or a glucocorticoid receptor agonist, which herein is referred to as an "antibody drug conjugate" or "ADC".

The link between the antibody and the drug moiety plays an important role in an antibody drug conjugate (ADC), as the type and structure of the linker may significantly affect the potency, selectivity, and the pharmacokinetics of the resulting conjugate (Widdeson et al, J. Med. Chem. 49: 4392-4408 (2006); Doronina et al., Bioconj. Chem. 17: 114-124 (2006); Hamann et al., Bioconj. Chem. 16: 346-353 (2005); King et al., J. Med. Chem. 45: 4336-4343 (2002); Alley et al., Bioconj. 19: 759-765 (2008); Blaittler et al., Biochem. 24: 1517-1524 (1985). ADC delivery of a drug moiety to its intracellular target occurs via a multistep sequence of events: binding to the cell surface, endocytosis, trafficking (within an endosome) to a lysosome, proteolytic degradation of the conjugate, and diffusion of the released drug moiety across the lysosomal or endosomal membrane toward its intracellular target and its interaction with the target. Therefore, the linker should be sufficiently stable while in circulation to allow delivery of the intact ADC to the target cell but, on the other hand, sufficiently labile to allow release of the drug moiety from the ADC once inside the targeted cell. In general, four types of linkers have been used for preparation of ADCs that have currently entered the clinic: (a) acid-labile linkers, exploiting the acidic endosomal and lysosomal intracellular microenvironment (Hamann et al., op. cit.; Blittler et al., op. cit.); (b) linkers cleavable by lysosomal proteases (Dronina et al. op. cit.; King et al. op. cit.); (c) chemically stable thioether linkers that release a lysyl adduct after proteolytic degradation of the antibody inside the cell; (Lewis et al Cancer Res. 68: 9280-9290 (2008); Erickson et al., Cancer Res. 66: 4426-4433 (2006) and (d) disulfide containing linkers (Chari, Adv. Drug Delivery Rev. 31: 89-104 (1998); Widdeson et al., op. cit.), which are cleaved upon exposure to an intracellular thiol. While U.S. Pat. No. 5,094,848 discloses conjugates comprising a diphosphate or amidated diposphate group and a linker arm wherein the linker arm may preferably be an oligopeptide having preferably 2-10 amino acids, in particular embodiments the tuning element of the phosphate-based linkers disclosed herein may include a di-peptide.

The payload-linker conjugates of the present invention wherein the payload is covalently linked to a tuning element of the linker via a monophosphate, diphosphate, triphosphate, or tetraphosphate linkage have a differentiated and tunable stability of the phosphate linkage in blood vs. an intracellular environment (e.g. lysosomal compartment). Due to location of enzymes that recognize the phosphate linkage, conjugates that have a phosphate group linking a payload to a tuning element of the linker are stable in circulation (plasma or blood) but reactive in intracellular compartments (e.g., lysosomes) making them suitable for intracellular delivery of payload conjugates. The exemplary payload-phosphate-based linker conjugates in the Examples show that the payload-phosphate-based linker conjugates of the present invention are stable in blood, which is advantageous for extending the half-life and to prevent premature release of payload from the conjugates.

Importantly, the inventors have discovered that by modifying the tuning element and/or V and/or W, and/or the number of phosphate groups, the ability to tune reactivity or cleavage of the phosphate linkage in a lysosomal environment so as to release the payload from the conjugate. In general, the rate of release of the payload is dependent on the proximal substitution of the tuning element. The ability to cleave the phosphate linkage between the payload and the tuning element efficiently in a lysosome is advantageous for the release of the payload from the conjugate once it has been delivered to a cell and internalized through an endosomal pathway. Of note is that unlike other linkers known in the art, there is no need to for the phosphate-based linkers of the present invention to be self-immolative. In addition, the excellent solubility of the payload-phosphate-based linker facilitates conjugation to a ligand or cell-targeting moiety and minimizes aggregation of the conjugates. In addition, the phosphate contributes to retention of the payload to the conjugate within cell until phosphate linkage is fully cleaved and limits permeability of conjugates containing the payload from entering non-target cells.

The phosphate-based linkers provide greater solubility relative to disulfide linkers, cathepsin B-cleavable linkers, esters and acid-sensitive linkers such as hydrazones. They enable the release of the payload in its parent or unadultered form unlike some of the alternative linkers, and may offer an improved blood/lysosome stability profile. Specifically, these phosphate-based linkers will provide superior blood stability relative to esters and disuflides. Phosphate-based linkers, following lysosomal cleavage will release an alcohol or amine-containing payload whereas the other linker formats may require self-immolative tethers to accomplish this or leave residual linker on the payload after lysosomal cleavage. The phosphate-based linker may have greater blood stability relative to the self-immolative cathepsin B linkers in the art, particularly when attached via the oxygen atom of a hydroxyl group of an alcohol-containing payload. The enzymatic hydrolysis of the phosphate linkage may be more rapid than the acid-hydrolysis of hyrdazones. The phosphate-based linkers disclosed herein minimize the propensity for conjugates comprising particular payloads to aggregate. For example, antibody-drug conjugates comprising duocarmycin are known to have a propensity to aggregate. However, antibodies conjugated to duocarmycin via a phosphate-based linker disclosed herein did not produce detectable aggregates. Thus, the phosphate-based linkers disclosed herein are particularly useful for conjugating payloads that are prone to forming aggregates to a cell-specific targeting ligand to provide a conjugate with a reduced or no detectable propensity for aggregation.

Thus, the phosphate-based linkers disclosed herein provide an ideal design for antibody-drug conjugates and the like.

Phosphate Group

The phosphate group comprising the phosphate-based linkers disclosed herein may comprise 1, 2, 3, or 4 phosphate atoms. In particular embodiments, the phosphate group may be a phosphate ester

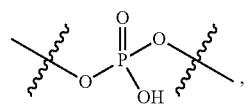 [SMILES: *OP(=O)(O)O*]

pyrophosphate ester

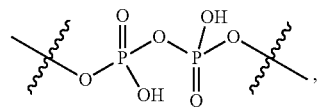 [SMILES: *OP(=O)(O)OP(=O)(O)O*]

triphosphate ester

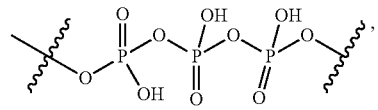 [SMILES: *OP(=O)(O)OP(=O)(O)OP(=O)(O)O*]

or tetraphosphate ester

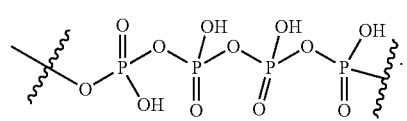

In further embodiments, the phosphate group may be a phosphoramidate

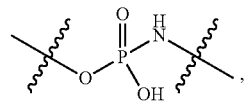 [SMILES: *NP(=O)(O)O*]

pyrophosphoramidate

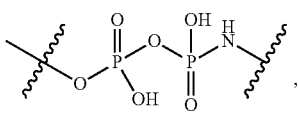 [SMILES: *NP(=O)(O)OP(=O)(O)O*]

triphosphophoramidate

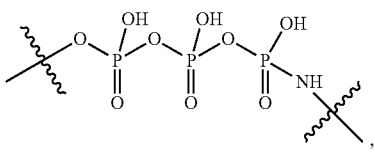 [SMILES: *NP(=O)(O)OP(=O)(O)OP(=O)(O)O*]

or tetraphosoramidate

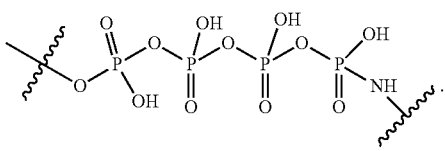 [SMILES: *NP(=O)(O)OP(=O)(O)OP(=O)(O)OP(=O)(O)O*]

In further still embodiments, the phosphate group may be a phosphonate

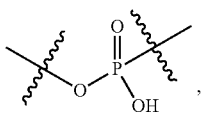 [SMILES: *OP(*)(=O)O]

a diposphonate

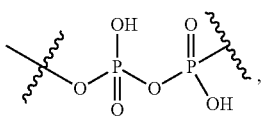 [SMILES: *OP(=O)(O)OP(*)(=O)O]

a phosphorthioate

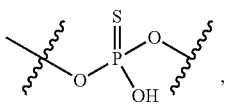 [SMILES: *OP(O)(=S)O*]

or a diphosphorthioate

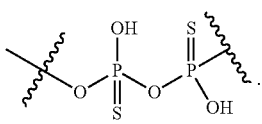 [SMILES: *OP(O)(=S)OP(*)(O)=S]

The wavy lines shown indicate the covalent attachment sites to the payload at the distal end (left) and the tuning element on the proximal end (right).

Payload

Payloads, depicted as "D" herein, are provided in the current invention as part of a payload-ligand conjugate where the payload is linked to a ligand via a phosphate-based linker comprising reactive functional group selected from the group consisting of N-hydroxysuccinimidyl ester, para-nitrophenyl carbonate, para-nitrophenyl carbamate, methyl ketone, azide, hydrazine, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S. The payload must possess a desired biological activity and contain a reactive functional group capable of forming a covalent linkage to the phosphate group of the phosphate-based linker. The desired biological activity includes the diagnosis, cure, mitigation, treatment, or prevention of disease in an animal such as a human. Thus, so long as it has the needed reactive functional group, the term "payload" refers to chemicals recognized as drugs in the official United States Pharmacopeia, official Homeopathic Pharmacopeia of the United States, or official National Formulary, or any supplement thereof. Exemplary drugs are set forth in the Physician's Desk Reference (PDR) and in the Orange Book maintained by the U.S. Food and Drug Administration (FDA). New drugs are being continually being discovered and developed, and the present invention provides that these new drugs may also be incorporated into the payload-ligand complex of the current invention. In particular embodiments, the functional groups on the drug include primary or secondary amines, hydroxyls, sulfhydryls, carboxyls, aldehydes, and ketones. The drug must have at least one, but may have 2, 3, 4, 5, 6 or more reactive functional groups. The payload may also be a biomolecule such as a peptide, polypeptide, or protein; a nucleic acid molecule or analog thereof, a carbohydrate, polysaccharide, a saccharide, or any other therapeutic agent that has a biological effect.

The payload-ligand conjugate is effective for the usual purposes for which the corresponding drugs are effective, but have superior efficacy because of the ability, inherent in the ligand, to transport the drug to the desired cell where it is of particular benefit. Exemplary drugs include proteins, peptides, and small molecule drugs containing a functional group for linkage to the phosphate moiety of the linker. More specifically, these drugs include, for example, the enzyme inhibitors such as dihydrofolate reductase inhibitors, and thymidylate synthase inhibitors, DNA intercalators, glutocorticoid receptor agonists, nuclear recemptor agonists, antinflammatory agents, DNA cleavers, topoisomerase inhibitors, the anthracycline family of drugs, the vinca drugs, the mitomycins, the bleomycins, the cytotoxic nucleosides, the pteridine family of drags, diynenes, the podophyllotoxins, differentiation inducers, and taxols.

In one embodiment, the drugs of the current invention include cytotoxic drugs useful in cancer therapy and other small molecules, proteins or polypeptides with desired biological activity, such as a toxin. The drug may be selected to be activated at a tumor cells by conjugation to a tumor-specific ligand. These tumor specific drug-ligand conjugates have tumor specificity arising from the specificity of the ligand. Examples of this are drug-ligand conjugates that are highly selective substrates for tumor specific enzymes, where these enzymes are present in the proximity of the tumor in sufficient amounts to generate cytotoxic levels of free drug in the vicinity of the tumor.

Cytotoxic drugs useful in the current invention include, for example, duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclopropa[c]benz[e]-indol-4-one)-based analogues of the duocarmycins and CC— 1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid—AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N—acetyl spermidine, camptothecin, and their analogues.

Anti-inflammatory agents, such as glucocorticoid receptor agonists include glucocorticoids such as Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

Linker Arm

The linker arm of the phosphate-based linkers disclosed herein comprises a tuning element at the distal end covalently linked to a phosphate group and a functional reactive group at the proximal end capable of covalent linkage to a cell-targeting ligand. Optionally, the linker arm may further include a spacer element interposed between the tuning element and the reactive functional group. Examples of tuning elements include but are not limited to $R_1$ and $R_2$ each independently any amino acid

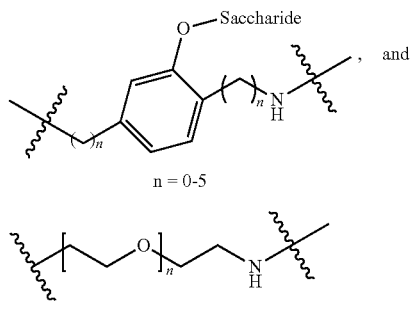

wherein n=0-5, and wherein n=1-50, or 1-30, or 1-20, or 1-10. The wavy lines mark the covalent bond to the O, N, or $CH_2$ of a phosphate group at the distal end (left) and the covalent bond to an atom of the functional reactive group on the proximal end (right), or optionally, a spacer element.

Further examples of tuning elements include but are not limited to

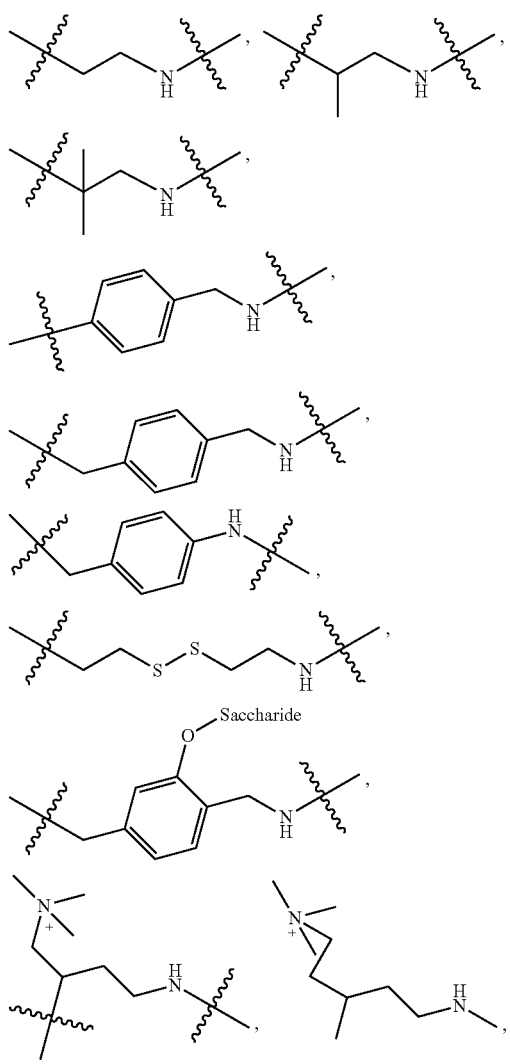
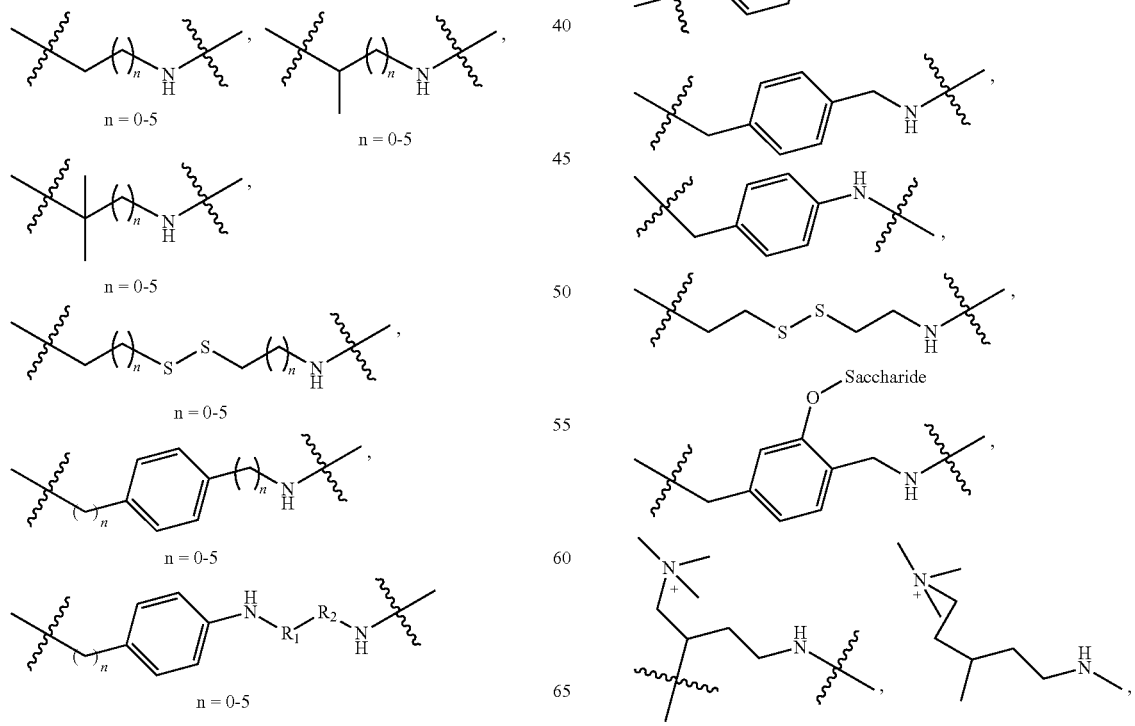

-continued

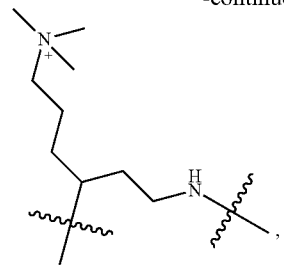

,

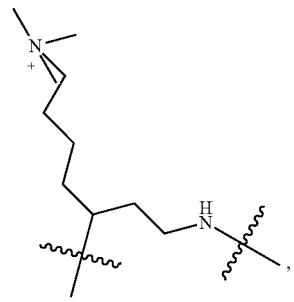

,

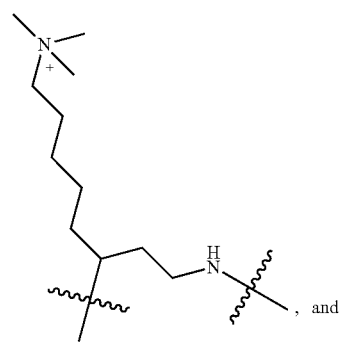

, and

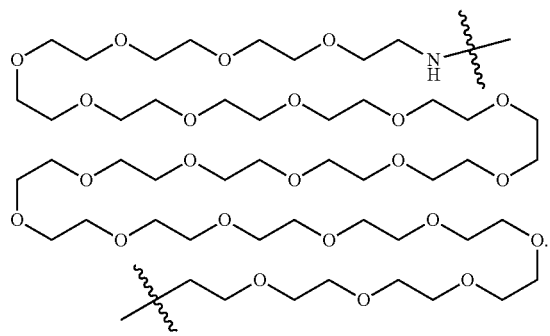

The wavy lines mark the covalent bond to the O, N, or CH$_2$ of a phosphate group at the distal end (left) and the covalent bond to an atom of the functional reactive group on the proximal end (right), or optionally, a spacer element.

In general, the spacer element is to allow for distance control away from the cell-targeting ligand. In some embodiments, this distance may have an impact on the stability/cleavability of the linker. Examples of spacer elements include straight polyethylglycol (PEG) chains (of a defined length), straight carbon chains with or without solubilizing groups attached thereto, a dipeptide, a tripeptide, a tetrapeptide, an enzyme cleavage site, for example, a cathepsin cleavage site having the structure

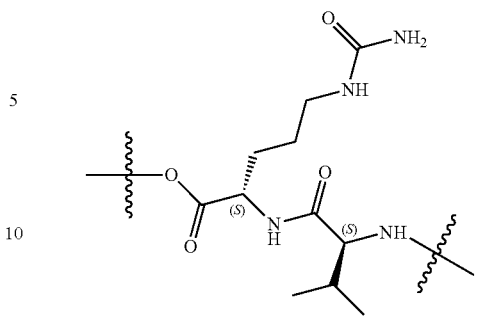

wherein the wavy line on the left marks the covalent bond to an atom in the tuning element and the wavy line on the right marks the covalent bond to an atom of a reactive group Z.

The present invention further provides a compound comprising a glucocorticoid receptor agonist conjugated to a phosphate-based linker, wherein the compound has the structure of compound 1-4, 2-7, 3-4, 4-3, 5-3, 6-2, 7-1, 8-5, 9-4, 10-1, 11-5, 12-3, 13-7, 14-5, 15-5, 16-5, 17-5, 18-3, 19-5, 20-5, or 21-5. The structures of these compounds are shown in Examples 1-21.

The present invention further provides antibody drug conjugates in which one or more of compounds 1-4, 2-7, 3-4, 4-3, 5-3, 6-2, 7-1, 8-5, 9-4, 10-1, 11-5, 12-3, 13-7, 14-5, 15-5, 16-5, 17-5, 18-3, 19-5, 20-5, or 21-5 is conjugated to the antibody. In particular embodiment, the antibody comprises one or more a non-natural amino acid having a reactive site capable of binding to compound 1-4, 2-7, 3-4, 4-3, 5-3, 6-2, 7-1, 8-5, 9-4, 10-1, 11-5, 12-3, 13-7, 14-5, 15-5, 16-5, 17-5, 18-3, 19-5, 20-5, or 21-5. In particular embodiments, the antibody comprises one or more para-azido-phenylalanine residues or para-acetyl-phenylalanine residues. In particular embodiments, the antibody-drug conjugate comprises compound 1-4, 2-7, 3-4, 4-3, 5-3, 6-2, 8-5, 9-4, 11-5, 12-3, 13-7, 14-5, 15-5, 16-5, 17-5, 18-3, or 19-5 conjugated to the azido group on a para-azido-phenylalanine residue within the antibody amino acid sequence. In particular embodiments, the antibody drug conjugate comprises compound 7-1 or 10-1 conjugated to a free thiol group within the amino acid sequence of the antibody, for example, the thio group of a cysteine residue, on the antibody. In particular embodiments, the antibody-drug conjugate comprises compound 20-5 or 21-5 conjugated to the methyl ketone group on a para-acetyl-phenylalanine residue within the antibody amino acid sequence The present invention further provides compositions comprising one or more antibody drug conjugates wherein at least one antibody drug conjugate is conjugated to compound 1-4, 2-7, 3-4, 4-3, 5-3, 6-2, 7-1, 8-5, 9-4, 10-1, 11-5, 12-3, 13-7, 14-5, 15-5, 16-5, 17-5, 18-3, 19-5, 20-5, or 21-5. In particular embodiment, the antibody comprises one or more a non-natural amino acid having a reactive site capable of binding to compound 1-4, 2-7, 3-4, 4-3, 5-3, 6-2, 7-1, 8-5, 9-4, 10-1, 11-5, 12-3, 13-7, 14-5, 15-5, 16-5, 17-5, 18-3, 19-5, 20-5, or 21-5.

In particular embodiments, the antibody comprises one or more para-azido-phenylalanine residues or para-acetyl-phenylalanine residues. In particular embodiments, the antibody-drug conjugate comprises compound 1-4, 2-7, 3-4, 4-3, 5-3, 6-2, 8-5, 9-4, 11-5, 12-3, 13-7, 14-5, 15-5, 16-5, 17-5, 18-3, or 19-5 conjugated to the azido group on a para-azido-phenylalanine residue within the antibody amino acid sequence. In particular embodiments, the antibody drug conjugate comprises compound 7-1 or 10-1 conjugated to a free thiol group within the amino acid sequence of the antibody, for example, the thio group of a cysteine residue, on the antibody. In particular embodiments, the antibody-drug conjugate comprises compound 20-5 or 21-5 conjugated to the methyl ketone group on a para-acetyl-phenylalanine residue within the antibody amino acid sequence.

Targeting Ligand

The linker arm and payload of the invention may be linked to a targeting ligand that selectively delivers a pay load to a cell, organ, or region of the body. Exemplary targeting ligands such as antibodies (e.g., chimeric, humanized and human), ligands for receptors, lectins, saccharides, antibodies, and the like are recognized in the art and are useful without limitation in practicing the present invention. Other targeting ligands include a class of compounds that do not include specific molecular recognition motifs include macromolecules such as poly(ethylene glycol), polysaccharide, polyamino acids and the like, which add molecular mass to the cytotoxin. The additional molecular mass affects the pharmacokinetics of the payload, e.g., serum half-life.

In an exemplary embodiment, the invention provides a payload, linker or payload-linker conjugate with a targeting ligand that is a biomolecule, e.g, an antibody, receptor, peptide, lectin, saccharide, nucleic acid or a combination thereof. Biomolecules useful in practicing the present invention may be derived from any source. The biomolecules may be isolated from natural sources or may be produced by synthetic methods. Proteins may be natural proteins or mutated proteins. Mutations may be effected by chemical mutagenesis, site-directed mutagenesis or other means of inducing mutations known to those of skill in the art. Proteins useful in practicing the instant invention include, for example, enzymes, antigens, antibodies and receptors. Antibodies may be either polyclonal or monoclonal, but most preferably are monoclonal and may be human, humanized, or human chimeric antibodies. Peptides and nucleic acids may be isolated from natural sources or can be wholly or partially synthetic in origin.

In a particular embodiment, the targeting ligand is an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies that are known in the art may be used in the conjugates of the invention, in particular for the treatment of the disease with which the target antigen is associated. Non-limiting examples of target antigens (and their associated diseases) to which a conjugate of the invention may be targeted include: Her2 (breast cancer), CD4 (lymphomas, autoimmune diseases, including rheumatoid arthritis), CD20 (lymphomas), EGFR (solid tumors), CD22 (lymphomas, including non-Hodgkin's lymphoma), CD23 (asthma), CD25, CD52 (chronic lymphocytic leukemia), CD30 (lymphomas, including non-Hodgkin's lymphoma), CD33 (acute myelogenous leukemia), CD40L (immune thrombocytopenic purpura), CD70, CD74, CD80 (psoriasis), CD163, Mucl8 (melanoma), integrins (solid tumors), PSMA (prostate cancer, benign prostatic hyperplasia), CEA (colorectal cancer), CD1 Ia (psoriasis), CTLA4 (T cell lymphomas) and BLys (autoimmune diseases, including systemic lupus erythematosus).

Targeting ligands may be attached to the linker arm by any available reactive group that can react with the reactive functional group on the proximal end of the linker arm. For example, peptides and proteins may be attached through an amine, carboxyl, sulfhydryl, or hydroxyl group. Such a group may reside at a peptide terminus or at a site internal to the peptide chain. Nucleic acids may be attached through a reactive group on a base (e.g., exocyclic amine) or an available hydroxyl group on a sugar moiety (e.g., 3'- or 5'-hydroxyl). The peptide or protein may be further derivatized at one or more sites to allow for the attachment of appropriate reactive groups onto the peptide or protein. See, Chrisey et al. Nucleic Acids Res. 24:3031-3039 (1996). In addition, the protein or peptide may be synthesized to contain one or more non-natural amino acids which may then serve as a site for attachment of the linker arm comprising the payload-phosphate-based linker. Antibodies comprising non-natural amino acids for conjugation and methods for making such antibodies have been disclosed in U.S. Pat. No. 7,632,924, which is incorporated herein in its entirety. Examples of non-natural amino acids include but are not limited to para-azido-phenylalanine and para-acetyl-phenylalanine.

Pharmaceutical Formulations and Administration

The conjugates disclosed herein are useful for the manufacture of medicaments for the treatment of diseases or disorders such as an inflammatory disease or cancer. The conjugates disclosed herein may be formulated into pharmaceutical formulations for use in treating diseases or disorders such as an inflammatory disease or cancer.

The present invention provides a pharmaceutical formulation comprising a compound of the invention and a pharmaceutically acceptable carrier. The compounds described herein including pharmaceutically acceptable carriers such as addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

In particular embodiments, the conjugates of the invention comprising an antibody or antibody fragment as the targeting moiety are administered parenterally, more preferably intravenously. As used herein, the terms "administering" or "administration" are intended to encompass all means for directly and indirectly delivering a compound to its intended site of action. The compounds described herein, or pharmaceutically acceptable salts and/or hydrates thereof, may be administered singly, in combination with other compounds of the invention, and/or in cocktails combined with other therapeutic agents. The choice of therapeutic agents that can be co-administered with the compounds of the invention will depend, in part, on the condition being treated.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxyniethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt. The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The following examples are intended to promote a further understanding of the present invention.

Example 1

The synthesis of dexamethasone linker 2-(2-(cycloact-2-yn-1-yloxy)acetamido)ethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (1-4) was as follows.

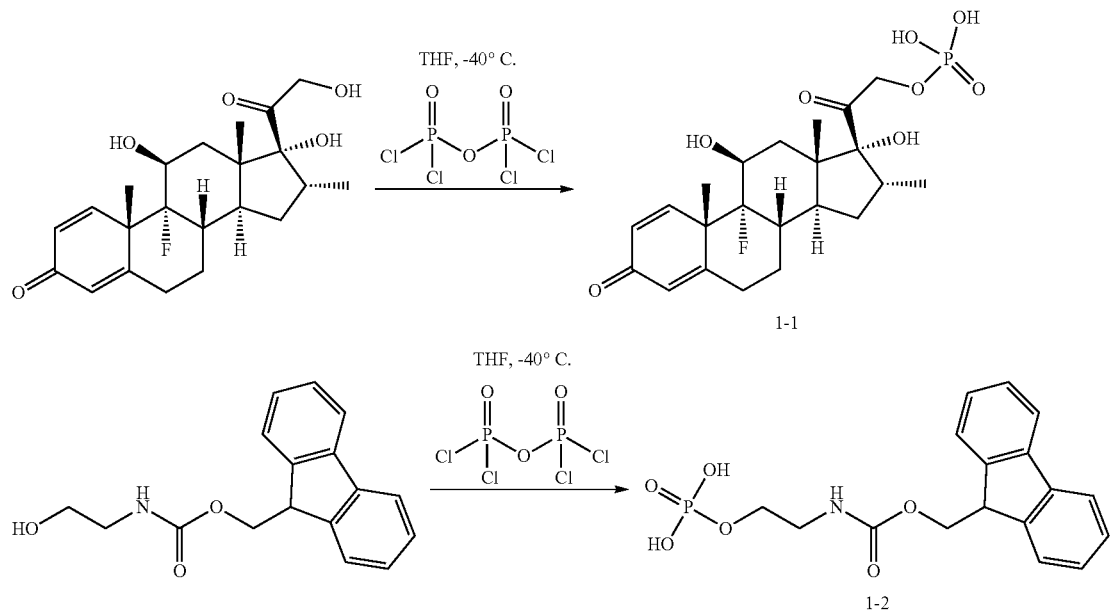
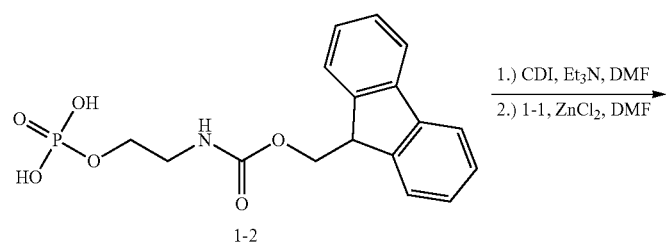
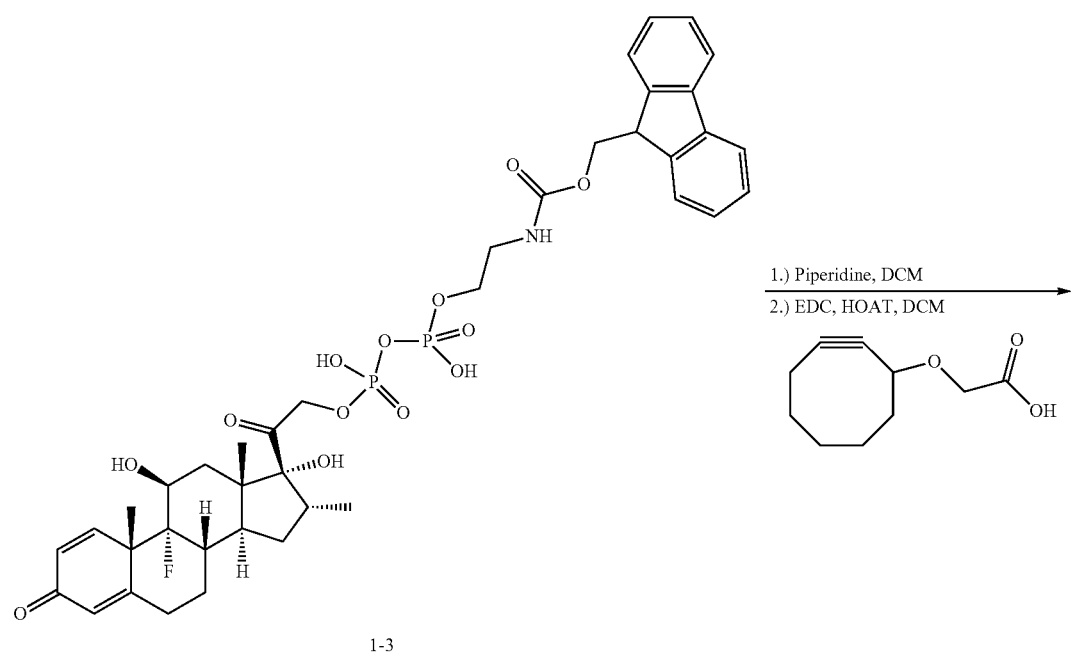

-continued

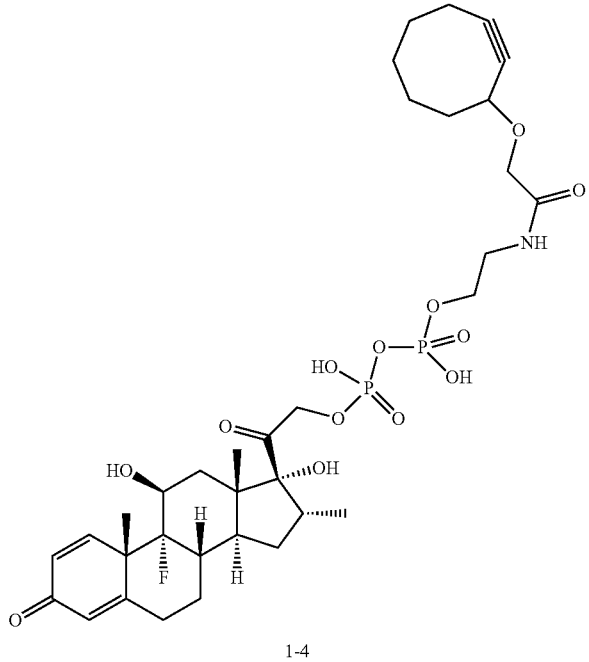

1-4

Step A: 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl dihydrogen phosphate (1-1)

To a stirred solution of dexamethasone (0.40 g, 1.02 mmol) in THF (2.0 mL) at −40° C. was added diphosphoryl chloride (0.31 mL, 2.24 mmol) and the resulting mixture was stirred at −40° C. for 1 hr. The reaction was quenched with water, and treated with saturated sodium bicarbonate solution until pH ~8. The solution was made acidic using 1N HCl solution and extracted several times with ethyl acetate. The combined organic phase washed with brine, dried over sodium sulfate and concentrated to give 1-1 as a solid (497 mg, 103%). LRMS (ES) (M+H)$^+$: observed=473.3, calculated=473.4.

Step B: (9H-fluoren-9-yl)methyl (2-((hydroxy(1H-imidazol-yl)phosphoryl)oxy)ethyl)carbamate (1-2)

The title compound was prepared from N-(9-fluorenyl-methoxycarbonyl)ethanolamine according to the protocol outlined in Example 1-1 to afford 1-2. LRMS (ES) (M+H)$^+$: observed=414.3, calculated=414.4.

Step C: (9H-fluoren-9-yl)methyl (2-(((((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy) phosphoryl)oxy) (hydroxy)phosphoryl)oxy)ethyl) carbamate (1-3)

To a stirred solution of 1-2 (0.15 g, 0.41 mmol) in DMF (1.2 mL) was added triethylamine (0.06 mL, 0.41 mmol) and CDI (0.17 g, 1.03 mmol). The resulting solution was stirred at room temperature for 30 minutes. To this mixture was added 1-1 (0.19 g, 0.41 mmol) and ZnCl$_2$ (0.45 g, 3.31 mmol) and the mixture was allowed to stir at room temperature overnight. The reaction was diluted with 1 N HCl and extracted several times with ethyl acetate. The combined organic layers were concentrated and reverse phase preparative chromatography (Phenomenex Gemini-NX C18 OBD 5 uM 30×100 mm; 5-35% MeCN/water w/0.1% NH$_4$OH modifier over 20 min) gave 1-3 as a solid (134 mg, 40%). LRMS (ES) (M+H)$^+$: observed=818.6, calculated=818.7.

Step D: 2-(2-(cyclooct-2-yn-1-yloxy)acetamido) ethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (1-4)

To a stirred solution of 1-3 (0.19 g, 0.23 mmol) in DCM (3 mL) was added piperidine (0.15 mL, 1.51 mmol) and the resulting mixture was stirred at room temperature for 3 hrs. The solution was concentrated to dryness and redissolved in DCM (2 mL). In a separate vial a stirred solution of 2-(cyclooct-2-yn-1-yloxy)acetic acid (0.045 g, 0.25 mmol) in dichloromethane (1 mL) was added HOAT (0.034 g, 0.25 mmol), EDC (0.056 g, 0.30 mmol) and triethylamine (0.1 mL, 0.68 mmol). The resulting solution was stirred at room temperature for 40 minutes. The two solutions were combined and stirred at room temperature. Additional 2-(cyclooct-2-yn-1-yloxy)acetic acid activated with HOAT/EDC was added as necessary to complete reaction. Upon completion, the mixture was concentrated and reverse phase preparative chromatography (Phenomenex Gemini-NX C18 OBD 5 uM 30×100 mm; 5-30% MeCN/water w/0.1% NH$_4$OH modifier over 20 min) gave 1-4 as a solid (59 mg, 34%). LRMS (ES) (M+H)$^+$: observed=760.6, calculated=760.7. $^1$H NMR (400 MHz, DMSO-d$_6$): δ 8.64 (br s, 1H), 7.29 (d, J=9.15 Hz, 1H), 6.21 (dd, J=10.05, 1.93 Hz, 1H), 6.00 (s, 1H), 4.57 (d, J=8.3 Hz, 2H), 4.31 (t, J=5.4 Hz, 1H), 4.12 (d, J=11.22 Hz, 1H), 3.92 (dd, J=14.43, 8.59 Hz, 1H), 3.80-3.76 (complex, 3H), 3.30-3.16 (complex, 2H), 3.02-2.91 (complex, 2H), 2.63 (m, 1H), 2.40-2.19 (complex, 3H), 2.17-2.03 (complex, 4H), 1.96-1.82 (m, 3H), 1.80-1.72 (complex, 3H), 1.66-1.52 (complex, 4H), 1.50 (s, 3H), 1.40-1.31 (complex, 2H), 1.07-1.02 (m, 1H), 0.88 (s, 3H), 0.77 (d, J=7.17 Hz, 3H)
Example 2
The synthesis of dexamethasone linker 2-(2-(cyclooct-2-yn-1-yloxy)acetamido)ethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) trihydrogen triphosphate (2-7) was as follows.
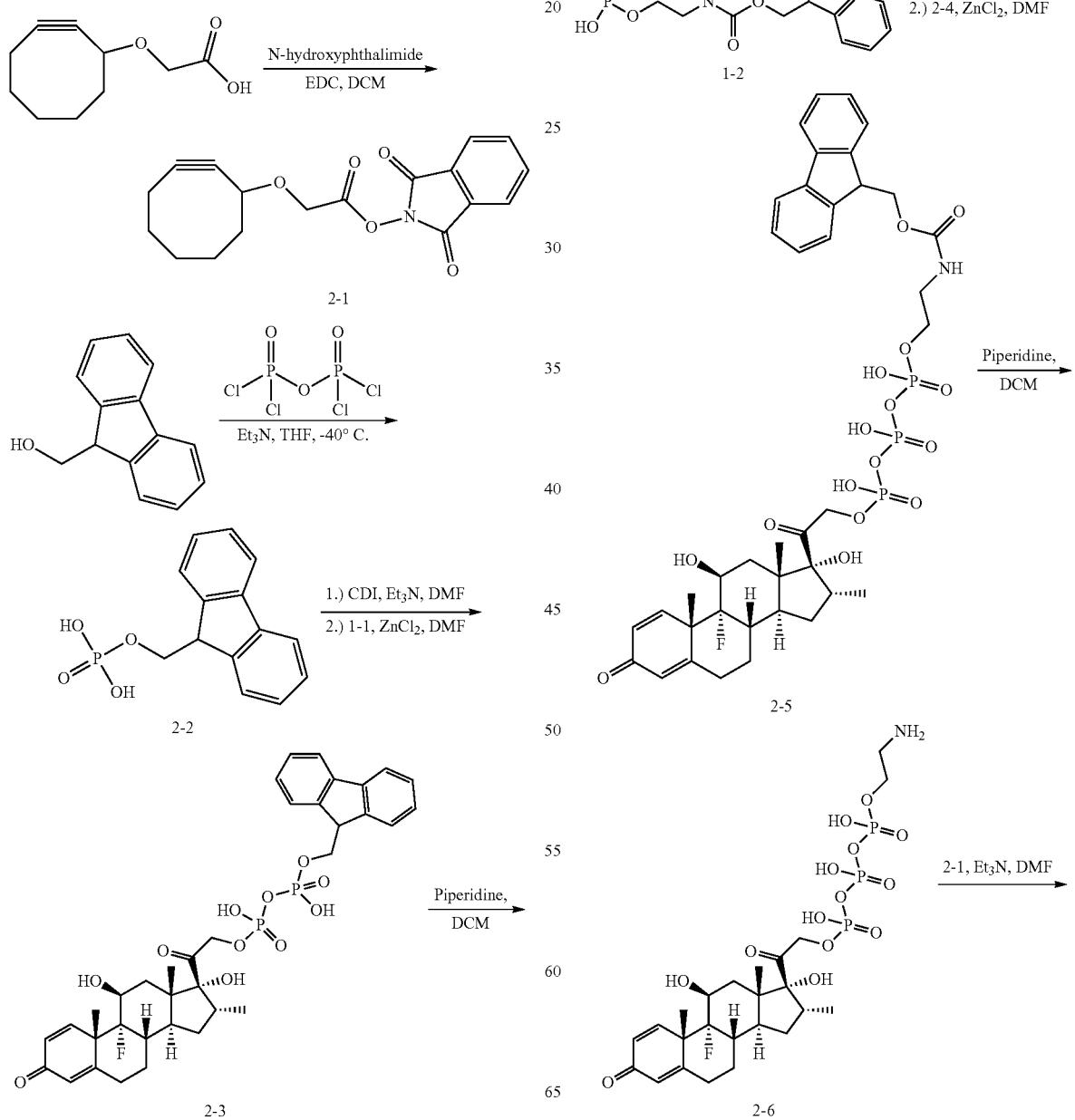

-continued

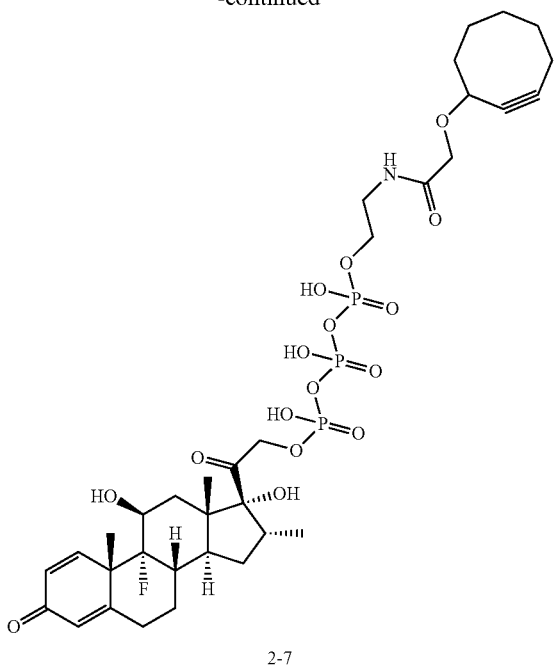

2-7

Step A: 1,3-dioxoisoindolin-2-yl 2-(cyclooct-2-yn-1-yloxy)acetate (2-1)

To a stirred solution of 2-(cyclooct-2-yn-1-yloxy)acetic acid (0.20 g, 1.10 mmol) in DCM (4.0 mL) was added N-hydroxyphthalimide (0.36 g, 2.20 mmol) and EDC (0.42 g, 2.20 mmol). The resulting mixture was stirred at room temperature for 45 minutes. The reaction was directly injected onto a silica gel column and flash column separation using a 0-50% ethyl acetate/hexane gradient gave 2-1 as a solid (335 mg, 93%)

Step B: (9H-fluoren-9-yl)methyl dihydrogen phosphate (2-2)

The title compound was prepared from (9H-fluoren-9-yl)methanol according to the protocol outlined in Example 1-1 to afford 2-2. LRMS (ES) (M+H)$^+$: observed=277.1, calculated=276.2.

Step C: ((9H-fluoren-9-yl)methyl) (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (2-3)

The title compound was prepared from 2-2 and 1-1 according to the protocol outlined in Example 1 to produce 1-3 to afford 2-3. LRMS (ES) (M+H)$^+$: observed=731.2, calculated=730.6.

Step D: 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl trihydrogen diphosphate (2-4)

To a stirred solution of 2-3 (0.29 g, 0.39 mmol) in DCM (2 mL) was added piperidine (0.23 mL, 2.36 mmol) and the resulting mixture was stirred at room temperature for 80 minutes. The solution was concentrated and reverse phase preparative chromatography (Phenomenex Gemini-NX C18 OBD 5 uM 30×100 mm; 3-25% MeCN/water w/0.10% NH$_4$OH modifier over 20 min) gave 2-4 as a solid (123 mg, 56%). LRMS (ES) (M+H)$^+$: observed=553.2, calculated=552.4.

Step E: (9H-fluoren-9-yl)methyl (2-(((((((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy) phosphoryl)oxy) (hydroxy)phosphoryl)oxy) (hydroxy)phosphoryl)oxy)ethyl)carbamate (2-5)

The title compound was prepared from 2-4 and 1-2 according to the protocol outlined in Example 1 to produce 1-3 to afford 2-5. LRMS (ES) (M+H)$^+$: observed=898.3, calculated=897.7.

Step F: 2-aminoethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) trihydrogen triphosphate (2-6)

The title compound was prepared from 2-5 according to the protocol outlined in Example 2 to produce 2-4 to afford 2-6. LRMS (ES) (M+H)$^+$: observed=676.2, calculated=675.4.

Step G: 2-(2-(cyclooct-2-yn-1-yloxy)acetamido)ethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) trihydrogen triphosphate (2-7)

To a stirred solution of 2-6 (0.027 g, 0.04 mmol) in DMF (0.8 mL) was added triethylamine (0.02 mL, 0.16 mmol) and 2-1 and the resulting mixture was stirred at room temperature for 30 minutes. The solution was concentrated and reverse phase preparative chromatography (Phenomenex Gemini-NX C18 OBD 5 uM 30×100 mm; 5-40% MeCN/water w/0.1% NH$_4$OH modifier over 20 min) gave 2-7 as a solid (8 mg, 24%). $^1$H NMR (499 MHz, DMSO): 0.78 (d, J=7.1 Hz, 3H); 0.88 (s, 3H); 1.10-0.99 (complex, 1H); 1.44-1.28 (complex, 2H); 1.50 (s, 3H); 1.67-1.52 (complex, 4H); 1.80-1.67 (complex, 3H); 1.93-1.83 (m, 3H); 2.17-2.01 (complex, 3H); 2.42-2.17 (complex, 3H); 2.67-2.57 (complex, 1H); 2.81 (d, J=79.7 Hz, 1H); 3.02-2.91 (complex, 1H); 3.17 (s, 1H); 3.26-3.21 (complex, 2H); 3.84-3.74 (complex, 2H); 3.91 (d, J=14.5 Hz, 1H); 4.15 (d, J=11.4 Hz, 1H); 4.31 (t, J=5.1 Hz, 1H); 4.57 (dd, J=18.0, 8.1 Hz, 1H); 4.71 (dd, J=17.9, 7.1 Hz, 1H); 5.99 (s, 1H); 6.20 (d, J=10.1 Hz, 1H); 7.30 (d, J=10.6 Hz, 1H); 8.48 (s, 1H). LRMS (ES) (M+H)$^+$: observed=840.4, calculated=839.6.

Example 3

The synthesis of dexamethasone linker 4-(2-(cyclooct-2-yn-1-yloxy)acetamido)phenyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (3-4) was as follows.

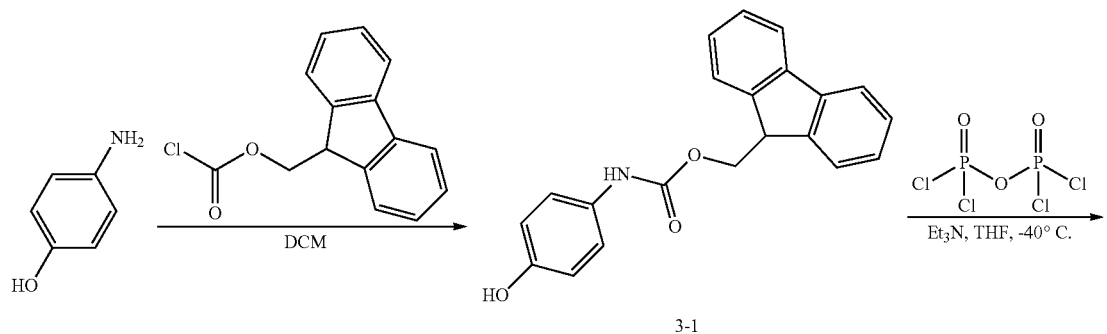
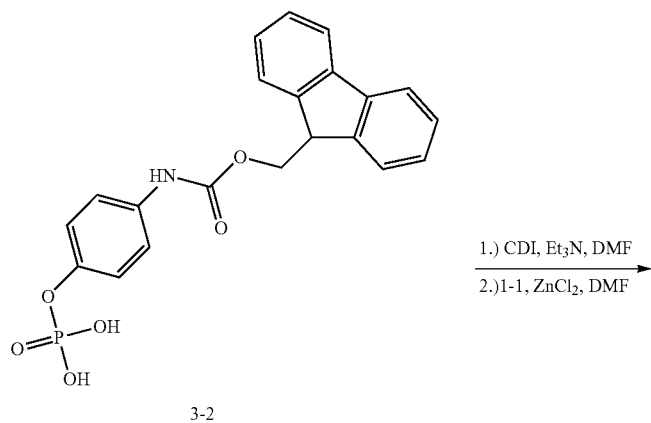
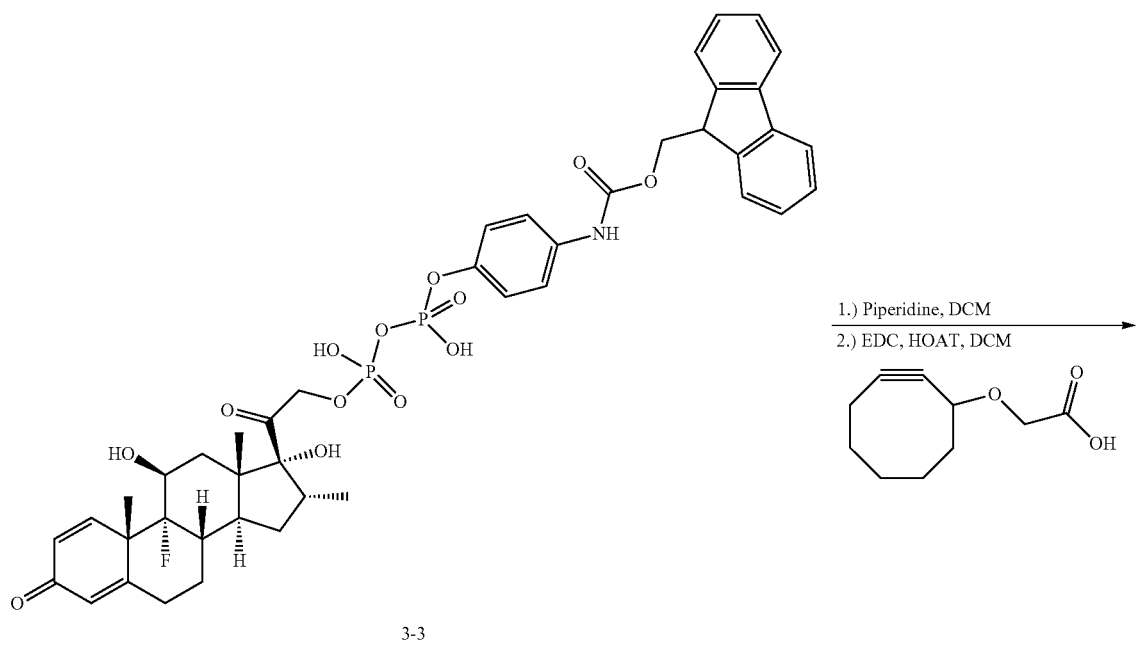

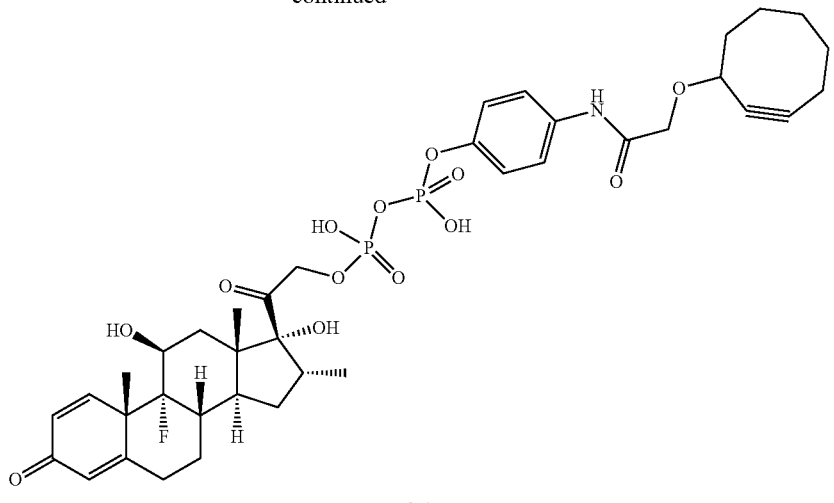

3-4

Step A: (9H-fluoren-9-yl)methyl (4-hydroxyphenyl) carbamate (3-1)

To a stirred solution of 4-aminophenol (0.30 g, 2.75 mmol) in DCM (9 mL) was added (9H-fluoren-9-yl)methyl carbonochloridate (0.71 g, 2.75 mmol) and the resulting mixture was stirred at room temperature for 2 hours. The mixture was partitioned between ethyl acetate and 1 N HCl solution. To the organic phase was added methanol until the solution cleared. The organic phase was dried over sodium sulfate and concentrated onto silica gel and flash column separation using a 100% ethyl acetate gave 3-1 as a solid (634 mg, 70%). LRMS (ES) (M+H)+: observed=332.3, calculated=331.3.

Step B: (9H-fluoren-9-yl)methyl (4-(phosphonooxy) phenyl)carbamate (3-2)

To a stirred solution of 3-1 (0.31 g, 0.95 mmol) in THF (1.9 mL) at −40° C. was added diphosphoryl chloride (0.31 mL, 2.24 mmol) and triethylamine (1.32 mL, 9.51 mmol) and the resulting mixture was stirred at −40° C. for 3 hr. The reaction was quenched with water, and treated with saturated sodium bicarbonate solution until pH ~8. The solution was made acidic using 1N HCl solution and extracted several times with ethyl acetate. The combined organic phase washed with brine, dried over sodium sulfate and concentrated to give 3-2 as a solid (342 mg, 87%). LRMS (ES) (M+H)+: observed=412.3, calculated=411.3.

Step C: (9H-fluoren-9-yl)methyl (4-((((((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a] phenanthren-17-yl)-2-oxoethoxy) (hydroxy) phosphoryl)oxy) (hydroxy)phosphoryl)oxy)phenyl) carbamate (3-3)

The title compound was prepared from 3-2 and 1-1 according to the protocol outlined in Example 1 to produce 1-3 to afford 3-3. LRMS (ES) (M+H)+: observed=866.5, calculated=865.7.

Step D: 4-(2-(cyclooct-2-yn-1-yloxy)acetamido) phenyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (3-4)

The title compound was prepared from 3-3 according to the protocol outlined in Example 1 to produce 1-4 to afford 3-4. LRMS (ES) (M+H)+: observed=808.4, calculated=807.7.

Example 4

The synthesis of dexamethasone linker 2-(2-(cyclooct-2-yn-1-yloxy)acetamido)ethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate (4-3) was as follows.

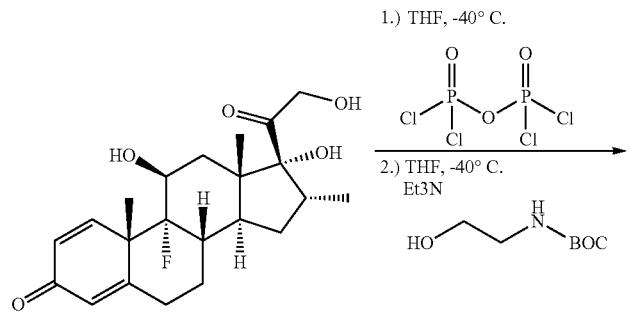

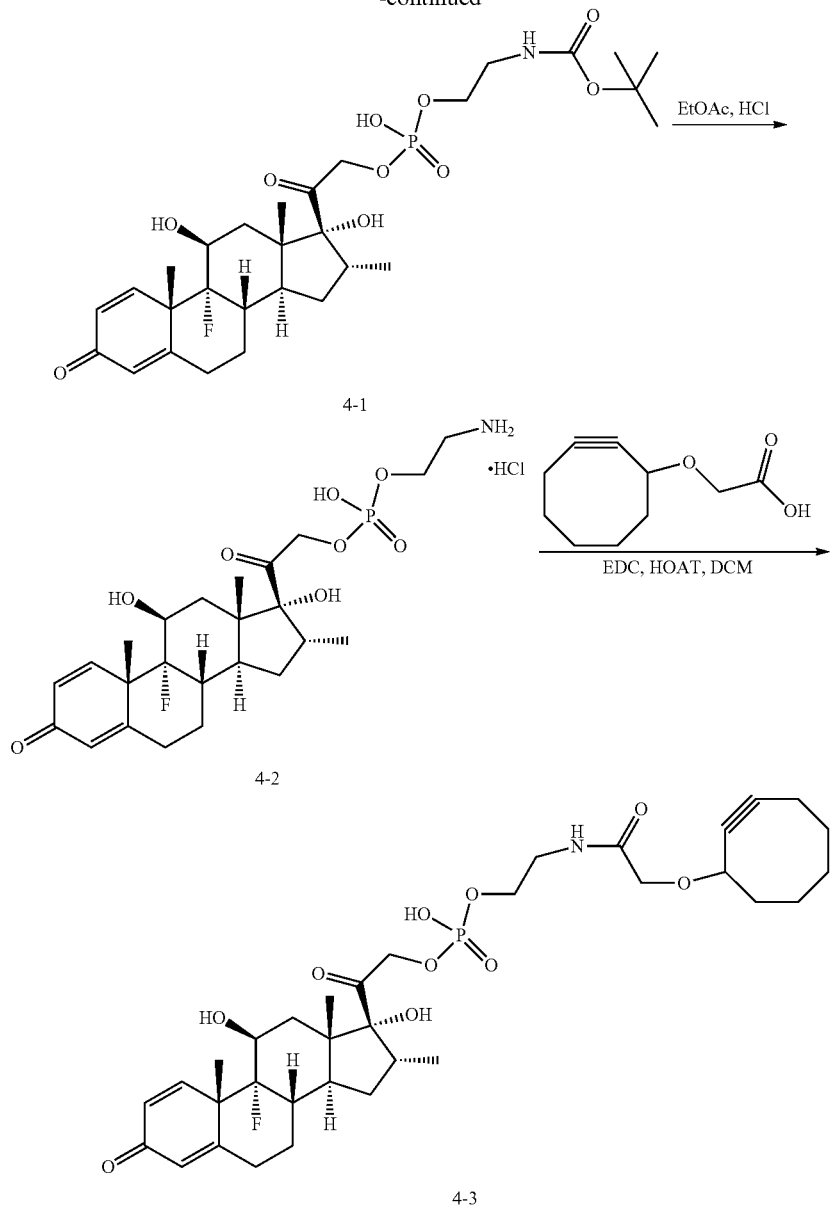

Step A: tert-butyl (2-(((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)(hydroxy)phosphoryl)oxy)ethyl)carbamate (4-1)

To a stirred solution of dexamethasone (0.10 g, 0.26 mmol) in THF (0.5 mL) at −40° C. was added diphosphoryl chloride (0.12 g, 0.48 mmol) and the resulting mixture was stirred at −40° C. for 1 hr. To this was added tert-butyl N-(2-hydroxyethyl)carbamate (0.12 g, 0.76 mmol) and triethylamine (0.14 mL, 1.0 mmol). The resulting mixture was stirred at −40° C. for 4 hr. The reaction was quenched with water, and treated with saturated sodium bicarbonate solution until pH ~8. The solution was made acidic using 1N HCl solution and extracted several times with ethyl acetate. The combined organic phase was concentrated onto silica gel. Flash column separation using a 0-10% isopropanol/dichloromethane gradient gave 4-1 as a solid (115 mg, 73%). LRMS (ES) (M+H)$^+$: observed=616.5, calculated=616.6.

Step B: 2-aminoethyl (2-((8S,9R,10,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate, HCl (4-2)

To a stirred solution of 4-1 (0.11 g, 0.18 mmol) in ethyl acetate (1 mL) at 0° C. was bubbled in HCl gas until saturated. The resulting solution was stirred at 0° C. for 1 hr and concentrated to give 4-2 as a solid (99 mg, 100%). LRMS (ES) (M+H)$^+$: observed=516.4, calculated=516.5.

Step C: 2-(2-(cyclooct-2-yn-1-yloxy)acetamido)
ethyl (2-((8S,9R,10S,11S,13S,14S,16R,17R)-9-
fluoro-11,17-dihydroxy-10,13,16-trimethyl-3-oxo-6,
7,8,9,10,11,12,13,14,15,16,17-dodecahydro-3H-
cyclopenta[a]phenanthren-17-yl)-2-oxoethyl)
hydrogen phosphate (4-3)

To a stirred solution of 2-(cyclooct-2-yn-1-yloxy)acetic acid (0.036 g, 0.20 mmol) in dichloromethane (1 mL) was added HOAT (0.027 g, 0.20 mmol), EDC (0.041 g, 0.22 mmol) and triethylamine (0.05 mL, 0.36 mmol). The resulting solution was stirred at room temperature for 40 minutes. This solution was added to 4-2 (0.10 g, 0.18 mmol) in DCM (1 mL). Additional 2-(cyclooct-2-yn-1-yloxy)acetic acid activated with HOAT/EDC was added as necessary to complete reaction. Upon completion, the mixture was concentrated and reverse phase preparative chromatography (Phenomenex Gemini-NX C18 OBD 5 uM 30×100 mm; 10-50% MeCN/water w/0.1% NH$_4$OH modifier over 20 min) gave 4-3 as a solid (45 mg, 37%). LRMS (ES) (M+H)$^+$: observed=680.6, calculated=680.7. $^1$H NMR (400 MHz, DMSO-d$_6$): δ 8.05 (br t, J=5.6 Hz, 1H), 7.30 (d, J=10.15 Hz, 1H), 6.21 (d, J=10.12 Hz, 1H), 6.00 (s, 1H), 5.55 (s, 1H), 5.37 (s, 1H), 4.70 (dd, J=17.2, 6.7 Hz, 1H), 4.29 (br t, J=6.4 Hz, 1H), 4.18-4.10 (complex, 2H), 3.87 (d, J=14.8 Hz, 1H), 3.74 (d, J=14.8 Hz, 1H), 3.69-3.64 (complex, 2H), 3.27-3.18 (complex, 2H), 2.91 (m, 1H), 2.61 (m, 1H), 2.39-2.05 (complex, 7H), 1.97-1.83 (complex, 2H), 1.80-1.69 (complex, 3H), 1.64-1.52 (complex, 3H), 1.48 (s, 3H), 1.47-1.30 (complex, 3H), 1.05 (m, 1H), 0.85 (s, 3H), 0.76 (d, J=7.13 Hz, 3H).

Example 5

The synthesis of dexamethasone linker 4-(2-(cyclooct-2-yn-1-yloxy)acetamido)phenyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate (5-3) was as follows.

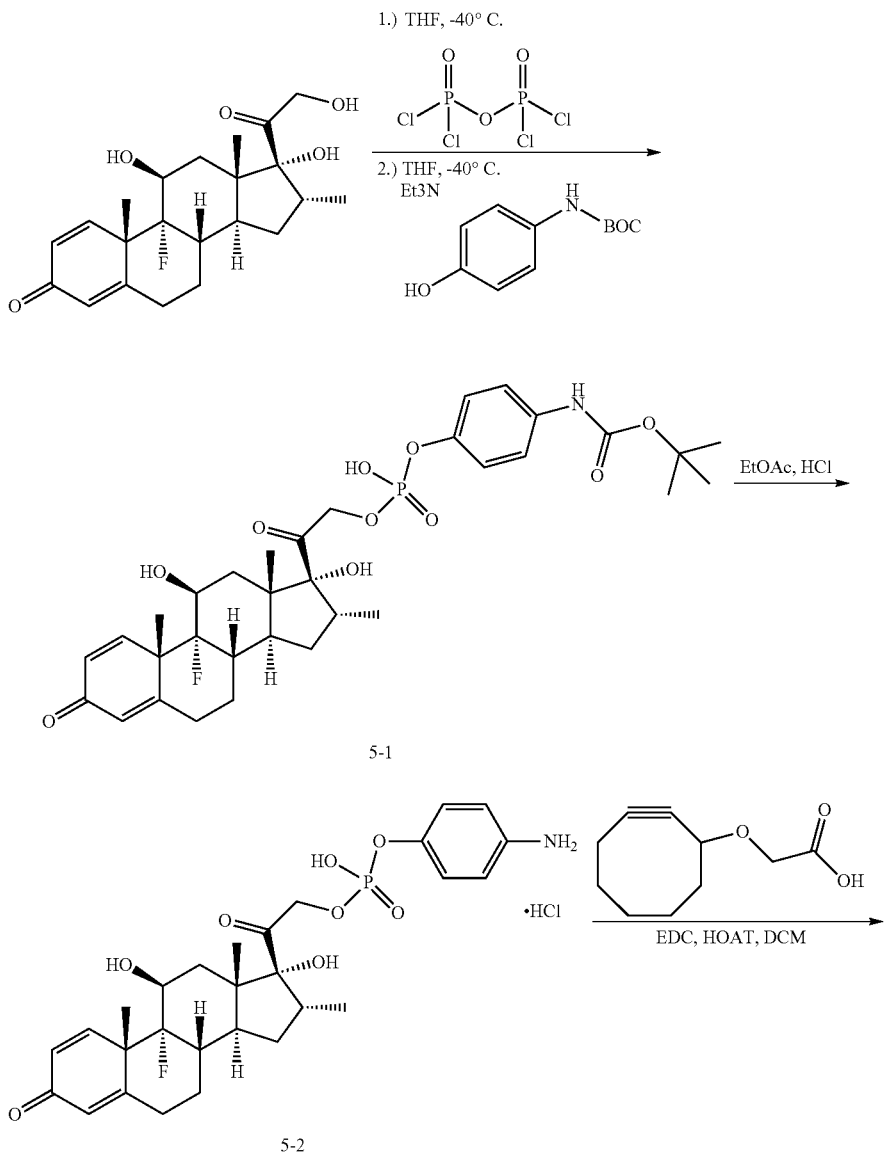

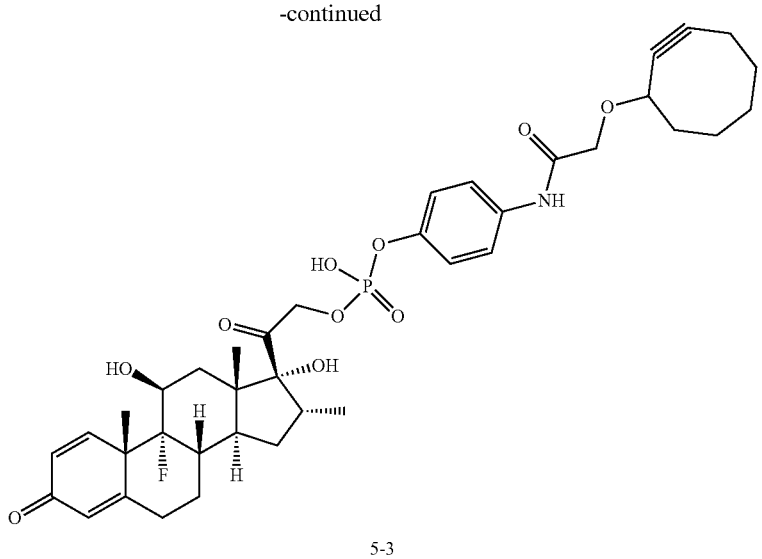

5-3

Step A: tert-butyl (4-(((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy)phosphoryl)oxy)phenyl) carbamate (5-1)

To a stirred solution of dexamethasone (0.20 g, 0.51 mmol) in THF (1.0 mL) at −40° C. was added diphosphoryl chloride (0.24 g, 0.97 mmol) and the resulting mixture was stirred at −40° C. for 1 hr 15 min. To this was added N—BOC-4-aminophenol (0.32 g, 1.53 mmol) and triethylamine (0.56 mL, 4.0 mmol). The resulting mixture was stirred at −40° C. for 30 minutes. The reaction was quenched with water, and treated with saturated sodium bicarbonate solution until pH ~8. The solution was made acidic using 1N HCl solution and extracted several times with ethyl acetate. The combined organic phase was concentrated onto silica gel. Flash column separation using a 0-70% isopropanol/dichloromethane gradient gave 5-1 as a solid (370 mg, 88%). LRMS (ES) (M+H)$^+$: observed=664.5, calculated=664.6.

Step B: 4-aminophenyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate, HCl (5-2)

The title compound was prepared from 5-1 according to the protocol outlined in Example 4 to produce 4-2 to afford 2-2. LRMS (ES) (M+H)$^+$: observed=564.4, calculated=564.5.

Step C: 4-(2-(cyclooct-2-yn-1-yloxy)acetamido)phenyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate (5-3)

The title compound was prepared from 5-2 according to the protocol outlined in Example 4 to produce 4-3 to afford 5-3. LRMS (ES) (M+H)$^+$: observed=728.6, calculated=728.7 $^1$H NMR (400 MHz, DMSO-d$_6$): δ 9.53 (s, 1H), 7.43 (d, J=8.54 Hz, 2H), 7.30 (d, J=10.14 Hz, 1H), 7.04 (d, J=8.54 Hz, 2H), 6.22 (dd, J=10.08, 1.92 Hz, 1H), 6.00 (s, 1H), 5.41 (s, 1H), 5.37 (d, J=4.22 Hz, 1H), 4.78 (dd, J=17.50, 6.20 Hz, 1H), 4.37 (t, J=5.59 Hz, 1H), 4.27 (dd, J=17.47, 9.02, 1H), 4.15-4.12 (m, 1H), 4.06 (d, J=14.53 Hz, 1H), 3.94 (d, J=14.59 Hz, 1H), 3.05 (q, J=7.26 Hz, 1H), 2.92 (m, 1H), 2.61 (m, 1H), 2.40-2.06 (complex, 7H), 1.98 (m, 1H), 1.87 (m, 1H), 1.82-1.73 (complex, 3H), 1.67-1.52 (complex, 3H), 1.48 (s, 3H), 1.43 (d, J=13.54 Hz, 2H), 1.35 (m, 1H), 1.05 (m, 1H), 0.84 (s, 3H), 0.76 (d, J=7.14 Hz, 3H).

Example 6

The synthesis of dexamethasone linker 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl hydrogen (2-(2-(cyclooct-2-yn-1-yloxy)acetamido)ethyl) phosphoramidate (6-2) was as follows.

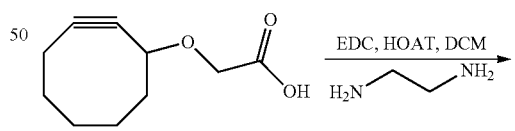

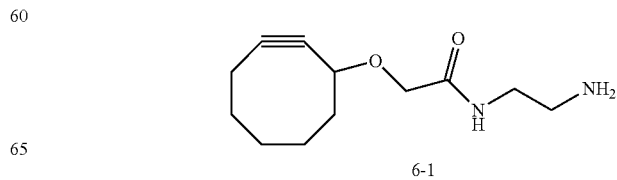

6-1

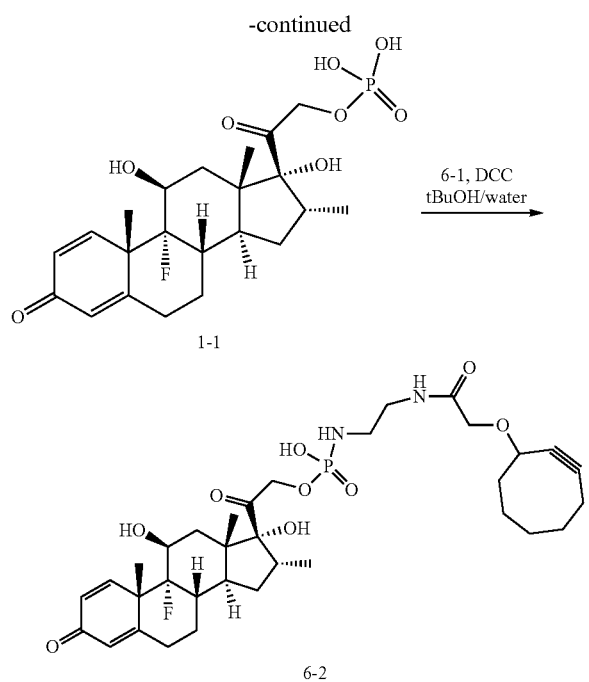

Step A: N-(2-aminoethyl)-2-(cyclooct-2-yn-1-yloxy)acetamide (6-1)

To a stirred solution of 2-(cyclooct-2-yn-1-yloxy)acetic acid (0.10 g, 0.55 mmol) in dichloromethane (2 mL) was added HOAT (0.075 g, 0.55 mmol) and EDC (0.126 g, 0.66 mmol). The resulting solution was stirred at room temperature for 20 minutes. This solution was added to 1,2-ethylenediamine (0.49 g, 8.23 mmol) in DCM (1 mL) dropwise. The mixture was concentrated and purified. (Phenomenex Gemini NX C18, 5 um particle size, 21.2 mm i.d. by 5 cm length, 10-50% CH3CN/water w/0.1% NH4OH modifier over 10 min at 40 mL/min) (50 mg, 40%).

Step B: 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl hydrogen (2-(2-(cyclooct-2-yn-1-yloxy)acetamido)ethyl)phosphoramidate (6-2)

To a stirred solution of 6-1 (0.05 g, 0.22 mmol) and 1-1 (0.035 g, 0.074 mmol) in a solution of t-butanol (1.2 mL) and water (0.25 mL) was added DCC (0.06 g, 0.30 mmol) and the resulting mixture was heated to 100 C for 4 hr. The reaction mixture was allowed to cool and concentrated. The residue was dissolved in a 1:1:1 MeOH:water:MeCN solution and syringe filtered. The mixture was purified using reverse phase preparative chromatography (Phenomenex Gemini-NX C18 OBD 5 uM 30×100 mm; 5-45% MeCN/water w/0.1% NH$_4$OH modifier over 20 min) to give 6-2 as a solid (15 mg, 30%). LRMS (ES) (M+H)$^+$: observed=679.5, calculated=678.7.

Example 7

The synthesis of dexamethasone linker 2-(3-(2,5-dioxo-2,5-dihydro-1H-pyrrol-1-yl)propanamido)ethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (7-1) was as follows.

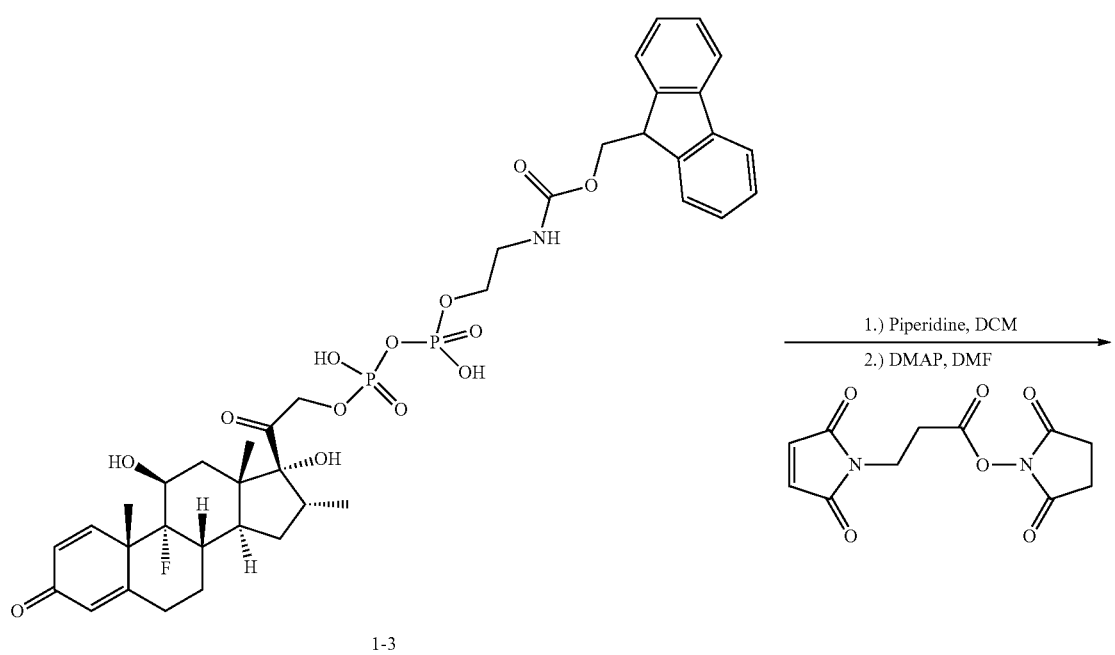

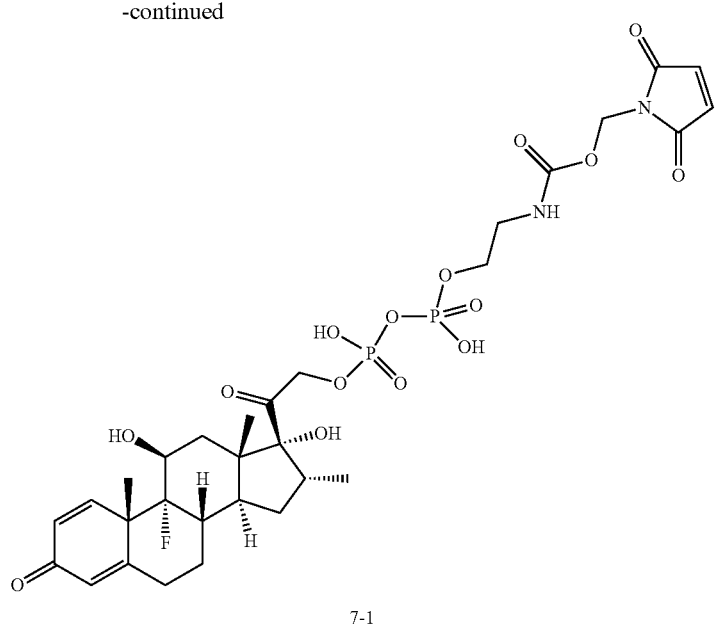

7-1

To a stirred solution of 1-3 (0.19 g, 0.23 mmol) in DCM (3 mL) was added piperidine (0.15 mL, 1.51 mmol) and the resulting mixture was stirred at room temperature for 3 hrs. The solution was concentrated to dryness. The crude mixture was taken into a 2:1:1 methanol:acetonitrile:water mixture and filtered. The filtrate was purified using reverse phase preparative chromatography (Phenomenex Gemini-NX C18 OBD 5 uM 30×100 mm; 5-35% MeCN/water w/0.1% NH$_4$OH modifier over 20 min). A portion of the resulting purified amine (0.07 g, 0.11 mmol) was dissolved in DMF (0.8 mL). To this solution was added 2,5-dioxopyrrolidin-1-yl 3-(2,5-dioxo-2,5-dihydro-1H-pyrrol-1-yl)propanoate (0.09 mg, 0.34 mmol) and DMAP (0.014 g, 0.11 mmol) and the resulting solution was stirred 20 minutes. The crude reaction mixture was directly purified using reverse phase preparative chromatography (Sunfire Prep C18 OBD 5 um 30×150 mm; 10-35% CH3CN/water w/0.1% TFA modifier over 20 min) gave 7-1 as a solid (13 mg, 15%). LRMS (ES) (M+H)$^+$: observed=747.2, calculated=746.6.

Example 8

The synthesis of dexamethasone linker ((2R,3S,4R,5R)-5-(2,4-dioxo-3,4-dihydropyrimidin-1 (2H)-yl)-3-(((2-((8S,9R,10S,11S,13 S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)(hydroxy)phosphoryl)oxy)-4-hydroxytetrahydrofuran-2-yl)methyl (2-(2-(cyclooct-2-yn-1-yloxy)acetamido)ethyl)carbamate (8-5) was as follows.

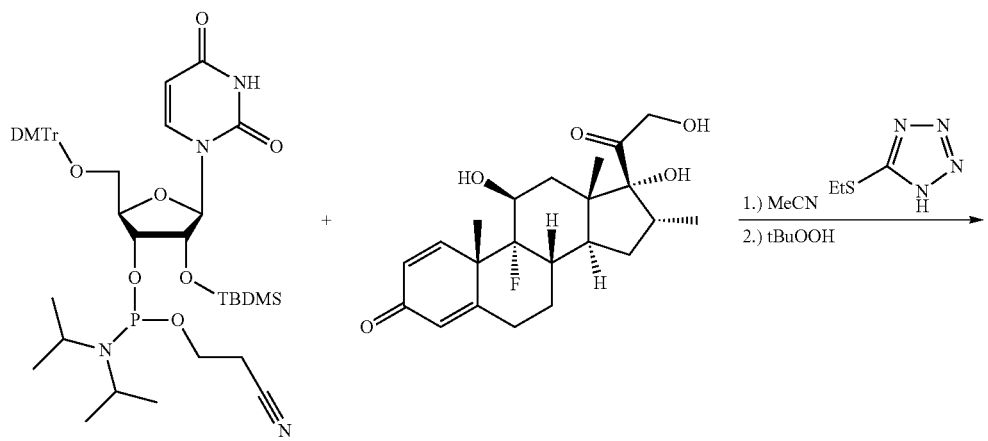

-continued
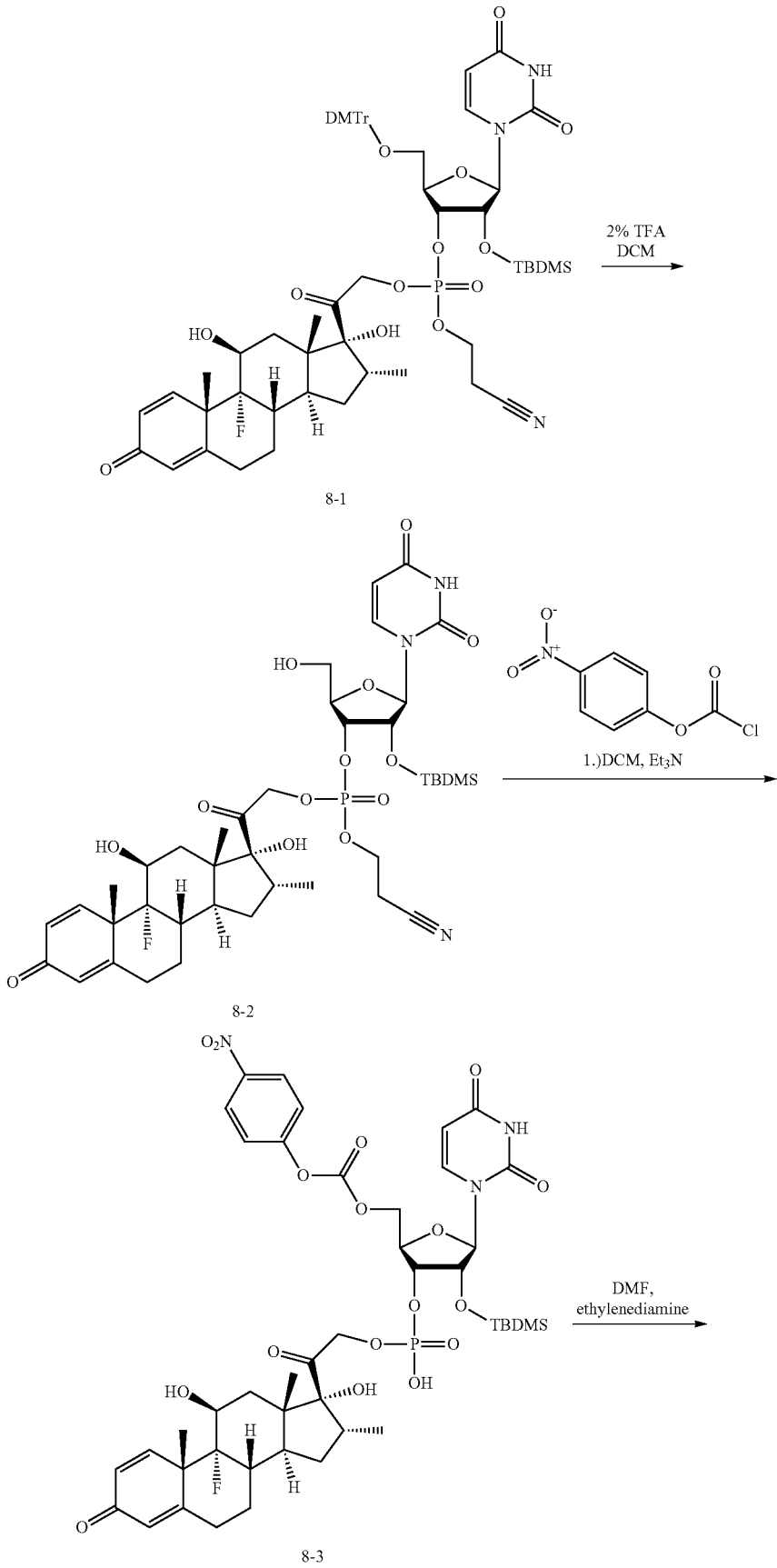

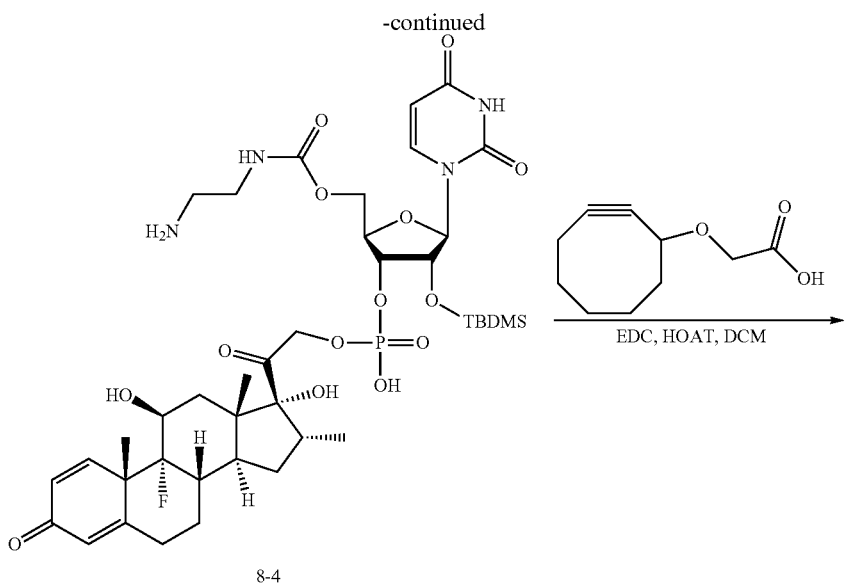

8-4

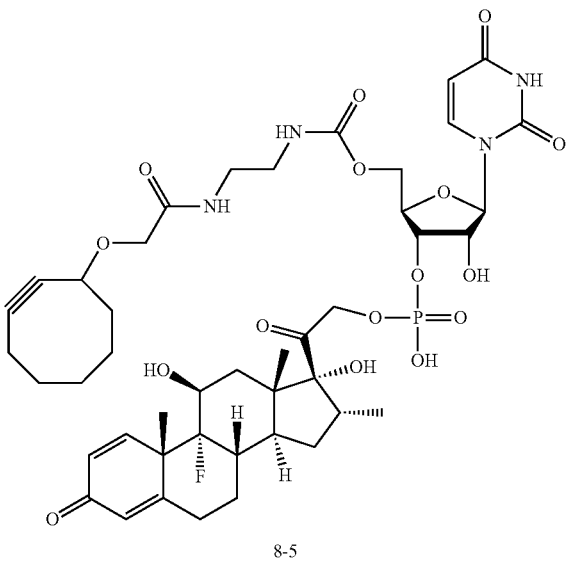

8-5

Step A: (2R,3R,4R,5R)-2-((bis(4-methoxyphenyl)(phenyl)methoxy)methyl)-4-((tert-butyldimethylsilyl)oxy)-5-(2,4-dioxo-3,4-dihydropyrimidin-1(2H)-yl)tetrahydrofuran-3-yl (2-cyanoethyl) (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl)phosphite (8-1)

To a stirred mixture of (2R,3R,4R,5R)-2-((bis(4-methoxyphenyl)(phenyl)methoxy)methyl)-4-((tert-butyldimethylsilyl)oxy)-5-(2,4-dioxo-3,4-dihydropyrimidin-1(2H)-yl)tetrahydrofuran-3-yl (2-cyanoethyl) diisopropylphosphoramidite (1.20 g, 1.40 mmol) and dexamethasone (0.50 g, 1.27 mmol) in acetonitrile (12 mL) was added 5-(ethylthio)-1H-tetrazole (0.33 g, 2.55 mmol). The resulting mixture was stirred for 20 minutes. To the homogenous solution that resulted was added 5M tert-butyl hydroperoxide (0.51 mL, 2.55 mmol). The reaction was stirred 1 hr at room temperature and concentrated onto silica gel. Flash column separation using a 0-100% ethyl acetate/hexane gradient gave 8-1 as a solid (1.67 g, 100%) LRMS (ES) (M+H)+: observed=1168.3, calculated=1168.3.

Step B: (2R,3R,4R,5R)-4-((tert-butyldimethylsilyl)oxy)-5-(2,4-dioxo-3,4-dihydropyrimidin-1 (2H)-yl)-2-(hydroxymethyl)tetrahydrofuran-3-yl (2-cyanoethyl) (2-((8S,9R,10S,11S,13S,14S,16R,1.7R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) phosphate (8-2)

To a stirred solution of 8-1 (1.48 g, 1.26 mmol) in DCM (30 mL) was added TFA (0.3 mL, 3.89 mmol) at room temperature. The reaction was stirred for 30 minutes, washed with saturated bicarbonate solution and the organic phase was concentrated onto silica gel. Flash column separation using a 0-10% isopropanol/DCM gradient gave 8-2 as a solid (0.79 g, 72%) LRMS (ES) (M+H)+: observed=866.5, calculated=865.9.

Step C: ((2R,3R,4R,5R)-4-((tert-butyldimethylsilyl)
oxy)-5-(2,4-dioxo-3,4-dihydropyrimidin-1(2H)-yl)-
3-(((2-((8S,9R,10S,11S,13S,14S,16R,17R)-9-fluoro-
11,17-dihydroxy-10,13,16-trimethyl-3-oxo-6,7,8,9,
10,11,12,13,14,15,16,17-dodecahydro-3H-
cyclopenta[a]phenanthren-17-yl)-2-oxoethoxy)
(hydroxy)phosphoryl)oxy)tetrahydrofuran-2-yl)
methyl (4-nitrophenyl) carbonate (8-3)

To a stirred solution of 8-2 (0.30 g, 0.35 mmol) in DCM (5 mL) was added triethylamine (0.15 mL, 1.04 mmol) and 4-nitrophenyl carbonochloridate (0.15 g, 0.76 mmol) and the resulting solution was stirred at room temperature. Additional 4-nitrophenyl carbonochloridate was added until reaction was complete by LCMS. The reaction was directly loaded onto a silica gel column and flash column separation using a 0-50% isopropanol/DCM gradient gave 8-3 as a solid (0.32 g, 93%) LRMS (ES) (M+H)$^+$: observed=978.4, calculated=977.9.

Step D: ((2R,3R,4R,5R)-4-((tert-butyldimethylsilyl)
oxy)-5-(2,4-dioxo-3,4-dihydropyrimidin-1(2H)-yl)-
3-(((2-((8S,9R,10S,11S,13S,14S,16R,17R)-9-fluoro-
11,17-dihydroxy-10,13,16-trimethyl-3-oxo-6,7,8,9,
10,11,12,13,14,15,16,17-dodecahydro-3H-
cyclopenta[a]phenanthren-17-yl)-2-oxoethoxy)
(hydroxy)phosphoryl)oxy)tetrahydrofuran-2-yl)
methyl (2-aminoethyl)carbamate (8-4)

To a stirred solution of ethylenediamine (0.28 mL, 4.17 mmol) in DMF (1 mL) was added a solution of 8-3 (0.20 g, 0.20 mmol) in DMF (1 mL) dropwise. The reaction was stirred at room temperature for 10 minutes, then purified directly using reverse phase preparative chromatography (Phenomenex Gemini-NX C18 OBD 5 uM 30×100 mm; 10-50% MeCN/water w/0.1% NH$_4$OH modifier over 20 min) to give 8-4 as a solid (115 mg, 61%). LRMS (ES) (M+H)$^+$: observed=899.5, calculated=898.9.

Step E: ((2R,3S,4R,5R)-5-(2,4-dioxo-3,4-dihydro-
pyrimidin-1 (2H)-yl)-3-(((2-((8S,9R,10S,11S,13S,
14S,16R,17R)-9-fluoro-11,17-dihydroxy-10,13,16-
trimethyl-3-oxo-6,7,8,9,10,11,12,13,14,15,16,17-
dodecahydro-3H-cyclopenta[a]phenanthren-17-yl)-
2-oxoethoxy) (hydroxy)phosphoryl)oxy)-4-
hydroxytetrahydrofuran-2-yl)methyl (2-(2-(cyclooct-
2-yn-1-yloxy)acetamido)ethyl)carbamate (8-5)

The title compound was prepared from 8-4 according to the protocol outlined in Example 4 to produce 4-3 to afford 8-5. LRMS (ES) (M+H)$^+$: observed=949.4, calculated=948.9.

Example 9

The synthesis of Budesonide linker 2-(2-(cyclooct-2-yn-1-yloxy)acetamido)ethyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (9-4) was as follows.

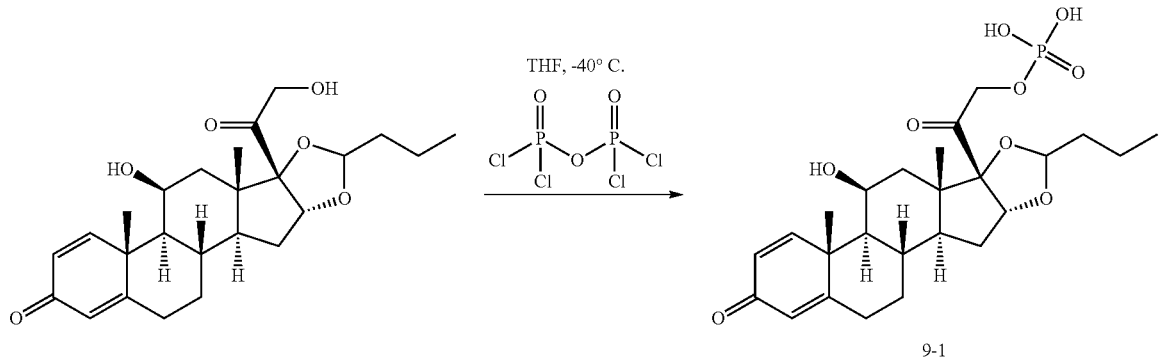

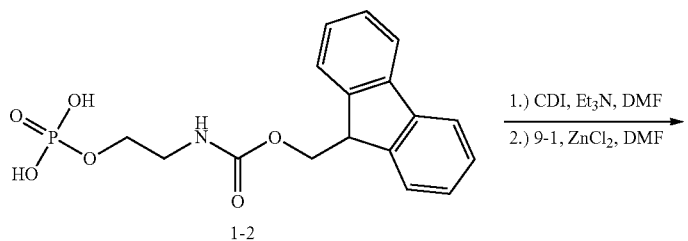

-continued
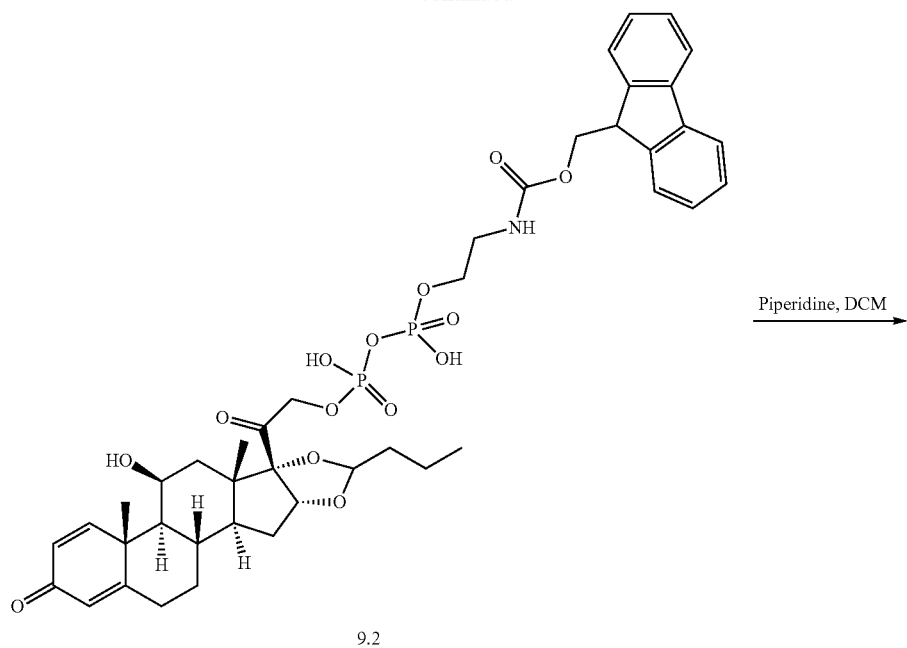
9.2
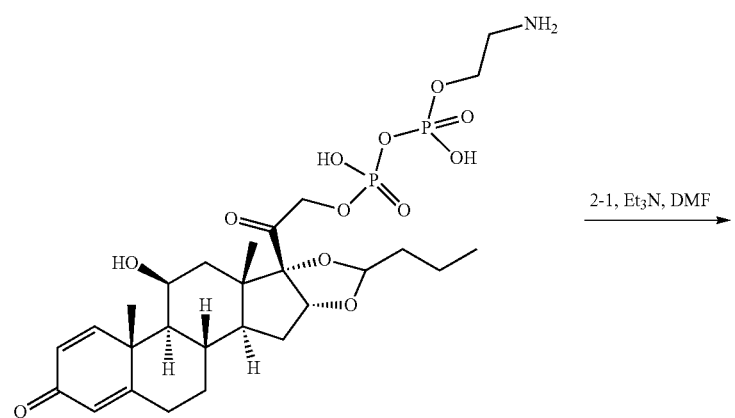
9-3

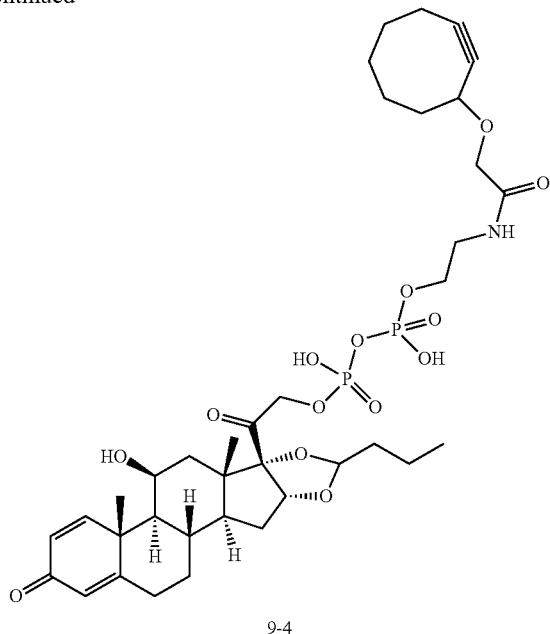

9-4

Step A: 2-((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a, 12b-dodecahydro-1H-naphtho[2',1':4,5]indeno[1,2-d][1,3]dioxol-8b-yl)-2-oxoethyl dihydrogen phosphate (9-1)

The title compound was prepared from budesonide according to the protocol outlined in Example 1 to produce 1-1 to afford 9-1. LRMS (ES) (M+H)⁺: observed=511.2, calculated=510.5.

Step B: (9H-fluoren-9-yl)methyl (2-((hydroxy((hydroxy(2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethoxy)phosphoryl)oxy)phosphoryl)oxy)ethyl)carbamate (9-2)

The title compound was prepared from 9-1 according to the protocol outlined in Example 1 to produce 1-3 to afford 9-2. LRMS (ES) (M+H)⁺: observed=856.3, calculated=855.8.

Step C: 2-aminoethyl (2-((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (9-3)

The title compound was prepared from 9-2 according to the protocol outlined in Example 2 to produce 2-6 to afford 9-3. LRMS (ES) (M+H)⁺: observed=634.3, calculated=633.5.

Step D: 2-(2-(cyclooct-2-yn-1-yloxy)acetamido)ethyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (9-4)

The title compound was prepared from 9-3 according to the protocol outlined in Example 2-7 to afford 9-4. Mixture of isomers $^1$H NMR (499 MHz, DMSO): 0.86-0.83 (complex, 6H); 0.89 (s, 6H); 0.99-0.90 (complex, 2H); 1.09 (t, J=7.0 Hz, 2H); 1.15 (t, J=7.2 Hz, 6H); 1.35-1.25 (complex, 6H); 1.39 (s, 6H); 2.32-1.46 (complex, 32H); 3.02 (q, J=7.0 Hz, 4H); 3.21 (br s, 2H); 3.81-3.73 (complex, 6H); 3.94-3.89 (complex, 2H); 4.33-4.25 (complex, 4H); 4.39 (d, J=18.4 Hz, 2H); 4.56 (t, J=4.3 Hz, 1H); 4.79-4.63 (complex, 3H); 5.01 (d, J=7.2 Hz, 1H); 5.17 (dd, J=4.9, 4.6 Hz, 1H); 5.91 (s, 2H); 6.15 (d, J=10.1 Hz, 2H); 7.31 (d, J=10.3 Hz, 2H); 8.84 (br s, 2H). LRMS (ES) (M+H)⁺: observed=798.4, calculated=797.7.

Example 10

The synthesis of Budesonide linker 2-(3-(2,5-dioxo-2,5-dihydro-1H-pyrrol-1-yl)propanamido)ethyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (10-1) was as follows.

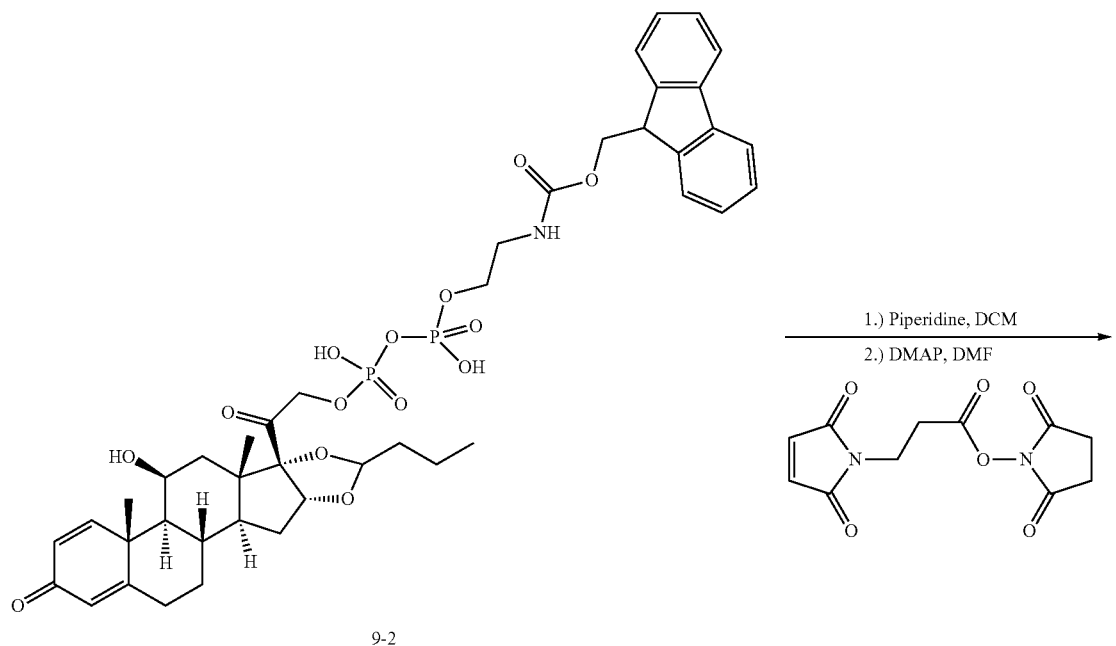
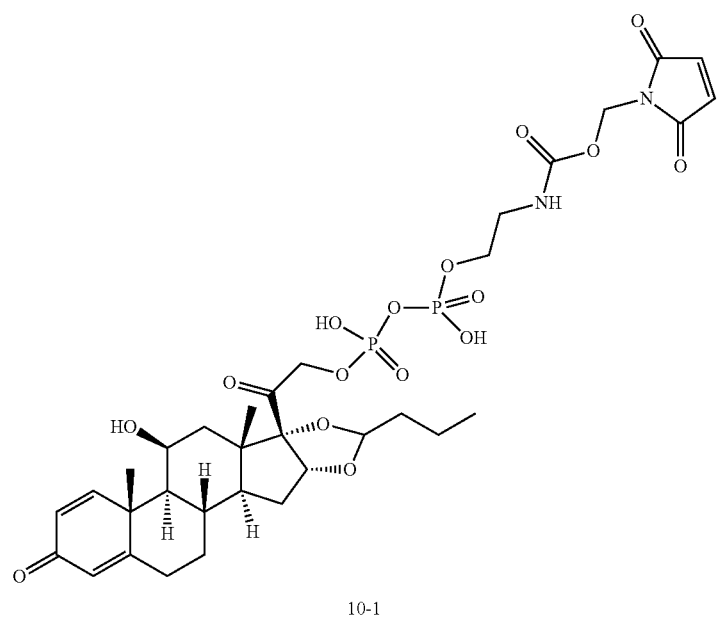
The title compound was prepared from 9-2 according to the protocol outlined in Example 7 to produce 7-1 to afford 10-1. LRMS (ES) (M+H)+: observed=785.4, calculated=784.6.

Example 11
The synthesis of Budesonide linker 1-(cyclooct-2-yn-1-yloxy)-2-oxo-6,9,12-trioxa-3-azatetradecan-14-yl (2-((6aR,6bS,7S,8aS,8bS,11aR,12aS,12bS)-7-hydroxy-6a,8a-dimethyl-4-oxo-10-propyl-2,4,6a,6b,7,8,8a,8a,8b, 11a,12,12a,12b-dodecahydro-1H-naphtho[2',1':4,5]indeno[1,2-d][1,3]dioxol-8b-yl)-2-oxoethyl) dihydrogen pyrophosphate (11-5) was as follows.
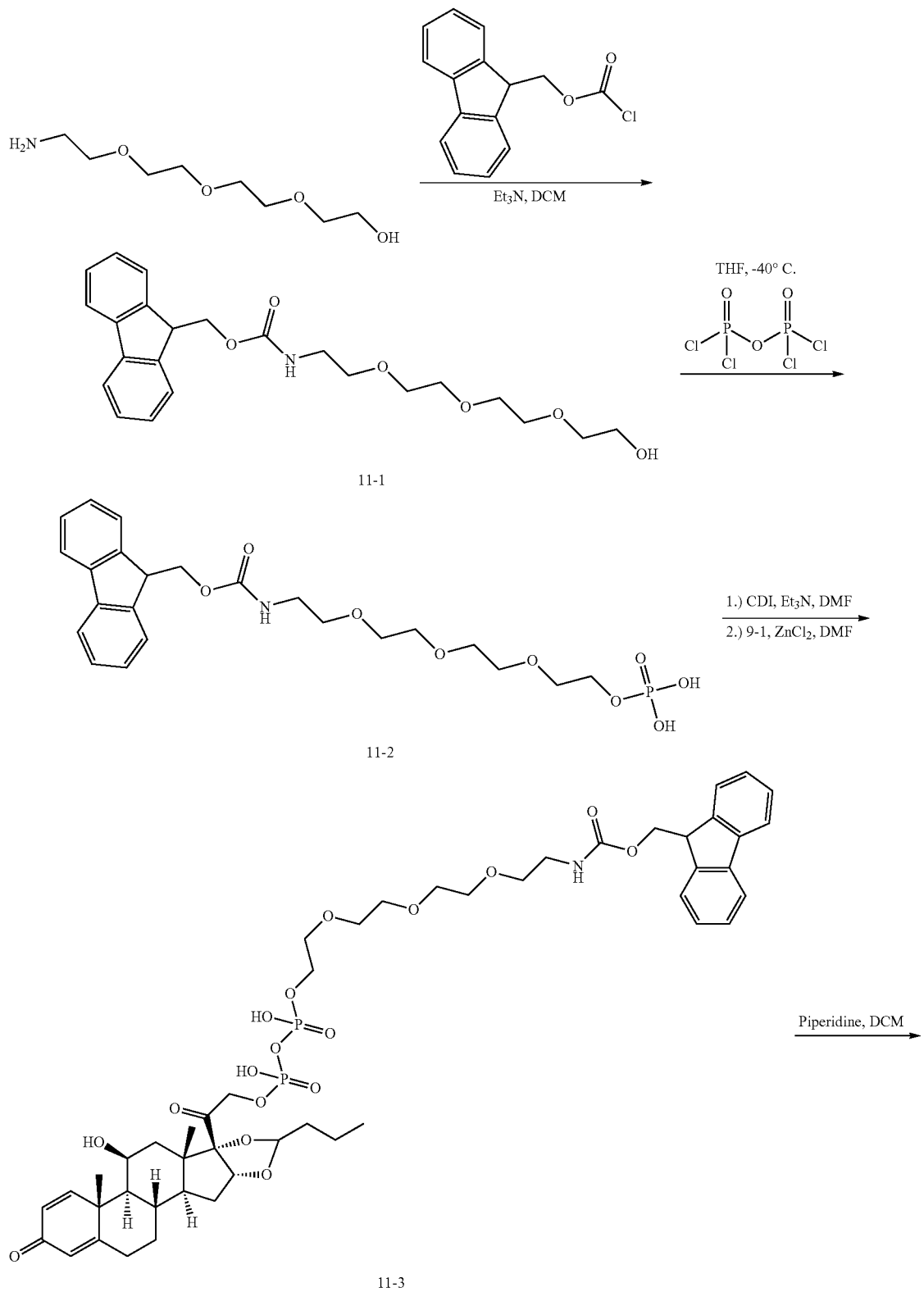

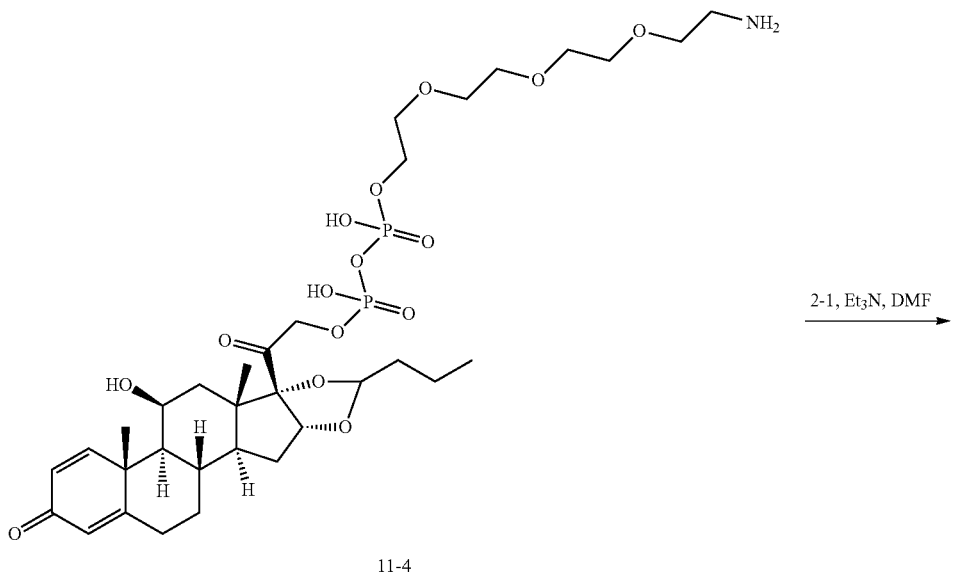
11-4
2-1, Et₃N, DMF
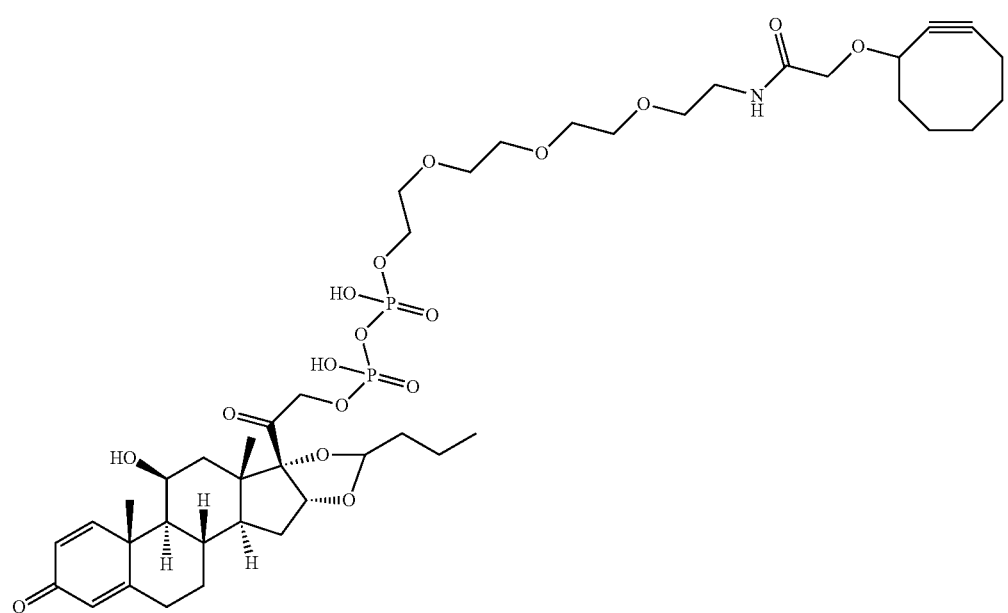
11-5

Step A: (9H-fluoren-9-yl)methyl (2-(2-(2-(2-hydroxyethoxy)ethoxy)ethoxy)ethyl)carbamate (11-1)

To a stirred solution of 2-(2-(2-(2-aminoethoxy) ethoxy)ethanol (1.00 g, 5.17 mmol) in DCM (15 mL) was added 9-fluorenylmethyl chloroformate (1.34 g, 5.17 mmol) and triethylamine (1.08 mL, 7.76 mmol). The resulting solution was stirred at room temperature for 10 minutes. The reaction was concentrated onto silica gel and flash column separation using a 0-10% isopropanol/dichloromethane gradient gave 11-1 as an oil (1.43 g, 66%) LRMS (ES) (M+H)$^+$ observed=416.1, calculated=415.4.

Step B. (9H-fluoren-9-yl)methyl (2-(2-(2-(2-(phosphonooxy)ethoxy)ethoxy)ethoxy)ethyl)carbamate (11-2)

The title compound was prepared from 11-1 according to the protocol outlined in Example 1 to produce 1-1 to afford 11-2. LRMS (ES) (M+H)$^+$ observed=496.3, calculated=495.4.

Step C: (9H-fluoren-9-yl)methyl (2-(2-(2-(2-((hydroxy((hydroxy(2-(((6aR,6bS,7S,8aS,8bS,11aR,12aS,2bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethoxy)phosphoryl)oxy)phosphoryl)oxy)ethoxy)ethoxy)ethoxy)ethyl)carbamate (11-3)

The title compound was prepared from 11-2 and 9-1 according to the protocol outlined in Example 1 to produce 1-3 to afford 11-3. LRMS (ES) (M+H)$^+$: observed=988.6, calculated=987.9.

Step D: 2-(2-(2-(2-aminoethoxy)ethoxy)ethoxy)ethyl (2-((6aR,6bS,7S,8aS,8bS,11aR,12aS,12bS)-7-hydroxy-6a,8a-dimethyl-4-oxo-10-propyl-2,4,6a,6b,7,8,8a, 8b,11a,12,12a,12b-dodecahydro-1H-naphtho[2',1': 4,5]indeno[1,2-d][1,3]dioxol-8b-yl)-2-oxoethyl) dihydrogen pyrophosphate (11-4)

The title compound was prepared from 11-3 according to the protocol outlined in Example 2 to produce 2-6 to afford 11-4. LRMS (ES) (M+H)$^+$: observed=766.5, calculated=765.7.

Step E: 1-(cyclooct-2-yn-1-yloxy)-2-oxo-6,9,12-trioxa-3-azatetradecan-14-yl (2-((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (11-5)

The title compound was prepared from 11-4 according to the protocol outlined in Example 2 to produce 2-7 to afford 11-5. LRMS (ES) (M+H)$^+$: observed=930.6, calculated=929.9.

Example 12

The synthesis of Budesonide linker 4-((2S)-2-((2S)-2-(2-(cyclooct-2-yn-1-yloxy)acetamido)-3-methylbutanamido)-5-ureidopentanamido)benzyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a, 12b-dodecahydro-1H-naphtho[2',1':4,5]indeno[1,2-d][1,3]dioxol-8b-yl)-2-oxoethyl) hydrogen phosphate (12-3) was as follows.

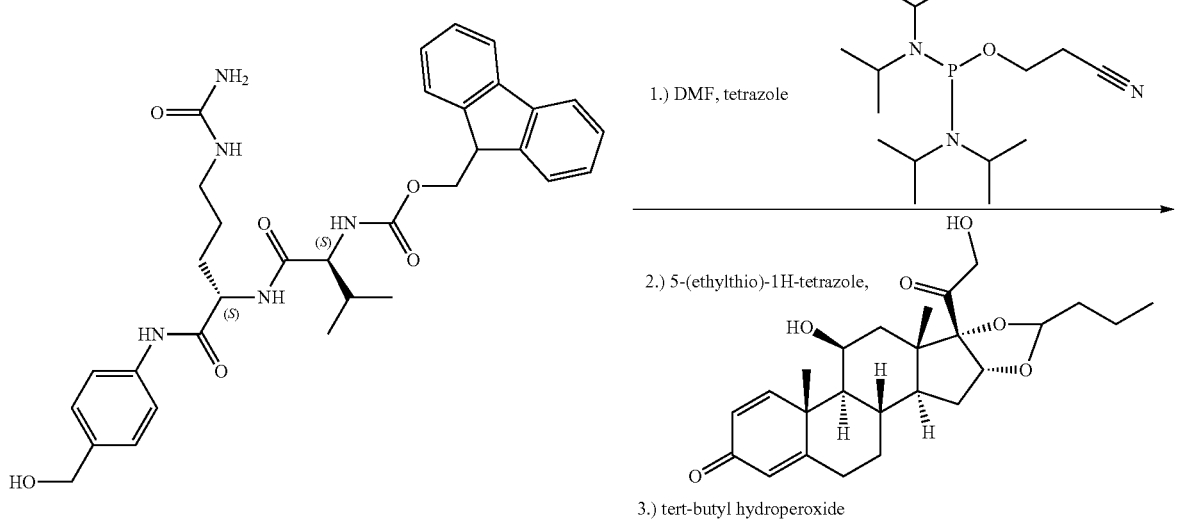

-continued
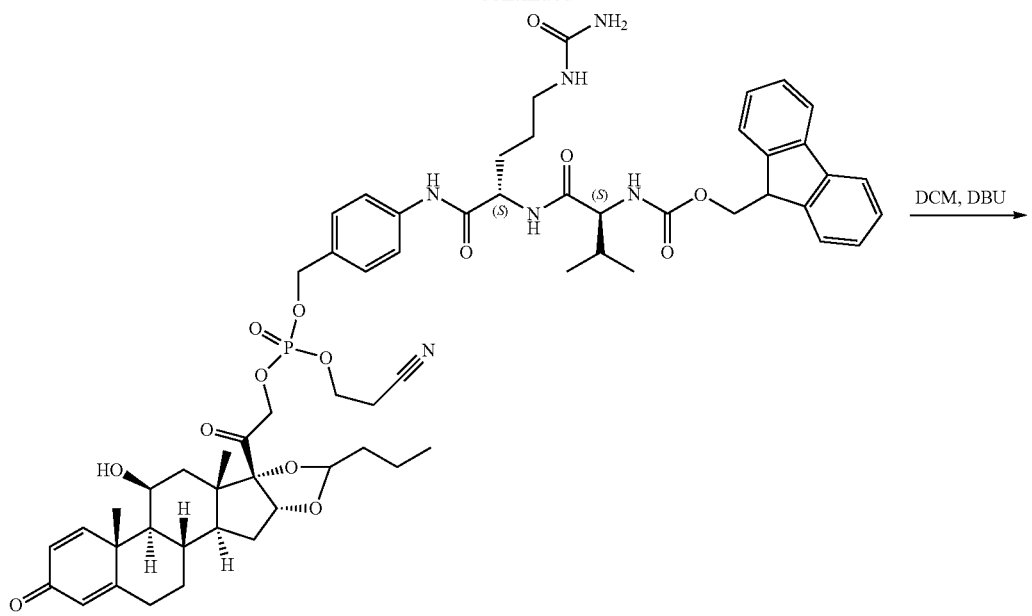
12-1
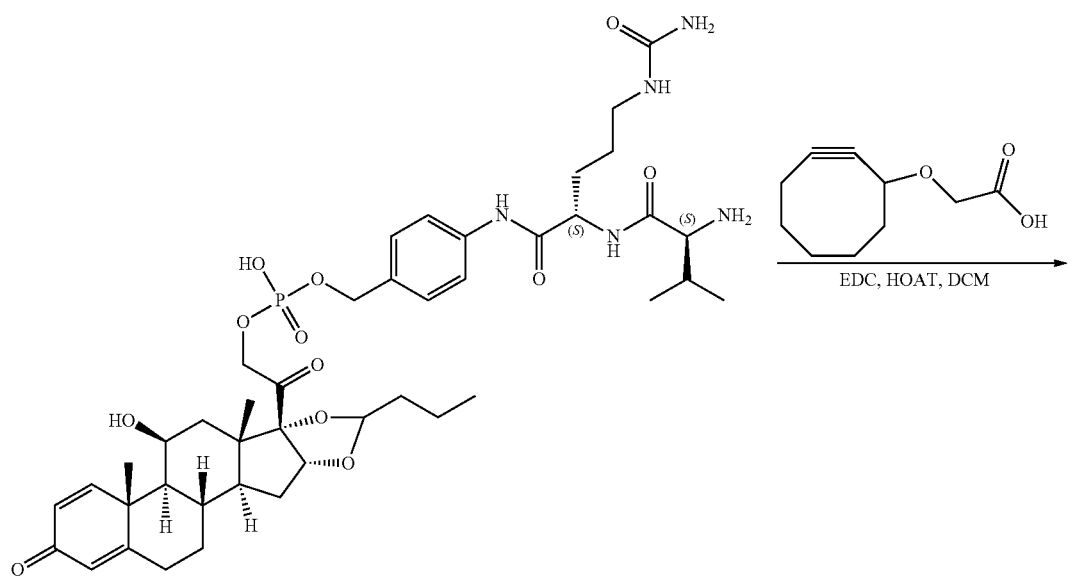
12-2

-continued

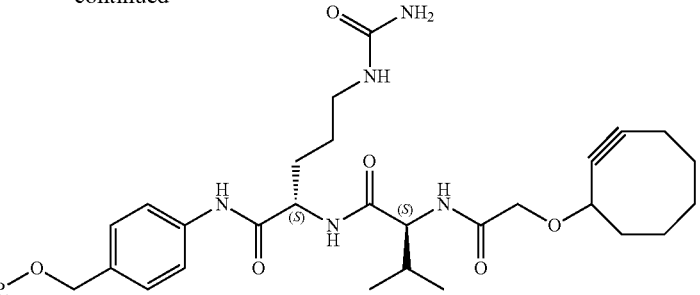
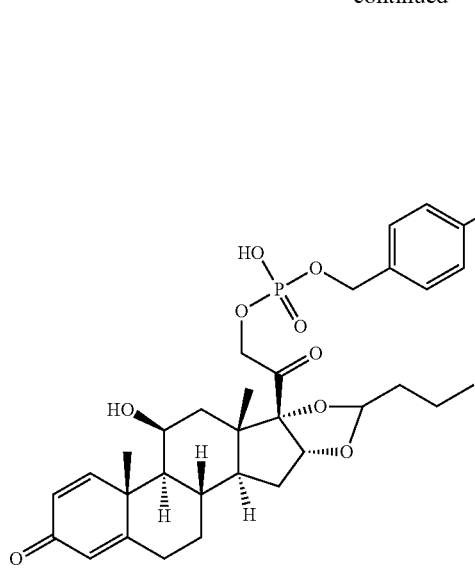

12-3

Step A: (9H-fluoren-9-yl)methyl ((2S)-1-(((2S)-1-((4-(((((2-cyanoethoxy) (2 ((6aR,6bS,7S,8aS,8bS,11aR,12aS,12bS)-7-hydroxy-6a, 8a-dimethyl-4-oxo-10-propyl-2,4,6a,6b,7,8,8a, 8b,11a, 12,12a,12b-dodecahydro-1H-naphtho[2',1':4,5]indeno[1,2-d][1,3]dioxol-8b-yl)-2-oxoethoxy)phosphoryl)oxy) methyl)phenyl)amino)-1-oxo-5-ureidopentan-2-yl) amino)-3-methyl-1-oxobutan-2-yl)carbamate (12-1)

To a stirred solution of (9H-fluoren-9-yl)methyl ((S)-1-(((S)-1-((4-(hydroxymethyl)phenyl)amino)-1-oxo-5-ureidopentan-2-yl)amino)-3-methyl-1-oxobutan-2-yl)carbamate (0.20 g, 0.33 mmol) in DMF (4.7 mL) was added 3-((bis (diisopropylamino)phosphino)oxy)propanenitrile (0.11 g, 0.37 mmol). To this mixture was added 0.45M tetrazole in acetonitrile (0.81 mL, 0.37 mmol) dropwise and the resulting mixture was stirred for 20 minutes at room temperature. To this was added Budesonide (0.22 g, 0.50 mmol) and 5-(ethylthio)-1H-tetrazole (0.09 g, 0.67 mmol) and allowed to stir to 30 minutes at room temperature. To this was added 6 M tertbutyl hydroperoxide in decane (0.12 mL, 0.73 mmol) and allowed to stir at room temperature for 1 hour. The crude reaction was loaded directly onto silica gel and flash column separation using a 0-100% ethyl acetate/hexane gradient followed by a 0-50% isopropanol/DCM gradient gave 12-1 as a solid. (0.10 g, 27%) LRMS (ES) (M+H)+: observed=1147.7, calculated=1147.2.

Step B: 4-((S)-2-((S)-2-amino-3-methylbutanamido)-5-ureidopentanamido)benzyl (2((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1'4,5]indeno[1,2-d][1,3]dioxol-8b-yl)-2-oxoethyl) hydrogen phosphate (12-2)

To a stirred solution of 12-1 (0.10 g, 0.09 mmol) in DCM (1.8 mL) was added DBU (0.05 mL, 0.35 mmol) and the resulting solution was stirred 20 minutes at room temperature. The reaction was concentrated and dissolved in a 2:1:1 methanol:water:acetonitrile mixture and syringe filtered. The filtrate was purified using reverse phase preparative chromatography (Phenomenex Gemini-NX C18 OBD 5 uM 30×100 mm; 10-50% MeCN/water w/0.1% $NH_4OH$ modifier over 20 min) to give 12-2 as a solid (42 mg, 53%). LRMS (ES) (M+H)+: observed=872.6, calculated=871.9.

Step C: 4-((2S)-2-((2S)-2-(2-(cyclooct-2-yn-1-yloxy)acetamido)-3-methylbutanamido)-5-ureidopentanamido) benzyl (2-((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) hydrogen phosphate (12-3)

The title compound was prepared from 12-2 according to the protocol outlined in Example 4 to produce 4-3 to afford 12-3. LRMS (ES) (M+H)+: observed=1036.8, calculated=1036.1.

Example 13

The synthesis of Budesonide linker 2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-1) was as follows.

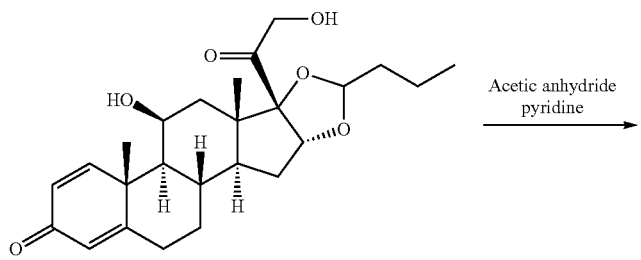
Acetic anhydride pyridine →
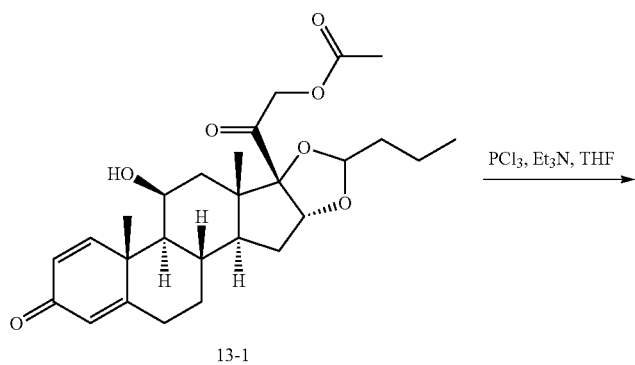
13-1
PCl₃, Et₃N, THF →
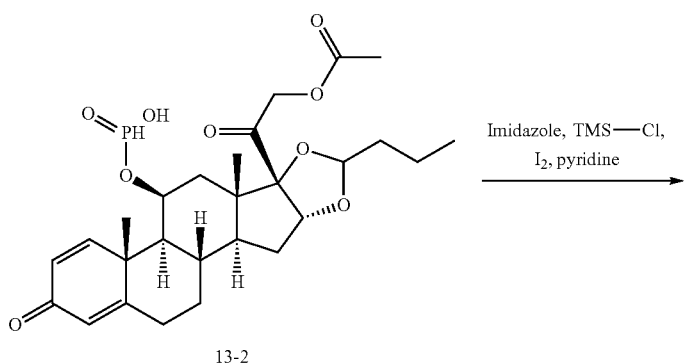
13-2
Imidazole, TMS—Cl, I₂, pyridine →
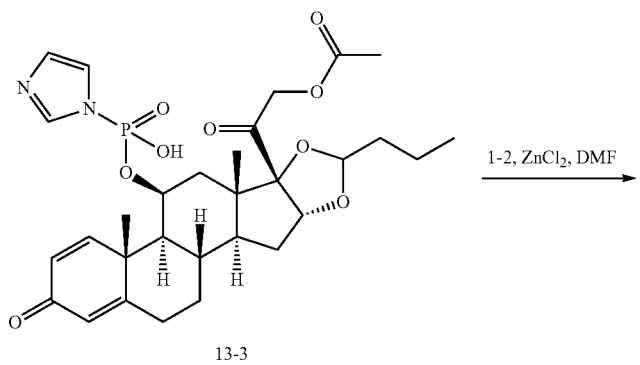
13-3
1-2, ZnCl₂, DMF →

-continued
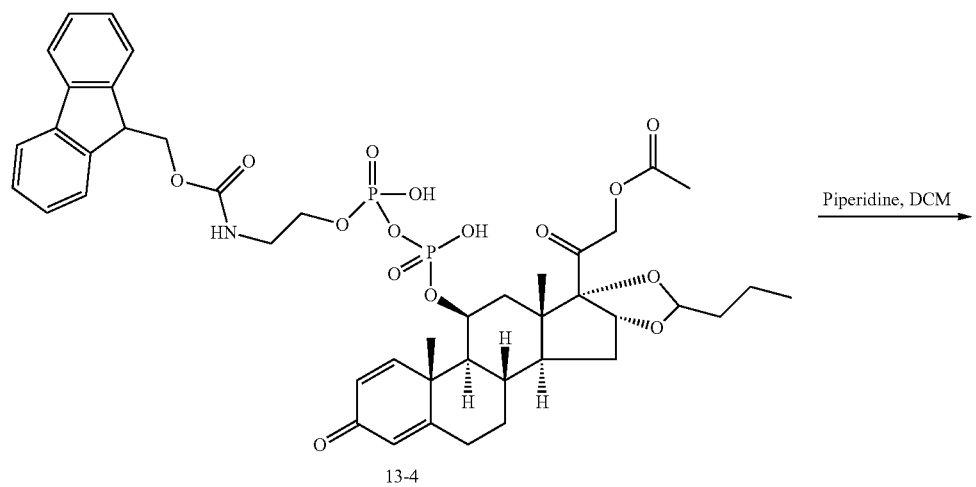
13-4
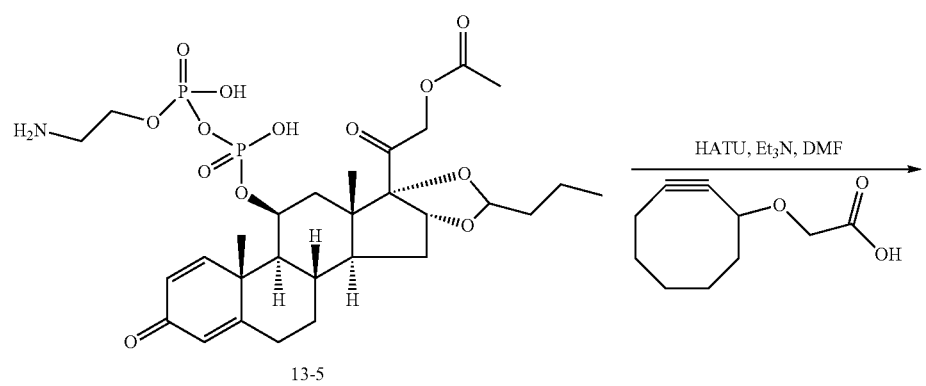
13-5
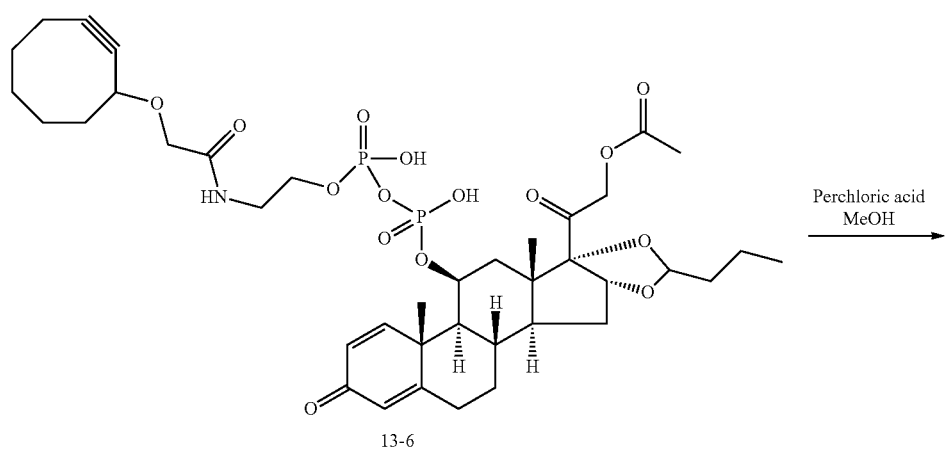
13-6

-continued

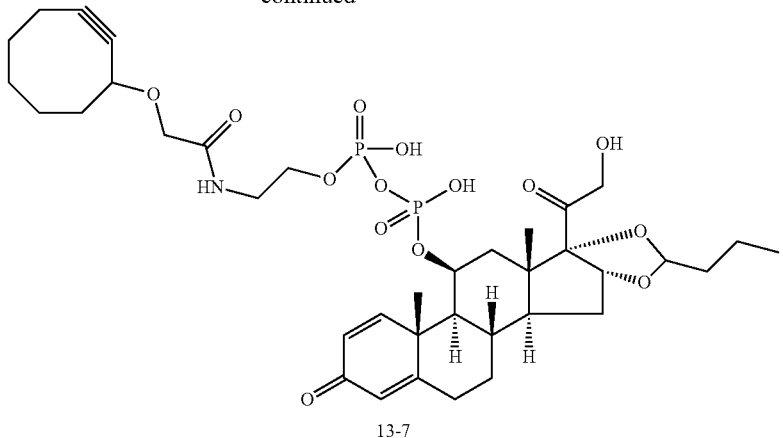

13-7

Step A: synthesis 2-((6aR,6bS,7S,8aS,8bS,11aR, 12aS,12bS)-7-hydroxy-6a,8a-dimethyl-4-oxo-10-propyl-2,4,6a,6b,7,8,8a, 8b,11a,12,12a,12b-dodecahydro-1H-naphtho[2',1':4,5]indeno[1,2-d][1,3]dioxol-8b-yl)-2-oxoethyl acetate (13-1)

To a stirred solution of budesonide (2.00 g, 4.65 mmol) in pyridine (20.0 mL) at room temperature was added acetic anhydride (2.0 mL, 21.20 mmol) and the resulting mixture was stirred for 2.5 hours. The reaction was chilled in an ice bath and quenched with saturated sodium bicarbonate solution (20.0 mL). The solution was extracted several times with ethyl acetate. The combined organic phase washed with brine, dried over sodium sulfate and concentrated to give 13-1 as a solid (2.30 g, 105%). LRMS (ES) (M+H)$^+$: observed=473.4, calculated=472.5.

Step B: 2-((6aR,6bS,7S,8aS,8bS,11aR,12aS,12bS)-7-((hydroxyhydrophosphoryl)oxy)-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-2)

To a stirred solution of 13-1 (0.50 g, 1.06 mmol) in THF (10.0 mL) at −78° C. was added phosphorus trichloride (0.18 mL, 2.12 mmol) dissolved in THF (2.0 mL) followed by triethylamine (0.74 mL, 5.29 mmol) dissolved in THF (2.0 mL). The resulting mixture was stirred at −78° C. for 10 minutes and allowed to warm to room temperature for 45 minutes. The reaction was chilled in an ice bath and quenched with water (0.50 mL). The solution was allowed to warm to room temperature and saturated sodium bicarbonate solution was added until pH 9 and stirred for 10 minutes. The mixture was acidified with 1N HCl and was extracted several times with ethyl acetate. The combined organic phase was dried over sodium sulfate and concentrated to give 13-2 as a solid (0.55 g, 97%). LRMS (ES) (M+H)$^+$: observed=537.3, calculated=536.5.

Step C: 2-((6aR,6bS,7S,8aS,8bS,11aR,12aS,12bS)-7-((hydroxy(1H-imidazol-1-yl)phosphoryl)oxy)-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-3)

To a stirred solution of 13-2 (0.55 g, 1.03 mmol) and imidazole (0.35 g, 5.13 mmol) in pyridine (8.0 mL) at room temperature was added TMS-Cl (1.31 mL, 10.25 mmol) and the resulting solution was stirred for 10 minutes. To this mixture was added iodine (0.52 g, 2.05 mmol) dissolved in pyridine (2 mL) and stirred room temperature for 50 minutes. The reaction was then cooled in and ice bath and quenched with water (0.5 mL). The reaction was concentrated, dissolved in aqueous acetonitrile and purified using reverse phase preparative chromatography (Phenomenex Gemini-NX C18 OBD 5 μM 30×100 mm; 10-50% MeCN/water w/0.1% NH$_4$OH modifier over 20 min) to give 13-3 as a solid (282 mg, 45%). LRMS (ES) (M+H)$^+$: observed=603.4, calculated=602.6.

Step D: 2-((6aR,6bS,7S,8aS,8bS,11aR,12aS,12bS)-7-(((((2-((((9H-fluoren-9-yl)methoxy)carbonyl)amino)ethoxy) (hydroxy)phosphoryl)oxy) (hydroxy)phosphoryl)oxy)-6a, 8a-dimethyl-4-oxo-10-propyl-2,4,6a,6b,7,8,8a, 8b,11a,12,12a,12b-dodecahydro-1H-naphtho[2',1':4,5]indeno[1,2-d][1,3]dioxol-8b-yl)-2-oxoethyl acetate (13-4)

To a stirred solution of 13-3 (0.20 g, 0.33 mmol) and 1-2 (0.12 g, 0.33 mmol) in DMF (1.4 mL) was added ZnCl$_2$ (0.36 g, 2.66 mmol) and the mixture was allowed to stir at room temperature overnight. The reaction was diluted with 1 N HCl and extracted several times with ethyl acetate. The combined organic layers were concentrated, dissolved in aqueous acetonitrile and purified using reverse phase preparative chromatography (Phenomenex Gemini-NX C18 OBD 5 μM 30×100 mm; 10-50% MeCN/water w/0.1% NH$_4$OH modifier over 20 min) to give 13-4 as a solid (166 mg, 55%). LRMS (ES) (M+H)$^+$: observed=898.4, calculated=897.8.

Step E: 2-((6aR,6bS,7S,8aS,8bS,11aR,12aS,12bS)-7-(((((2-aminoethoxy) (hydroxy)phosphoryl)oxy) (hydroxy)phosphoryl)oxy)-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-5)

The title compound was prepared from 13-4 according to the protocol outlined in Example 2 to prepare 2-4 to afford 13-5. LRMS (ES) (M+H)$^+$: observed=676.4, calculated=675.6.

Step F: 2-((6aR,6bS,7S,8aS,8bS,11aR,12aS,12bS)-7-(((((2-(2-(cyclooct-2-yn-1-yloxy)acetamido)ethoxy)(hydroxy)phosphoryl)oxy)(hydroxy)phosphoryl)oxy)-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-6)

To a stirred solution of 13-5 (0.037 g, 0.055 mmol) and 2-(cyclooct-2-yn-1-yloxy)acetic acid (0.032 g, 0.175 mmol) in DMF (0.8 mL) was added HATU (0.066 g, 0.175 mmol) and triethylamine (0.03 mL, 0.22 mmol). The reaction was stirred at room temperature for 20 minutes, then purified directly using reverse phase preparative chromatography (Phenomenex Gemini-NX C18 OBD 5 μM 30×100 mm; 10-50% MeCN/water w/0.1% NH$_4$OH modifier over 20 min) to give 13-6 as a solid (36 mg, 78%). LRMS (ES) (M+H)$^+$ observed=840.5, calculated=839.8.

Step G: 2-((6aR,6bS,7S,8aS,8bS,11aR,12aS,12bS)-7-hydroxy-6a,8a-dimethyl-4-oxo-10-propyl-2,4,6a,6b,7,8,8a,8b,11aR,12,12a,12b-dodecahydro-1H-naphtho[2',1':4,5]indeno[1,2-d][1,3]dioxol-8b-yl)-2-oxoethyl acetate (13-7)

To a stirred solution of 13-6 (0.035 mg, 0.042 mmol) in methanol (0.50 mL) was added 70% perchloric acid (7.2 μL, 0.083 mmol) and the resulting solution was stirred room temperature overnight. The reaction was purified directly using reverse phase preparative chromatography (Phenomenex Gemini-NX C18 OBD 5 μM 30×100 mm; 10-50% MeCN/water w/0.1% NH$_4$OH modifier over 20 min) to give 13-7 as a solid (16 mg, 47%). LRMS (ES) (M+H)$^+$: observed=798.4, calculated=797.7.

Example 14

The synthesis of Fluticasone proprionate linker (6S,8S,9R,10S,11S,13 S,14S,16R,17R)-11-(((((2-(2-(clooct-2-yn-1-yloxy)acetamido)ethoxy)(hydroxy)phosphoryl)oxy)(hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (14-5) was as follows.

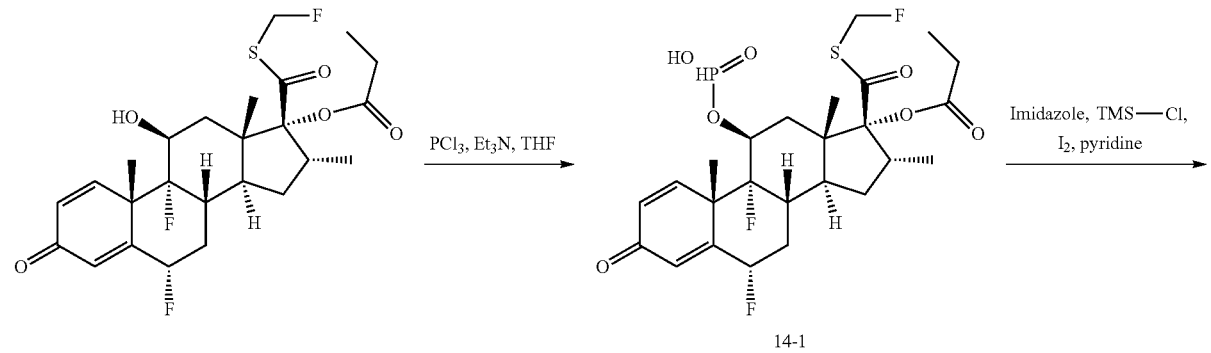

14-1

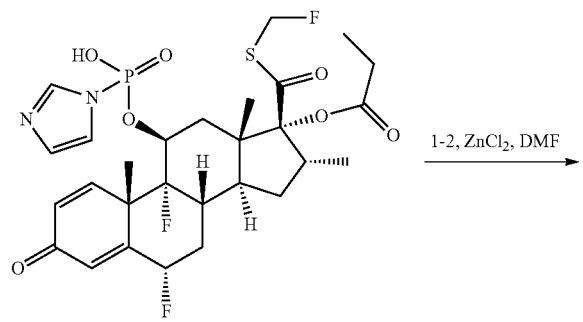

14-2

-continued

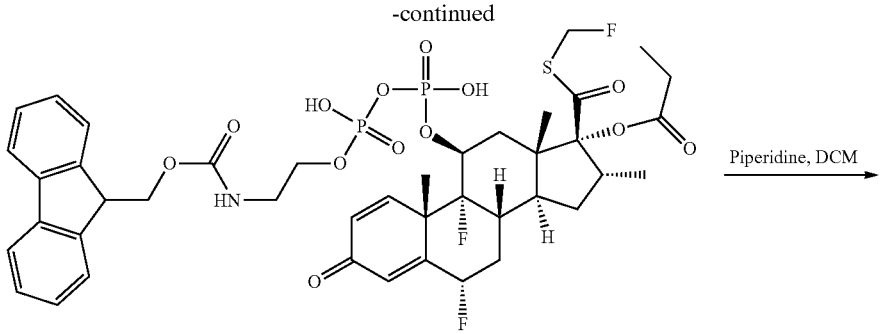

14-3

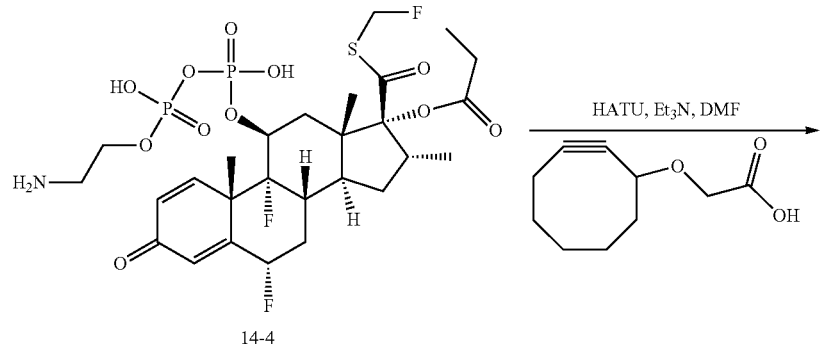

14-4

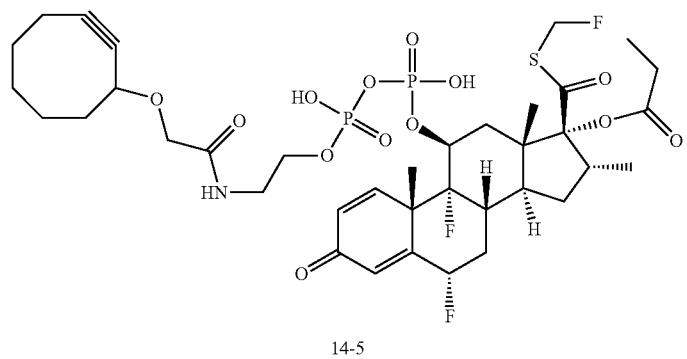

14-5

Step A: (6S,8S,9R,10S,11S,13S,14S,16R,17R)-6,9-difluoro-17-(((fluoromethyl)thio)carbonyl)-11-((hydroxyhydrophosphoryl)oxy)-10,13,16-trimethyl-3-oxo-6,7,8,9,10,11,12,13,14,15,16,17-dodecahydro-3H-cyclopenta[a]phenanthren-17-yl propionate (14-1)

The title compound was prepared from fluticasone propionate according to the protocol outlined in Example 13 to prepare 13-2 to afford 14-1. LRMS (ES) (M+H)$^+$: observed=565.3, calculated=564.5.

Step B: (6S,8S,9R,10S,11S,13S,14S,16R,17R)-6,9-difluoro-17-(((fluoromethyl)thio)carbonyl)-11-((hydroxy(1H-imidazol-1-yl)phosphoryl)oxy)-10,13,16-trimethyl-3-oxo-6,7,8,9,10,11,12,13,14,15,16,17-dodecahydro-3H-cyclopenta[a]phenanthren-17-yl propionate (14-2)

The title compound was prepared from 14-1 according to the protocol outlined in Example 13 to prepare 13-3 to afford 14-2. LRMS (ES) (M-+H)$^+$: observed=631.3, calculated=630.6.

Step C: (6S,8S,9R,10S,11S,13S,14S,16R,17R)-11-(((((2-((((9H-fluoren-9-yl)methoxy)carbonyl)amino)ethoxy) (hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-ylpropionate (14-3)

The title compound was prepared from 14-2 according to the protocol outlined in Example 13 to prepare 13-4 to afford 14-3. LRMS (ES) (M+H)$^+$: observed=943.4 (M+H+NH$_3$), calculated=925.8.

Step D: (6S,8S,9R,10S,11S,13S,14S,16R,17R)-11-(((((2-aminoethoxy) (hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (14-4)

The title compound was prepared from 14-3 according to the protocol outlined in Example 2 to prepare 2-4 to afford 14-4. LRMS (ES) (M+H)$^+$: observed=704.3, calculated=703.6.

Step F: (6S,8S,9R,10S,11S,13S,14S,16R,17R)-11-(((((2-(2-(cyclooct-2-yn-1-yloxy)acetamido)ethoxy)(hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (14-5)

The title compound was prepared from 14-4 according to the protocol outlined in Example 13 to prepare 13-6 to afford 14-5. LRMS (ES) (M+H)$^+$: observed=868.4, calculated=867.8.

Example 15

The synthesis of (6S,8S,9R,10S,11S,13S,14S,16R,17R)-11-((((((2-(2-(cyclooct-2-yn-1-yloxy)acetamido)ethoxy)(hydroxy)phosphoryl)oxy)(hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (15-5) was as follows.

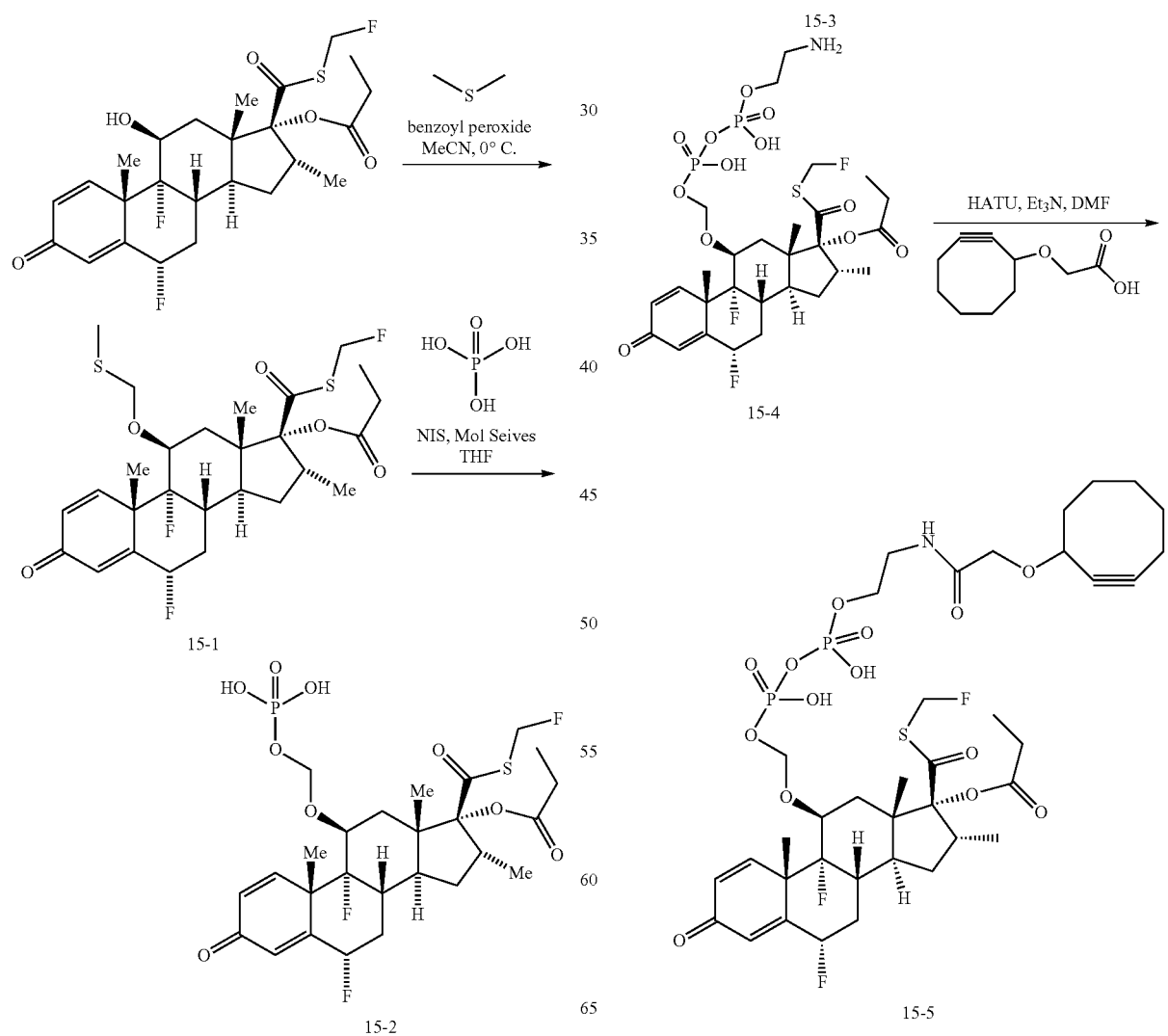

Step A: (6S,8S,9R,10S,11S,13S,14S,16R,17R)-6,9-difluoro-17-(((fluoromethyl)thio)carbonyl)-10,13,16-trimethyl-11-((methylthio)methoxy)-3-oxo-6,7,8,9,10,11,12,13,14,15,16,17-dodecahydro-3H-cyclopenta[a]phenanthren-17-yl propionate (15-1)

To a stirred solution of fluticasone propionate (0.50 g, 1.00 mmol) in MeCN (5.0 mL) at 0° C. was added dimethyl sulfide (0.59 mL, 8.00 mmol) followed by benzoyl peroxide (0.97 g, 4.00 mmol) added in four portions over 20 minutes. The resulting mixture was stirred at 0° C. for 1 hour. The reaction was concentrated, taken up in ethyl acetate and washed with saturated sodium bicarbonate. The combined organic phase was concentrated. The crude was purified directly using reverse phase preparative chromatography (Phenomenex Gemini-NX C18 OBD 5 uM 30×100 mm; 40-80% MeCN/water w/0.1% NH$_4$OH modifier over 20 min) to give to give 15-1 as a solid (0.07 g, 12.7%). LRMS (ES) (M+H)$^+$: observed=561.3, calculated=560.6.

Step B: (6S,8S,9R,10S,11 S,13S,14S,16R,17R)-6,9-difluoro-17-(((fluoromethyl) thio)carbonyl)-10,13,16-trimethyl-3-oxo-1-((phosphonooxy)methoxy)-6,7,8,9,10,11,12,13,14,15,16,17-dodecahydro-3H-cyclopenta[a]phenanthren-17-yl propionate (15-2)

Phosphoric acid (0.09 g, 0.89 mmol) was heated under nitrogen at 120° C. for 30 minutes. This was allowed to cool and to it was added molecular sieves and 15-1 (0.07 g, 0.13 mmol). This mixture was dissolved in THF (1.3 mL) and NIS (0.04 g, 0.19 mmol) was added. The resulting solution was allowed to stir overnight at room temperature. The mixture was filtered and concentrated. The crude was purified directly using reverse phase preparative chromatography (Phenomenex Gemini-NX C18 OBD 5 uM 30×100 mm; 10-50% MeCN/water w/0.1% NH$_4$OH modifier over 20 min) to give to give 15-2 as a solid (0.05 g, 63%). LRMS (ES) (M+H)$^+$: observed=611.3, calculated=610.5.

Step C: (6S,8S,9R,10S,11S,13S,14S,16R,17R)-11-((((((2-(((((9H-fluoren-9-yl)methoxy)carbonyl)amino)ethoxy) (hydroxy)phosphoryl)oxy) (hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (15-3)

The title compound was prepared from 15-2 according to the protocol outlined in Example 1-3 to afford 15-3. LRMS (ES) (M+H)$^+$: observed=956.5, calculated=955.8.

Step D: (6S,8S,9R,10S,11S,13S,14S,16R,17R)-11-((((((2-aminoethoxy) (hydroxy)phosphoryl)oxy) (hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (15-4)

The title compound was prepared from 15-3 according to the protocol outlined in Example 12-2 to afford 15-4. LRMS (ES) (M+H)$^+$: observed=734.5, calculated=733.6.

Step E: (6S,8S,9R,10S,11S,13S,14S,16R,17R)-11-(((((2-(2-(cyclooct-2-yn-1-yloxy)acetamido)ethoxy) (hydroxy)phosphoryl)oxy) (hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-ylpropionate (15-5)

The title compound was prepared from 15-4 according to the protocol outlined in Example 13-6 to afford 15-5. LRMS (ES) (M+H)$^+$: observed=898.4, calculated=897.8.

Example 16

The synthesis of Budesonide linker 1-(cyclooct-2-yn-1-yloxy)-2-oxo-3-aza-6,9,12,15,18,21,24,27,30,33,36,39,42,45,48,51,54,57,60,63,66,69,72-tricosaoxahenheptacont-74-yl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (16-5) was as follows.

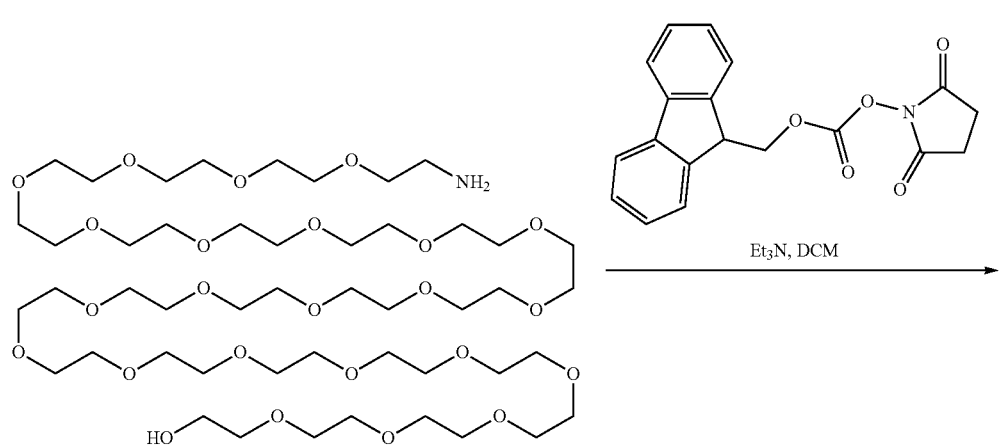

-continued
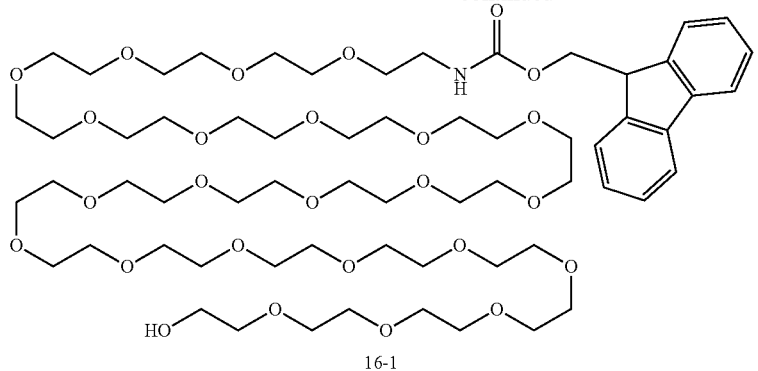
16-1
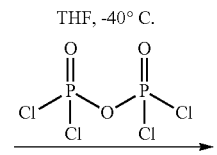
THF, -40° C.
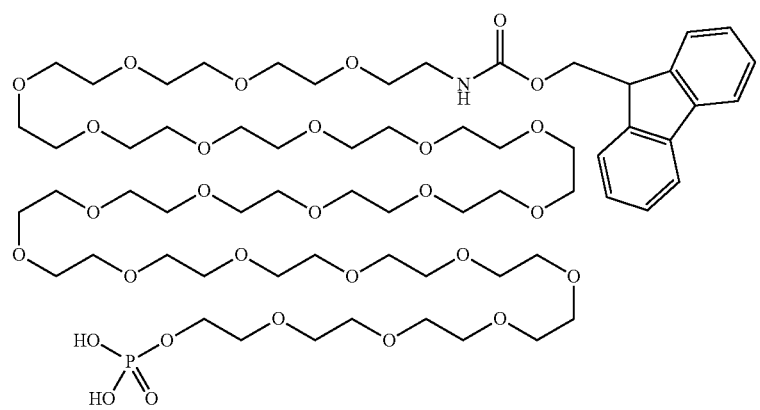
16-2
1.) CDI, Et₃N, DMF
2.) 9-1, ZnCl₂, DMF
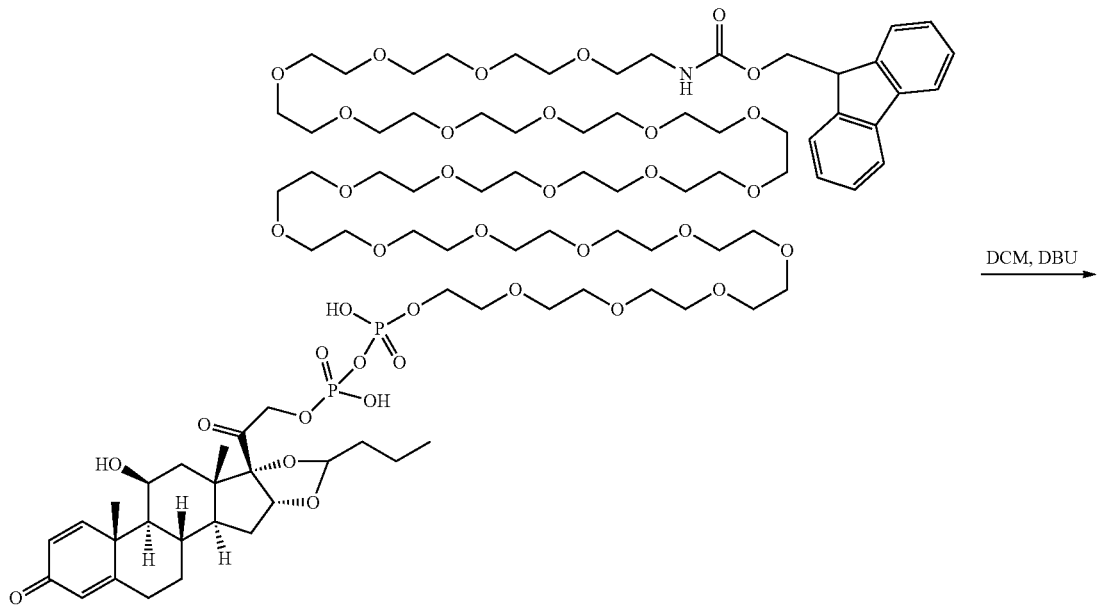
16-3
DCM, DBU -continued

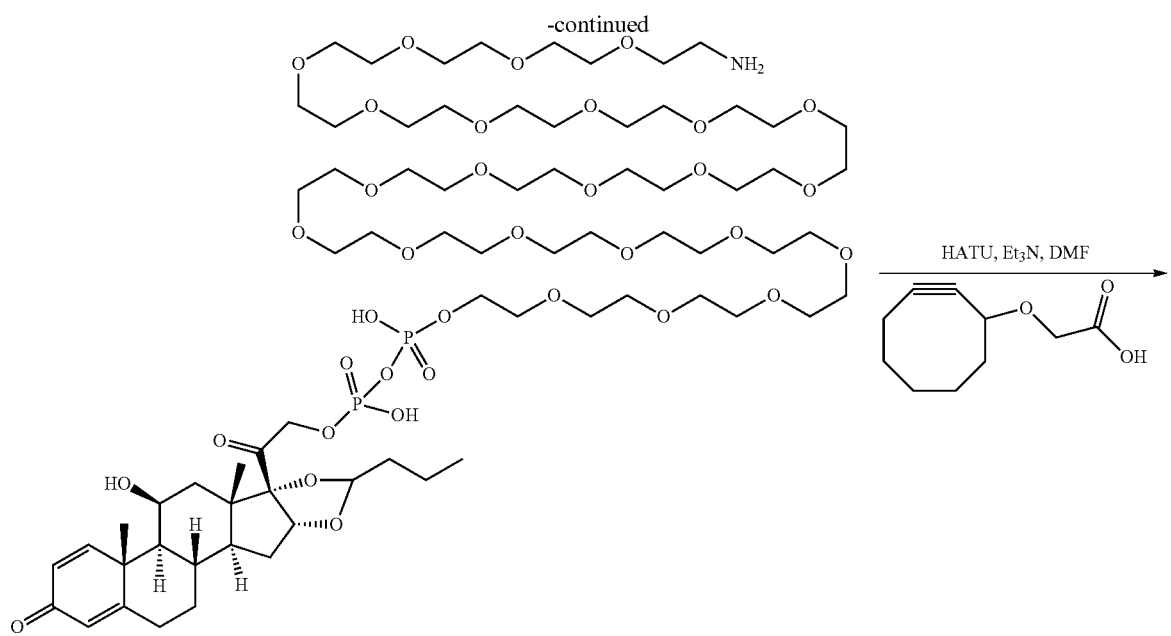

16-4

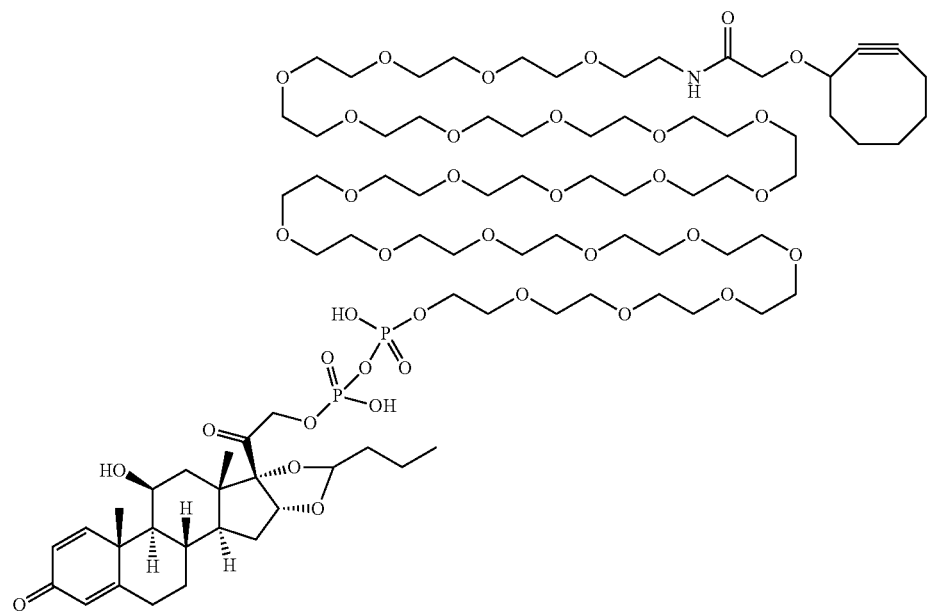

16-5

Step A: (9H-fluoren-9-yl)methyl (71-hydroxy-3,6,9, 12,15,18,21,24,27,30,33,36,39,42,45,48,51,54,57,60, 63,66,69-tricosaoxahenheptacontyl)carbamate (16-1)

The title compound was prepared from 71-amino-3,6,9, 12,15,18,21,24,27,30,33,36,39,42,45,48,51,54,57,60,63,66, 69-tricosaoxahenheptacontan-1-ol and (9H-fluoren-9-yl) methyl (2,5-dioxopyrrolidin-1-yl) carbonate according to the protocol outlined in Example 11 to produce 11-1 to afford 16-1. LRMS (ES) (M+H)$^+$: observed=1314.1, calculated=1296.5.

Step B: (9H-fluoren-9-yl)methyl (71-(phosphonooxy)-3,6,9,12,15,18,21,24,27,30,33,36,39,42,45, 48,51,54,57,60,63,66,69-tricosaoxahenheptacontyl) carbamate (16-2)

The title compound was prepared from 16-1 according to the protocol outlined in Example 1 to produce 1-1 to afford 16-2. LRMS (ES) (M+H)$^+$: observed=1394.0, calculated=1376.5.

Step C: (9H-fluoren-9-yl)methyl (71-((hydroxy((hydroxy(2-(((6aR,6bS,7S,8aS,8bS,11aR,12aS,12bS)-7-hydroxy-6a, 8a-dimethyl-4-oxo-10-propyl-2,4,6a,6b,7,8,8a, 8b,11a,12,12a,12b-dodecahydro-1H-naphtho[2',1':4,5]indeno[1,2-d][1,3]dioxol-8b-yl)-2-oxoethoxy)phosphoryl)oxy)phosphoryl)oxy)-3,6,9,12,15,18,21,24,27,30,33,36,39,42,45,48,51,54,57,60,63,66,69-tricosaoxahenheptacontyl)carbamate (16-3)

The title compound was prepared from 16-2 and 9-1 according to the protocol outlined in Example 1 to produce 1-3 to afford 16-3. LRMS (ES) (M+H)+: observed=1886.7, calculated=1869.0 Step D: 72-amino-3,6,9,12,15,18,21,24,27,30,33,36,39,42,45,48,51,54,57,60,63,66,69-tricosaoxahenheptacontanyl (2-((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (16-4)

The title compound was prepared from 16-3 according to the protocol outlined in Example 12 to produce 12-2 to afford 16-4. LRMS (ES) (M+H)+: observed=1664.0, calculated=1646.7.

Step E: 1-(cyclooct-2-yn-1-yloxy)-2-oxo-3-aza-6,9,12,15,18,21,24,27,30,33,36,39,42,45,48,51,54,57,60,63,66,69,72-tricosaoxahenheptacont-74-yl (2-((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (16-5)

The title compound was prepared from 16-4 according to the protocol outlined in Example 13 to produce 13-6 to afford 16-5. LRMS (ES) (M+H)+: observed=1828.7, calculated=1810.9.

Example 17

The synthesis of Budesonide linker 4-((2S)-2-((2S)-2-(2-(cyclooct-2-yn-1-yloxy)acetamido)-3-methylbutanamido)-5-ureidopentanamido)benzyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (17-2) was as follows.

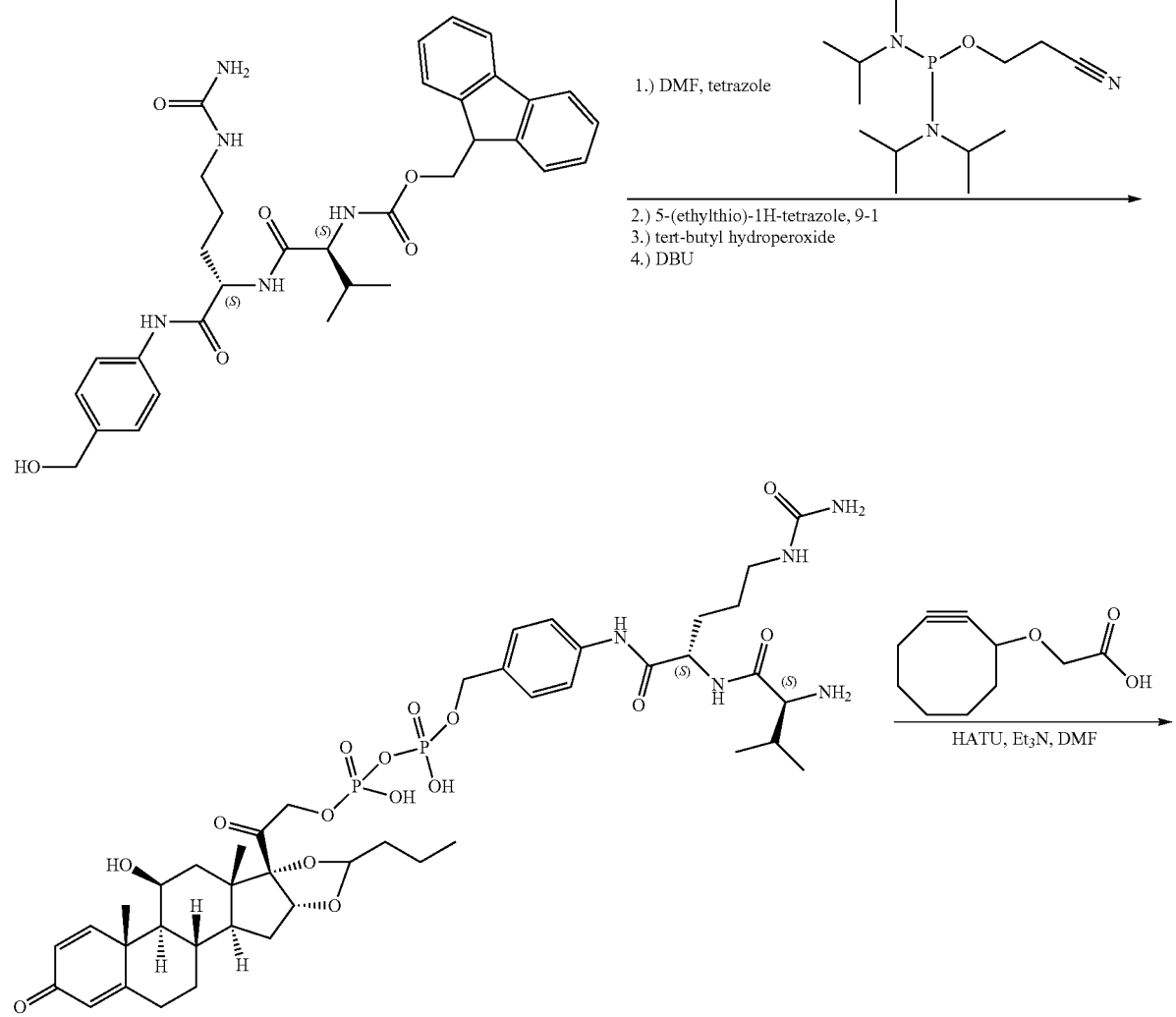

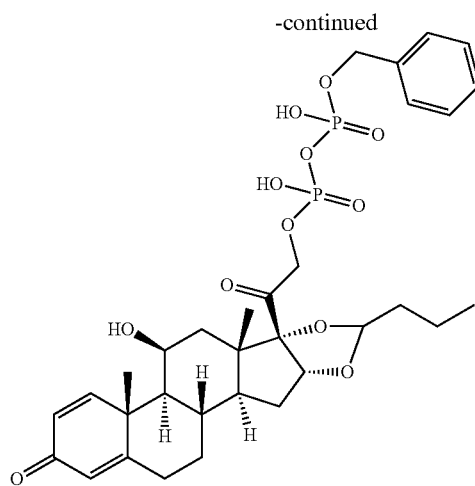
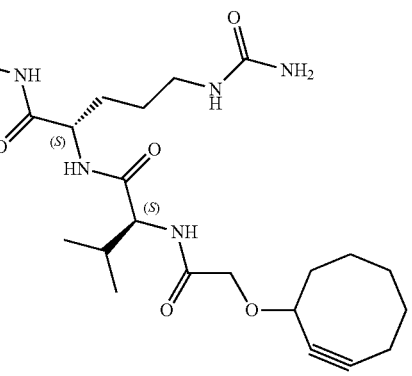

17-2

Step A: 4-((S)-2-((S)-2-amino-3-methylbutanamido)-5-ureidopentanamido)benzyl (2(((6aR,6bS,7S,8aS,8bS,11aR,12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1''':4,5]indeno[1,2-d][1,3]dioxol-8b-yl)-2-oxoethyl) dihydrogen pyrophosphate (17-1)

To a stirred solution of (9H-fluoren-9-yl)methyl ((S)-1-(((S)-1-((4(hydroxymethyl)phenyl)amino)-1-oxo-5-ureidopentan-2-yl)amino)-3-methyl-1-oxobutan-2-yl)carbamate (0.05 g, 0.083 mmol) in DMF (1.2 mL) was added 3-((bis(diisopropylamino)phosphino)oxy)propanenitrile (29 uL, 0.09 mmol). To this mixture was added 0.45M tetrazole in acetonitrile (0.20 mL, 0.09 mmol) dropwise and the resulting mixture was stirred for 20 minutes at room temperature. To this was added 9-1 (0.042 g, 0.083 mmol) and 5-(ethylthio)-1H-tetrazole (0.02 g, 0.16 mmol) and allowed to stir to 30 minutes at room temperature. To this was added 6 M tertbutyl hydroperoxide in decane (0.03 mL, 0.18 mmol) and allowed to stir at room temperature for 30 minutes. To this was added DBU (0.12 mL, 0.83 mmol) and the resulting solution was stirred overnight at room temperature. The crude reaction was purified by direct injection using reverse phase preparative chromatography (Phenomenex Gemini-NX C18 OBD 5 uM 30×100 mm; 5-40% MeCN/water w/0.1% NH$_4$OH modifier over 20 min) to give 17-1 as a solid (18.5 mg, 23%). LRMS (ES) (M+H)$^+$: observed=952.6, calculated=951.9.

Step B: 4-((2S)-2-((2S)-2-(2-(cyclooct-2-yn-1-yloxy)acetamido)-3-methylbutanamido)-5-ureidopentanamido) benzyl (2-((6aR,6bS,7S,8aS,8bS,11aR, 12aS,12bS)-7-hydroxy-6a, 8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (17-2)

The title compound was prepared from 17-1 according to the protocol outlined in Example 13 to produce 13-6 to afford 17-2. LRMS (ES) (M+H)$^+$: observed=1116.6, calculated=1116.1.

Example 18

The synthesis of Fluticasone linker (6S,8S,9R,10S,11S,13S,14S,16R,17R)-11-((((((4-((2S)-2-((2S)-2-(2-(cyclooct-2-yn-1-yloxy)acetamido)-3-methylbutanamido)-5-ureidopentanamido)benzyl)oxy)(hydroxy)phosphoryl)oxy)(hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (18-3) was as follows.

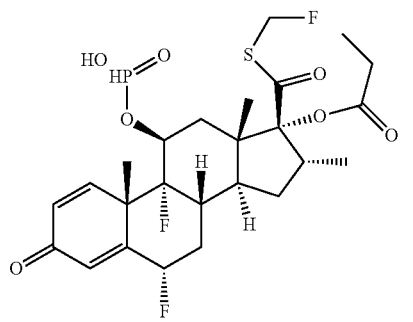
14-1

Imidazole, TMS—Cl,
I$_2$, pyridine
→

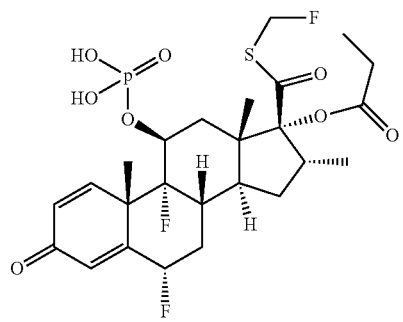
18-1

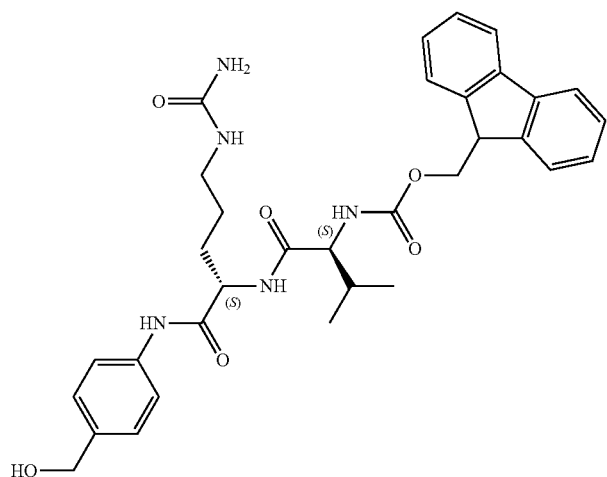
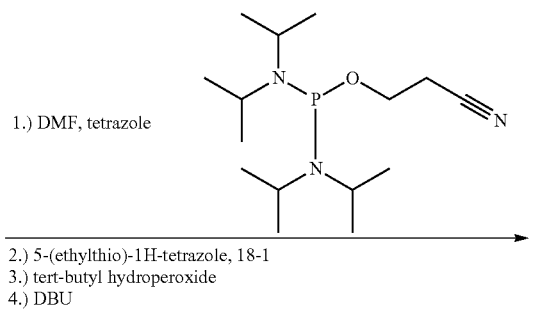
1.) DMF, tetrazole
2.) 5-(ethylthio)-1H-tetrazole, 18-1
3.) tert-butyl hydroperoxide
4.) DBU
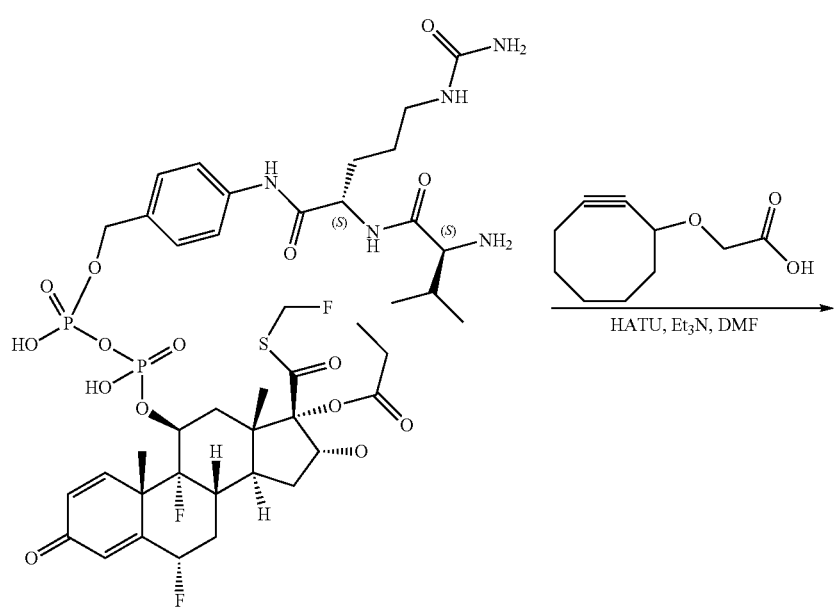
18-2
HATU, Et$_3$N, DMF

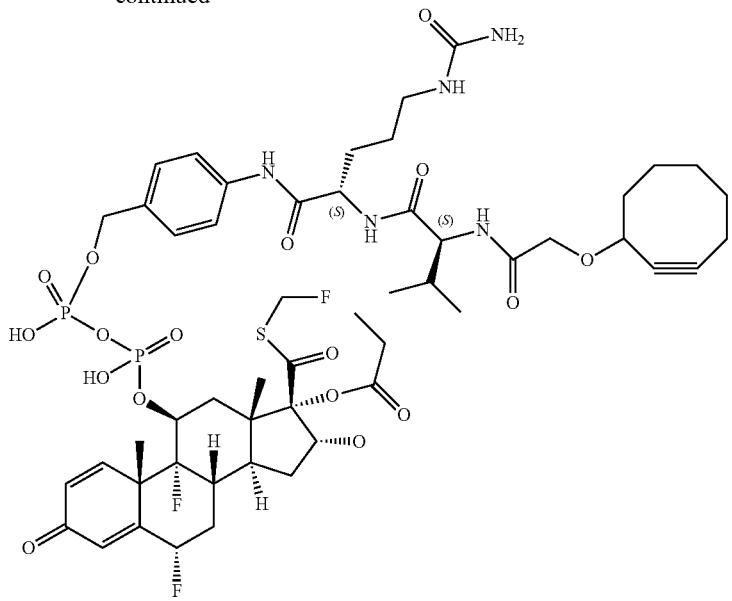

18-3

Step A: (6S,8S,9R,10S,11S,13S,14S,16R,17R)-6,9-difluoro-17-(((fluoromethyl)thio)carbonyl)-10,13,16-trimethyl-3-oxo-11-(phosphonooxy)-6,7,8,9,10,11,12,13,14,15,16,17-dodecahydro-3H-cyclopenta[a]phenanthren-17-ylpropionate (18-1)

To a stirred solution of 14-1 (0.20 g, 0.35 mmol) in pyridine (3.0 mL) at room temperature was added TMS-Cl (0.45 mL, 3.54 mmol) and the resulting solution was stirred for 10 minutes. To this mixture was added iodine (0.10 g, 0.42 mmol) dissolved in pyridine (0.5 mL) and stirred room temperature for 10 minutes. The reaction was then cooled in an ice bath and quenched with water (0.5 mL) and allowed to stir overnight at room temperature. The reaction was partitioned between ethyl acetate and 1N HCl. The organic phase was concentrated and dissolved in aqueous acetonitrile and purified using reverse phase preparative chromatography (Phenomenex Gemini-NX C18 OBD 5 μM 30×100 mm; 5-40% MeCN/water w/0.1% NH$_4$OH modifier over 20 min) to give 18-1 as a solid (89 mg, 44%). LRMS (ES) (M+H)$^+$: observed=581.3, calculated=580.5.

Step B: (6S,8S,9R,10S,11S,13S,14S,16R,17R)-11-((((((4-((S)-2-((S)-2-amino-3-methylbutanamido)-5-ureidopentanamido) benzyl)oxy) (hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (18-2)

The title compound was prepared from 18-1 according to the protocol outlined in Example 17 to produce 17-1 to afford 18-2. LRMS (ES) (M+H)$^+$: observed=1022.6, calculated=1021.9.

Step C: (6S,8S,9R,10S,11S,13S,14S,16R,17R)-11-((((((4-((2S)-2-((2S)-2-(2-(cyclooct-2-yn-1-yloxy) acetamido)-3-methylbutanamido)-5-ureidopentanamido) benzyl)oxy) (hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-ylpropionate (18-3)

The title compound was prepared from 18-2 according to the protocol outlined in Example 13 to produce 13-6 to afford 18-3. LRMS (ES) (M+H)$^+$: observed=1186.5, calculated=1186.1.

Example 19

The synthesis of Budesonide linker 4-(2-(cyclooct-2-yn-1-yloxy)acetamido)-1-(trimethylammonio)butan-2-yl (2-((6aR,6bS,7S,8aS,8bS,11aR,12aS,12bS)-7-hydroxy-6a,8a-dimethyl-4-oxo-10-propyl-2,4,6a,6b,7,8,8a,8b, 11a,12,12a,12b-dodecahydro-1H-naphtho[2',1':4,5]indeno[1,2-d][1,3]dioxol-8b-yl)-2-oxoethyl)phosphate (19-5) was as follows.

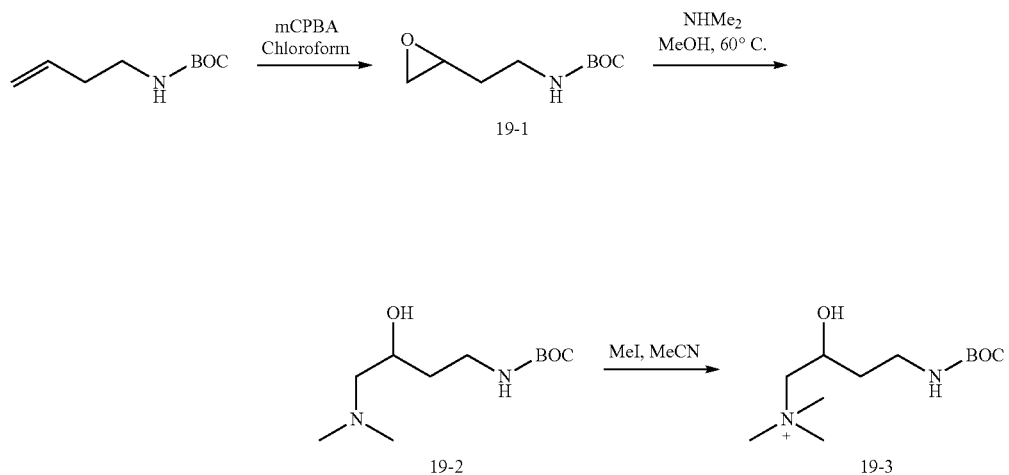
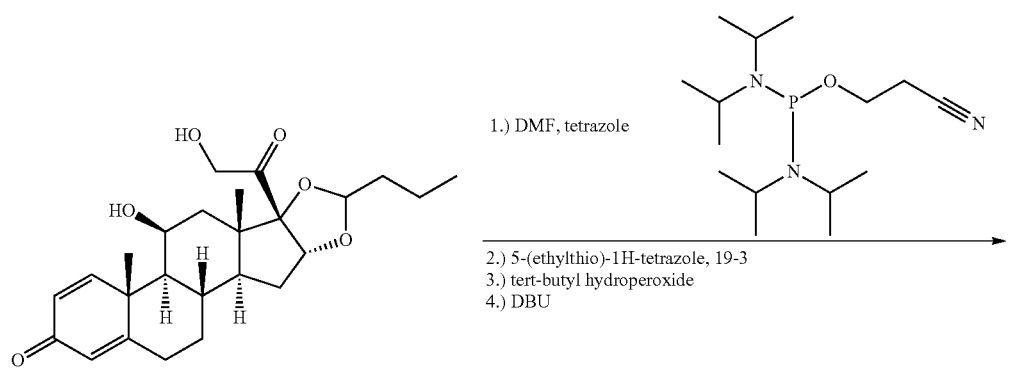
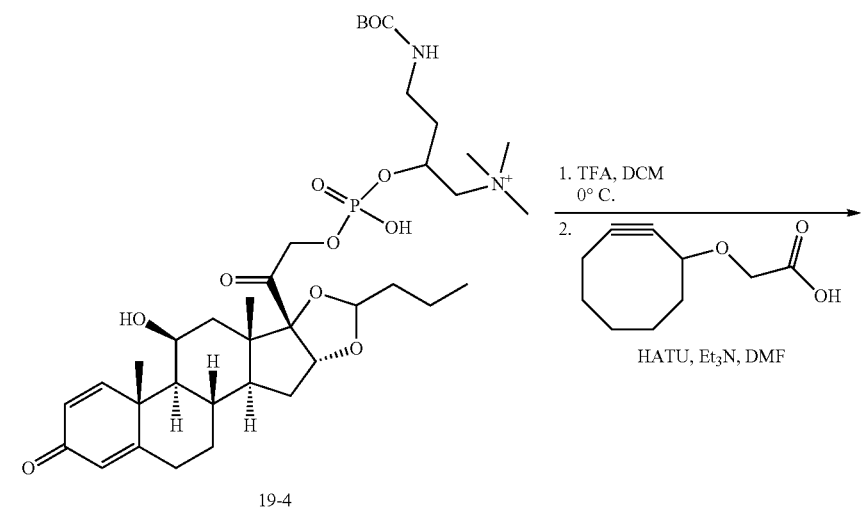

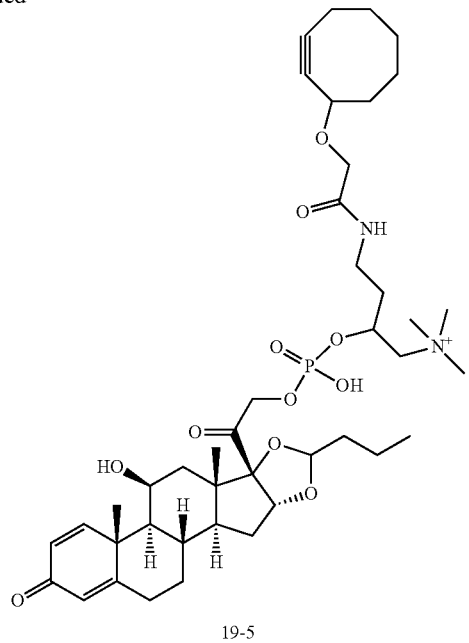

19-5

Step A: tert-butyl (2-(oxiran-2-yl)ethyl)carbamate (19-1)

To a stirred solution of tert-butyl but-3-enylcarbamate (0.95 mL, 5.16 mmol) in chloroform (20 mL) chilled in an ice bath was added mCBPA (1.38 g, 8.0 mmol) and the resulting solution was stirred for 30 minutes. The reaction was allowed to warm to room temperature and monitored by TLC. Additional 1.5 equivalents of mCPBA was added every 30 minutes until complete. The mixture was diluted with additional 50 mL chloroform and washed with 10% aq sodium sulfite solution 3 times, and washed once with brine. The organic phase as dried over sodium sulfate and concentrated. The crude mixture was purified with flash column separation using a 0-50% ethyl acetate/hexane gradient to give 19-1 (800 mg, 83%). LRMS (ES) (M+H)$^+$: observed=188.0, calculated=187.2.

Step B: tert-butyl (4-(dimethylamino)-3-hydroxybutyl)carbamate (19-2)

Compound 19-1 (0.79 g, 4.21 mmol) was dissolved in a solution of dimethylamine 2M (8.0 mL, 16.0 mmol) and microwave irradiated to 60° C. for 30 minutes. The reaction was allowed to cool and concentrated. The mixture was dissolved in aqueous acetonitrile and purified using reverse phase preparative chromatography (Phenomenex Gemini-NX C18 OBD 5 μM 30×100 mm; 10-50% MeCN/water w/0.1% NH$_4$OH modifier over 20 min) to give 19-2 (528 mg, 54%). LRMS (ES) (M+H)$^+$: observed=234.2, calculated=232.3.

Step C: 4-((tert-butoxycarbonyl)amino)-2-hydroxy-N,N,N-trimethylbutan-1-aminium (19-3)

To a stirred solution of 9-2 (0.48 g, 2.05 mmol) in acetonitrile (9.5 mL) was added methyl iodide (0.13 mL, 2.05 mmol) and the resulting solution was stirred at room temperature for 1 hour and concentrated to give 19-3 as a white hydroscopic solid (509 mg, 100%). LRMS (ES) (M+H)$^+$: observed=248.3, calculated=247.3.

Step D: 4-((tert-butoxycarbonyl)amino)-2-((hydroxy (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethoxy) phosphoryl)oxy)-N,N,N-trimethylbutan-1-aminium (19-4)

The title compound was prepared from 19-3 and Budesonide according to the protocol outlined in Example 17 to produce 17-1 to afford 19-4. LRMS (ES) (M+H)$^+$: observed=739.5, calculated=739.8.

Step E: 4-(2-(cyclooct-2-yn-1-yloxy)acetamido)-1-(trimethylammonio)butan-2-yl (2((6aR,6bS,7S,8aS, 8bS,11 aR, 12aS,12bS)-7-hydroxy-6a, 8a-dimethyl-4-oxo-10-propyl-2,4,6a,6b,7,8,8a, 8b,11a,12,12a, 12b-dodecahydro-1H-naphtho[2',1':4,5]indeno[1,2-d][1,3]dioxol-8b-yl)-2-oxoethyl)phosphate (19-5)

To a stirred solution of 19-4 (0.03 g, 0.04 mmol) in dichloromethane (0.6 mL) in an ice bath was added TFA (0.3 mL, 3.89 mmol) and the resulting solution was allowed to stir 1 hour and concentrated. The resulting crude material was dissolved in DMF (0.4 mL) and 2-(cyclooct-2-yn-1-yloxy)acetic acid (9.6 mg, 0.053 mmol) and HATU (0.022 g, 0.057 mmol) and triethylamine (0.04 mL, 0.28 mmol) was added. The reaction was stirred at room temperature for 20 minutes, then purified directly using reverse phase preparative chromatography (Phenomenex Gemini-NX C18 OBD 5 μM 30×100 mm; 10-60% MeCN/water w/0.1% NH$_4$OH modifier over 20 min) to give 19-5 as a solid (22 mg, 67%). LRMS (ES) (M+H)$^+$: observed=803.6, calculated=802.9.

Example 20

This example shows the synthesis of a duocarmycin analog comprising a diphosphate linker.

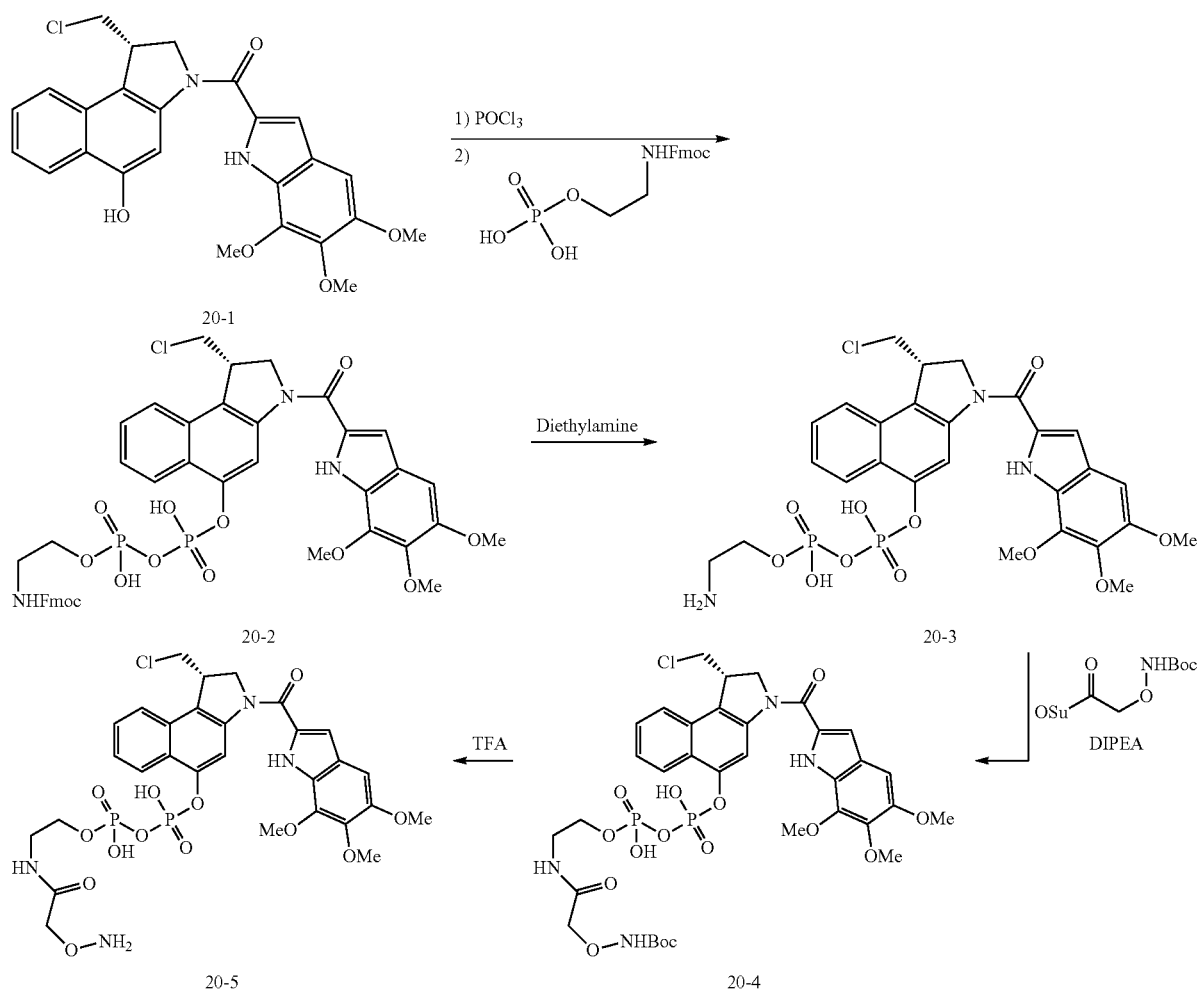

Step A: (9H-fluoren-9-yl)methyl 2-((((S)-1-(chloromethyl)-3-(5, 6,7-trimethoxy-1H-indole-2-carbonyl)-2,3-dihydro-1H-benzo[e]indol-5-yloxy) (hydroxy)phosphoryloxy) (hydroxy)phosphoryloxy) ethylcarbamate (20-2)

(S)-(1-(chloromethyl)-5-hydroxy-1H-benzo[e]indol-3 (2H)-yl)(5,6,7-trimethoxy-1H-indol-2-yl)methanone (20-1) (60.0 mg, 0.13 mmol) was dissolved in dichloromethane (5 mL) and treated with phosphoryl chloride (36 µL, 0.39 mmol) and diisopropylethylamine (67 L, 0.39 mmol) at 0° C. for 5 min. The reaction mixture was cooled down to −30° C. and (9H-fluoren-9-yl)methyl 2-(phosphonooxy)ethylcarbamate (234 mg, 0.64 mmol) was then added followed by another portion of diisopropylethylamine (115 µL, 0.64 mmol). The reaction was kept at −30° C. for 30 min then allowed to warm up to 0° C. for 40 min. Additional amount of 1.0 eq of (9H-fluoren-9-yl)methyl 2-(phosphonooxy) ethylcarbamate (46.8 mg, 0.13 mmol) and diisopropylethylamine (22 µL, 0.13 mmol) were added and kept for another 10 min at 0° C. The reaction was quenched with sodium phosphate monobasic (1M) at 4° C. overnight and purified by RP-HPLC (Phenomenex Gemini-NX C18 5 µm 100×30 mm; MeCN/water with 0.05% TFA) to give the compound 20-2 as white powder (55 mg) with little impurity which is used directly for the next step without further purification. MS m/z 892 (M+H)+.

Step B: 2-((((S)-1-(chloromethyl)-3-(5, 6,7-trimethoxy-1H-indole-2-carbonyl)-2,3-dihydro-1H-benzo[e]indol-5-yloxy) (hydroxy)phosphoryloxy) (hydroxy)phosphoryloxy)ethylamine (20-3)

Compound 20-2 (55 mg from last step) was dissolved in DMF (4.5 mL) and treated with diethylamine (0.6 ml) at rt for 10 min and immediately purified by RP-HPLC (Phenomenex Gemini NX C18 5 µm 100×30 mm; MeCN/water with 0.05% TFA) and lyophilized to obtain a white powder as TFA salt of compound 20-3 (24 mg, 24% from compound 20-1). $^1$H-NMR (500 MHz, CDCl$_3$/MeOH-d4) δ 8.52 (bs, 1H), 8.32 (d, J=8.5 Hz, 1H), 7.82 (d, J=8.5 Hz, 1H), 7.56 (t, J=7.0 Hz, 1H), 7.45 (t, J=7.0 Hz, 1H), 7.08 (s, 1H), 6.95 (s, 1H), 4.73-4.72 (m, 2H), 4.28-4.20 (m, 3H), 4.04 (s, 3H), 3.99-3.96 (m, 1H), 3.90 (3, 3H), 3.89 (s, 3H), 3.69-3.65 (m, 1H), 3.21 (m, 2H). MS m/z 670 (M+H)+.

Step C: tert-Butyl 2-(2-((((S)-1-(chloromethyl)-3-(5,6,7-trimethoxy-1H-indole-2-carbonyl)-2,3-dihydro-1H-benzo[e]indol-5-yloxy) (hydroxy)phosphoryloxy) (hydroxy)phosphoryloxy)ethylamino)-2-oxoethoxycarbamate (20-4)

A solution of 20-3 mono TFA salt (10 mg, 0.0128 mmol) in DMF (0.5 mL) was treated with 2,5-dioxopyrrolidin-1-yl 2-(tert-butoxycarbonylaminooxy)acetate (7.35 mg, 0.0256 mmol) and diisopropylethyl amine (8.9 µL, 0.0512 mmol) at 0° C. for 10 min. The reaction mixture was purified by RP-HPLC (Phenomenex Gemini-NX C18 5 µm 100×30 mm; MeCN/water with 0.05% TFA) to obtain a white powder as compound 20-4 (8.6 mg, 80%). MS m/z 843 (M+H)+.

Step D: 2-(Aminooxy)-N-(2-((((S)-1-(chloromethyl)-3-(5,6,7-trimethoxy-1H-indole-2-carbonyl)-2,3-dihydro-H-benzo[e]indol-5-yloxy) (hydroxy)phosphoryloxy) (hydroxy)phosphoryloxy)ethyl)-acetamide (20-5)

Compound 20-4 (8.5 mg, 0.010 mmol) was dissolved in dichloromethane (0.5 mL) and treated with TFA (0.1 mL) at rt for 15 min. The reaction mixture was concentrated in vacuum and co-evaporated with toluene (0.5 mL×2). The residue was purified by RP-HPLC (Phenomenex Gemini-NX C18 5 µm 100×30 mm; MeCN/water with 0.05% TFA) to obtain the target compound 20-5 as TFA salt (3.7 mg, 50%). ¹H-NMR (500 MHz, MeOH-d4) δ 8.53 (d, J=13.5 Hz, 1H), 8.3 (t, J=7.5 Hz, 1H), 7.84 (d, J=8.5 Hz, 1H), 7.60-7.57 (m, 1H), 7.47 (t, J=7.5 Hz, 1H), 7.12 (d, J=12.0 Hz, 1H), 6.99 (d, J=2.0 Hz, 1H), 4.76-4.74 (m, 2H), 4.58 (s, 1H), 4.37-4.34 (m, 1H), 4.25 (m, 1H), 4.20-4.14 (m, 2H), 4.06 (d, J=6.0 Hz, 3H), 4.02-4.00 (m, 1H), 3.90 (s, 6H), 3.76-3.70 (m, 1H), 3.45-3.44 (m, 2H). MS m/z 743 (M+H)+.

Example 21

This example shows the synthesis of duocarmycin comprising a diphosphate linker.

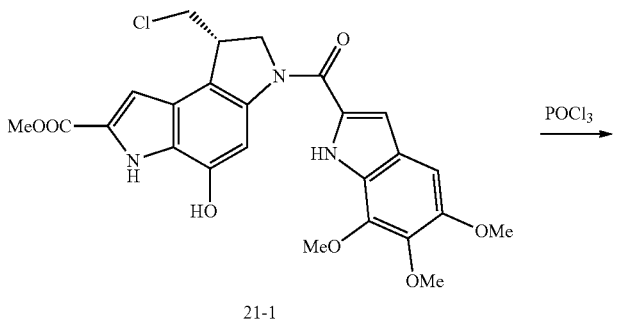

21-1

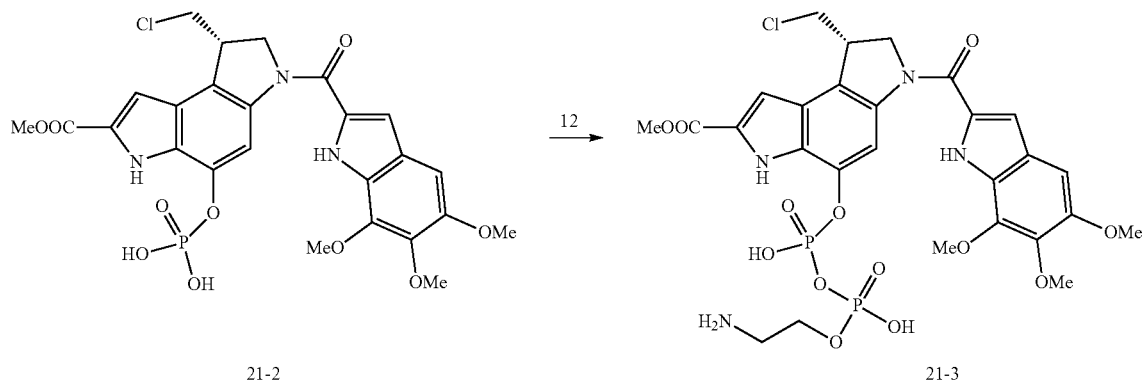

21-2

21-3

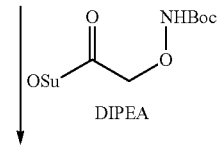

DIPEA

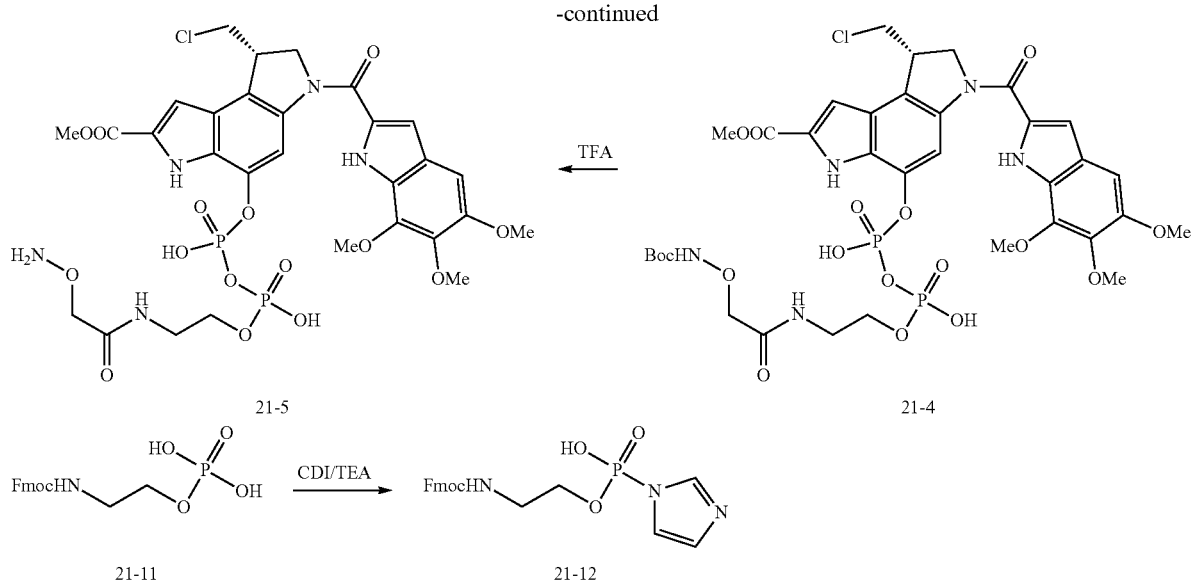

Step A: (S)-methyl 8-(chloromethyl)-4-(phosphonooxy)-6-(5, 6,7-trimethoxy-1H-indole-2-carbonyl)-3, 6,7,8-tetrahydropyrrolo[3,2-e]indole-2-carboxylate (21-2)

Duocarmycin 21-1 (85.0 mg, 0.165 mmol) was dissolved in THF/acetonitrile (3 mL/3 mL) and treated with phosphoryl chloride (0.139 mL, 1.49 mmol) and diisopropylethyl amine (0.144 mL, 0.825 mmol) with ice-water bath cooling. The reaction was kept at the same temperature for 1 h and sodium phosphate monobasic solution (1M, 10 mL) was added and kept the mixture at 4° C. overnight. The mixture was then subjected to the RP-HPLC purification (Phenomenex Gemini-NX C18 5 μm 100×30 mm; MeCN/water with 0.05% TFA) to obtain compound 21-2 (55 mg, %). MS m/z 594 (M+H)$^+$.

Step B: (8S)-methyl 4-(((2-aminoethoxy) (hydroxy) phosphoryloxy) (hydroxy)phosphoryloxy)-8-(chloromethyl)-6-(5,6, 7-trimethoxy-1H-indole-2-carbonyl)-3, 6,7, 8-tetrahydropyrrolo[3, 2-e]indole-2-carboxylate (21-3)

A solution of (9H-fluoren-9-yl)methyl 2-(phosphonooxy) ethylcarbamate (68.0 mg, 0.185 mmol) in DMF (1.5 mL) was treated with carbonyldiimidazole (90.0 mg, 0.558 mmol) and triethylamine (25.0 μL, 0.186 mmol) at room temperature for 3 h. A drop of MeOH was added and stirred at room temperature for 10 min. The volatile was completely removed and co-evaporated with toluene. The residue was dissolved in DMF (1.85 mL) and compound 21-2 (55.0 mg, 0.093 mmol) was added. The mixture was kept room temperature for 19 h and then treated with diethylamine at room temperature for 4 min. The reaction was immediately purified by RP-HPLC (Phenomenex Gemini NX C18 5 μm 100×30 mm; MeCN/water with 0.05% TFA) to obtain compound 21-3 TFA salt (19 mg, 14%). MS m/z 717 (M+H)$^+$.

Step C: (8S)-methyl 8-(chloromethyl)-4-(((2, 2-dimethyl-4, 8-dioxo-3, 6-dioxa-5, 9-diazaundecan-11-yloxy) (hydroxy)phosphoryloxy) (hydroxy)phosphoryloxy)-6-(5,6, 7-trimethoxy-1H-indole-2-carbonyl)-3, 6,7, 8-tetrahydropyrrolo[3, 2-e]indole-2-carboxylate (21-4)

A solution of 21-3 (16 mg, 0.019 mmol) in dichloromethane (2 mL) was treated with 2,5-dioxopyrrolidin-1-yl 2-(tert-butoxycarbonylaminooxy)acetate (11.0 mg, 0.038 mmol) and triethylamine (10.1 μL, 0.076 mmol) at 0° C. for 10 min. The reaction mixture directly purified by RP-HPLC (Phenomenex Gemini-NX C18 5 μm 100×30 mm; MeCN/ water with 0.05% TFA) to obtain a white powder 21-4 (14 mg, 83%). MS m/z 890 (M+H)$^+$.

Step D: (8S)-methyl 4-(((2-(2-(aminooxy)acetamido)ethoxy) (hydroxy)phosphoryloxy) (hydroxy) phosphoryloxy)-8-(chloromethyl)-6-(5, 6, 7-trimethoxy-1H-indole-2-carbonyl)-3, 6, 7, 8-tetrahydropyrrolo[3, 2-e]indole-2-carboxylate (21-5)

Compound 21-4 (14 mg, 0.0157 mmol) was dissolved in dichloromethane (1 mL) and treated with TFA (0.2 mL) for 20 min. The reaction mixture was concentrated in vacuum and co-evaporated with toluene (0.5 mL×2). The residue was purified by RP-HPLC (Phenomenex Gemini-NX C18 5 μm 100×30 mm; MeCN/water with 0.05% TFA) to obtain the target compound 21-5 (Duocarmycin-405) as TFA salt (5.5 mg, 39%). $^1$H-NMR (500 MHz, CDCl$_3$/MeOH-d4) δ 8.28 (br, 1H), 7.21 (s, 1H), 7.02 (s, 1H), 6.95 (s, 1H), 4.77 (2H buried in solvent peak), 4.58 (bs, 1H), 4.39 (m, 1H), 4.06-3.75 (m, 11H), 3.5 (m, 2H). MS m/z 790 (M+H)$^+$.

Example 22

The solubility of exemplary drug-linker conjugates in aqueous solutions was evaluated. Linkers utilized in drug conjugates may have aqueous solubility to enable conjugation in aqueous media amenable to protein solubilization. Furthermore, linkers with aqueous solubility are considered hydrophilic, and may confer to the drug conjugate a reduced propensity to aggregate relative to standard hydrophobic linkers in the literature. The following exemplary drug-linkers were tested in an aqueous solution comprising 20% acetonitrile (MeCN/H$_2$O) for solubility at a concentration of 10 mg/mL. As shown in Table 1, the exemplary linker-drug conjugates displayed high solubility, which may be a result of the contribution of the polarity and charge of the phosphate containing linker to the drug-linker conjugate.

TABLE 1

| Drug Linker | Measured Solubility in 20% MeCN/H$_2$O |
|---|---|
| 1-4 | >10 mg/mL |
| 2-7 | >10 mg/mL |
| 3-4 | >10 mg/mL |
| 4-3 | >10 mg/mL |
| 5-3 | >10 mg/mL |

Example 23

In Vitro Stability Studies of Exemplary Drug-Linkers in Blood and Lysosomal Lysates.

Exemplary dexamethasone-linkers 4-3, 5-3, 1-4, 3-4, and 2-7 were incubated in relevant biomatrices to measure their stability and propensity to release free drug (Tables 2 to 4).

The exemplary dexamethasone-linkers were studied for their stability (Table 1) and propensity to release dexamethasone (Table 2) in human blood. As shown in the tables, all the dexamethasone linkers were stable in blood with little detectable degradation or release of free dexamethasone.

TABLE 1

Time Course of Calculated Conc. for each compound in human whole blood (nM)

| Matrix | Time | Dexamethasone | 4-3 | 5-3 | 1.4 | 3-4 | 2-7 |
|---|---|---|---|---|---|---|---|
| | Matrix spiking | 2939 | 2821 | n/a | 3059 | n/a | 1059 |
| | 0 m | 1687 | 1539 | 1299 | 1617 | 1382 | 1040 |
| | 5 m | | | 1251 | | 1325 | |
| | 10 m | | | | | | |
| | 15 m | | | 1276 | | 1398 | |
| | 20 m | 2409 | 1861 | | | | 1390 |
| | 30 m | | | 1111 | | 1250 | |
| | 1 hr | 2224 | 1619 | 937 | 1421 | 1141 | 1515 |
| | 2 hr | | | 1480 | | 1703 | |
| | 3 hr | 1502 | 1677 | | | | 1899 |
| | 6 hr | 2792 | 2040 | | 1400 | | 123 |

TABLE 2

Time Course of Calculated Conc. for dexamethasone in human whole blood (nM)

| Matrix | Time | Dexamethasone | 4-3 | 15-3 | 1.4 | 3-4 | 2-7 |
|---|---|---|---|---|---|---|---|
| | Matrix spiking | 2939 | 4 | 0 | 2 | 0 | 0 |
| | 0 m | 1687 | 0 | 0 | 0 | 0 | 0 |
| | 5 m | | | 0 | | 0 | |
| | 10 m | | | | | | |
| | 15 m | | | 0 | | 0 | |
| | 20 m | 2409 | 0 | | | | 0 |
| | 30 m | | | 0 | | 0 | |

TABLE 2-continued

Time Course of Calculated Conc. for dexamethasone in human whole blood (nM)

| Matrix | Time | Dexamethasone | 4-3 | 15-3 | 1.4 | 3-4 | 2-7 |
|---|---|---|---|---|---|---|---|
| | 1 hr | 2224 | 0 | 0 | 0 | 0 | 0 |
| | 2 hr | | | 0 | | 0 | |
| | 3 hr | 1502 | 1 | | | | 0 |
| | 6 hr | 2792 | 3 | | 0 | | 0 |

General Experimental Procedure

Human Blood Incubation

Human blood was collected the morning of the experiment from at least 3 individuals using K2EDTA as the anticoagulant. An equal volume from each individual was combined for use in the experiment. The experiment started no more than 2 hours after the blood collection. All drug-linker conjugates were solubilized in DMSO to form each 10 mM stock solution. Dosing solution for each linker was prepared by serial dilution of each stock solution using 1:3 acetonitrile:water. All solutions were kept on ice during the experiment.

Human blood was pre-warmed in a 37° C. water bath in an appropriate volume to collect samples over a time course from 0 through 6 hours. Incubating blood was mixed well just prior to sampling to give a homogenous mixture. Aliquots of blood were removed at appropriate time points, added to cold stopping solution, which was methanol containing an appropriate internal standard, and mixed rigorously. The samples were centrifuged at 4000 RPM for 10 minutes after which equal volumes of the supernatant fractions were diluted with cold deionized water. The samples were then ready for analysis. A time 0 sample was prepared by spiking blood, which had been pretreated with the same stopping reagent used above with the drug-linker. This sample is referred to in the tables as the matrix spiking.

Representative dexamethasone-linkers 4-3, 5-3, 1-4, 3-4, and 2-7 were studied for their stability (Table 4) and propensity to release dexamethasone (Table 5) in purified rat liver lysosomal lysates. Tables 4 and 5 show that the different dexamethasone-linkers released dexamethasone at different rates depending on the structure of the tuning element. For example, 3-4 was no longer detectable after 10 minutes incubation in the rat lysosomal extract whereas for 4-3 and 5-3 the dexamethasone was more slowly released with 5-3 releasing dexamethasone faster than 4-3.

TABLE 3

Time Course of Calculated Conc. for each compound in rat lysosomal lysate (nM)

| Matrix | Time | Dexamethasone | 4-3 | 5-3 | 1.4 | 3-4 | 2-7 |
|---|---|---|---|---|---|---|---|
| | Matrix spiking | 2059.0 | 1590.7 | 2555.29 | 2487.3 | 3128.83 | 2228 |
| | 0 m | 1456.4 | 888.8 | 1394.08 | 1148.2 | 1252 | 1327 |
| | 5 m | 1851.2 | 1156.1 | 1295.86 | 158.2 | 501.28 | 56 |
| | 10 m | 1640.8 | 983.4 | 1278.4 | 19.0 | 149.18 | 512 |
| | 15 m | 1666.7 | 1032.6 | 1407.73 | 3.7 | N/A | 0 |
| | 30 m | 1602.6 | 980.1 | 1175.39 | N/A | N/A | 37 |
| | 1 hr | 1576.8 | 882.4 | 970.65 | N/A | N/A | 0 |
| | 2 hr | 1681.0 | 880.1 | 743.45 | N/A | N/A | 0 |
| | 3 hr | 1689.7 | 903.8 | 500.41 | N/A | N/A | 0 |
| | 6 hr | 1689.8 | 858.9 | 221.03 | N/A | N/A | 0 |

TABLE 4

Time Course of Calculated Conc. for dexamethasone in rat lysosomal lysate (nM)

| Matrix | Time | Dexamethasone | 4-3 | 5-3 | 1.4 | 3-4 | 2-7 |
|---|---|---|---|---|---|---|---|
| Matrix spiking | | 2059.0 | N/A | N/A | N/A | N/A | 17 |
| | 0 m | 1456.4 | 0.9 | N/A | 4.7 | 15.74 | 44 |
| | 5 m | 1851.2 | 14.5 | 10.25 | 320.7 | 100.44 | 415 |
| | 10 m | 1640.8 | 14.2 | 21.56 | 559.4 | 209.07 | 682 |
| | 15 m | 1666.7 | 22.3 | 31.68 | 831.7 | 285.67 | 808 |
| | 30 m | 1602.6 | 28.9 | 78.6 | 1059.6 | 425.28 | 1039 |
| | 1 hr | 1576.8 | 41.6 | 162.45 | 1148.8 | 526.5 | 1159 |
| | 2 hr | 1681.0 | 72.5 | 290.66 | 854.5 | 534.84 | 1309 |
| | 3 hr | 1689.7 | 90.2 | 379.36 | 841.9 | 584.61 | 1207 |
| | 6 hr | 1689.8 | 141.9 | 550.43 | 826.6 | 561.88 | 1155 |

General Experimental Procedure
Rat Lysosome Incubation.

Rat Liver lysosomes were available commercially with a pool of 6 animals. All linker compounds were solubilized in DMSO to form each 10 mM stock solution. Dosing solution for each linker was prepared by serial dilution of each stock solution using 1:3 acetonitrile:water. All solutions were kept on ice during the experiment.

Rat lysosomes were pre-warmed in a 37° C. water bath in an appropriate volume to collect samples over a time course from 0 minutes through 6 hours. Incubating lysosomes were mixed well just prior to sampling to give a homogenous mixture. Aliquots of lysosomes were removed at appropriate time points, added to cold stopping solution, which was methanol containing an appropriate internal standard, and mixed rigorously. The samples were centrifuged at 4000 RPM for 10 minutes after which equal volumes of supernatant were diluted with cold deionized water. The samples were ready for analysis. A time 0 sample was prepared by spiking the drug-linker to lysosomes which had been pre-treated with the same stopping reagent as above. This sample is referred to as matrix spiking in the tables.

LIQUID Chromatography—Tandem Mass Spectrometry Analysis

A Thermo LX-2 ultra-performance liquid chromatography system coupled with a Sciex API5000 triple quadrupole mass spectrometer was used for the analysis. The payload and drug-linkers were retained and separated by a C18 column and detected by the mass spectrometer. The standard curve for each analyte was prepared to obtain the quantitative results. Samples were kept in cold stack set at 5° C.

Example 24

Synthesis, Purification and Analysis of ADC Using Exemplary Drug-Linker 1-4

To establish the chemical reactivity of this linker design to form a drug conjugate, exemplary drug-linker 1-4 was conjugated to an anti-mouse CD25 antibody (IgG1) (mCD25) to produce antibody-drug conjugate ADC 12-1 or anti-human CD70 antibody 2H5 antibody (hCD70) to produce ADC 12-2. Specifically, the drug-linker was conjugated to the unnatural amino acid para-azido-phenylalanine (pAF) replacing the alanine at position 1 of CH1 of the antibody using copper-free 3+2 cycloaddition chemistry as shown in FIG. 1. The amino acid sequence of the anti-mouse CD25 heavy chain comprising the pAF at position 115 is shown in SEQ ID NO:3 and the amino acid sequence of the light chain is shown in SEQ ID NO:4. The amino acid sequence of the anti-human CD70 heavy chain comprising pAF at position 119 is shown in SEQ ID NO:1 and the amino acid sequence of the light chain is shown in SEQ ID NO:2. Synthesis of antibodies containing an unnatural amino acid has been described in U.S. Pat. No. 7,632,924, incorporated herein by reference, and copper-free 3+2 cycloaddition chemistry has been described in U.S. Pat. No. 7,807,619, incorporated herein by reference. Conjugation, purification, and analysis confirmed synthesis of the Anti-CD25 antibody-drug conjugate ADC 12-1 and the anti-CD70 ADC 12-2.

Experimental for Conjugation of Phosphate Linker 1-4 to Anti-Mouse CD25

Antibodies were purified over protein A column (NovaSep) followed by SP 650S column (Tosoh Biosciences).

Site Specific Conjugation Using Click (2+3) Chemistry.

Para-azido phenylalanine containing antibodies were buffer exchanged into 50 mM Histidine; 100 mM NaCl; 2.5% Trehalose; 0-20% Dimethylamine, pH 6.0 and concentrated to 1-20 mg/mL. 10-15 molar equivalents of cyclooctyne drug-linker were added and reacted for 16-72 hours at 28-30° C. The antibody conjugates were purified over a SP 650S column (Tosoh Biosciences) to remove excess reagents. The conjugates were buffer exchanged into 50 mM Histidine; 100 mM NaCl; 2.5% Trehalose; pH 6.0, 0.22 μm filtered, and stored at 4° C.

Site Specific Conjugation Using Oxime Chemistry.

Para-acetyl phenylalanine (pAcF) containing antibodies were buffer exchanged into 50 mM sodium acetate; 2.5% trehalose; 0-20% Dimethylamine, pH 4.0-4.5 and concentrated to 1-20 mg/mL. 10-15 molar equivalents of aminooxy drug-linker were added and reacted for 16-72 hours at 28-30° C. The antibody conjugates were purified over a SP 650S column (Tosoh Biosciences) to remove excess reagents. The conjugates were buffer exchanged into 50 mM Histidine; 100 mM NaCl; 2.5% Trehalose; pH 6.0, 0.22 μm filtered, and stored at 4° C.

Conjugation Analysis.

Conjugation efficiency and DAR values were determined by reversed phase HPLC. The ADC was run over a Zorbax 300SB-C3 column, 4.6×150 mm (Agilent) at 80° C. and eluted with a linear gradient from 30% B to 90% B (A: water, 0.1% TFA; B: acetonitrile, 0.1% TFA). An Agilent 1200 series HPLC system and Chemstation software were used to resolve and quantify percentage of antibody conjugated with drug-linker.

Example 25

Serum Stability of ADC 12-1

Figure 2:
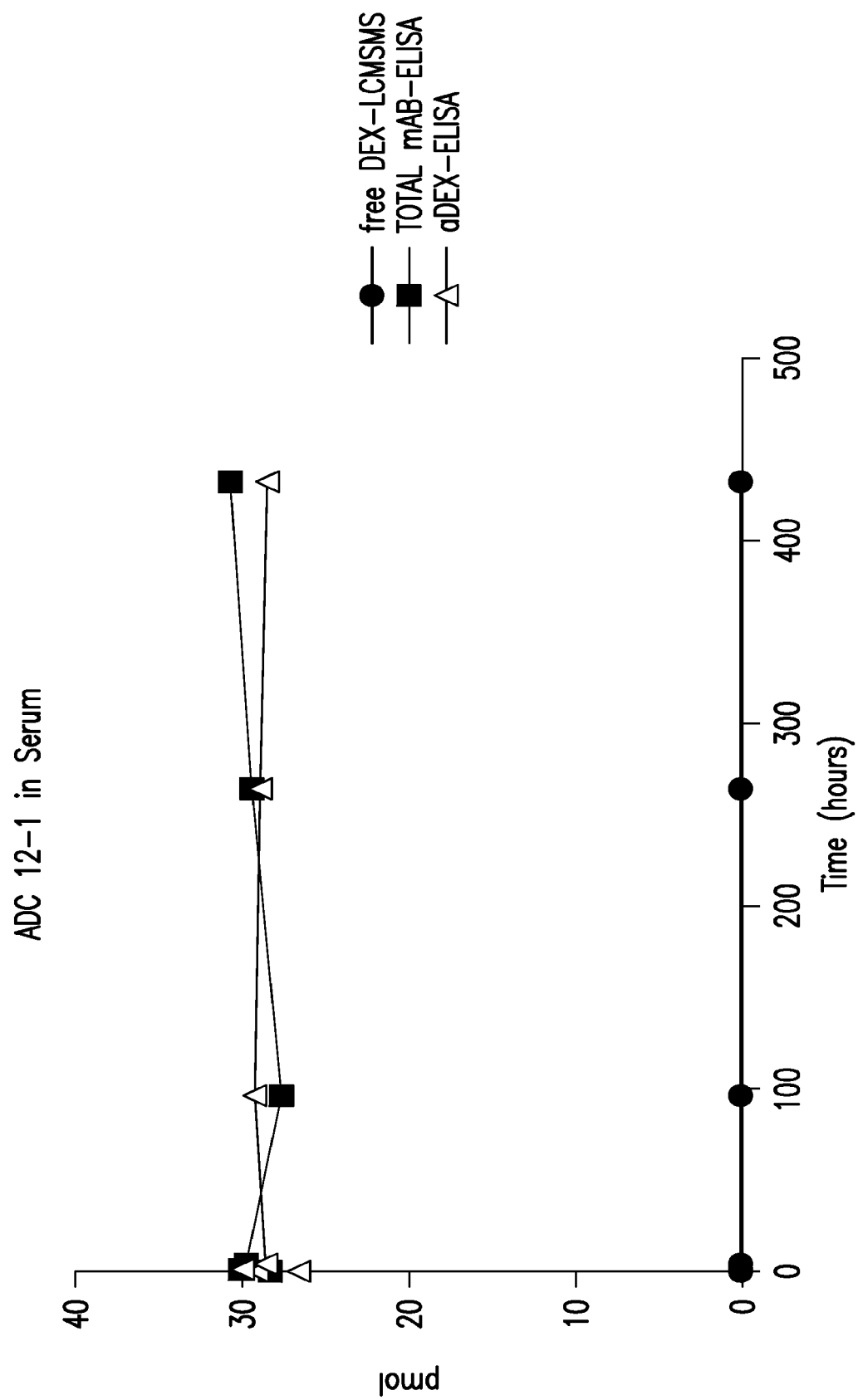
FIG. 2 is a graph showing stability of ADC 12-1 in mouse serum. (aDEX is ADC 12-1).

Drug conjugates may be designed with a stable linker to ensure that the attached payload adopts the pharmacokinetic properties of the carrier. In the example of antibody drug conjugates, premature release of the payload will reduce the total payload delivered to a target cell. To establish the potential for circulatory stability of this linker design in the context of a drug conjugate, ADC 12-1 was incubated in mouse serum and monitored for degradation or loss of payload (dexamethasone). As shown in FIG. 2, no measurable loss of dexamethasone was observed over three weeks incubation in serum.

In Vitro Stability Study Design in DBA1 Mice Serum

For the in vitro stability study, the ADC 12-1 was spiked in DBA1 mice serum at 0.1 mg/mL. Samples were sealed under nitrogen, placed at 37° C. in a cell culture incubator and stored at −80° C. until analysis. Time points from 0 min to 21 days of incubation were evaluated.

In Vitro Stability—Free Payload Analysis

Samples were evaluated for free dexamethasone by LC-MS/MS. For the in vitro stability study, 40 µL of serum for each time point underwent protein precipitation with 400 µL acetonitrile containing dexamethasone-d4 (internal standard). Tubes were centrifuged at 14000 RPM (4° C.) for 10 minutes and the supernatant fraction removed and dried in a speed vac. Samples were reconstituted with methanol/water (50/50) and injected in an Acquity/TSQ Vantage triple quad mass spectrometer equipped with an Xbridge C18 column (Waters, Milford). Mobile phases consisted of buffers A (water:acetonitrile:formic acid, 95:5:0.1%) and B (acetonitrile:water:formic acid, 80:20:0.1%) and a linear gradient was performed with buffer B increasing from 30 to 65% in 3 minutes. Flow rate was set at 0.3 mL/minutes. Transitions for acetate adduct of dexamethasone and dexamethasone d-4 were 437>361 and 441>363, respectively. Compounds were detected using negative electrospray ionization. Free dexamethasone was not be detected in the in vitro stability serum samples over the period evaluated.

In Vitro Stability—Immunoprecipitation Coupled to Intact Mass Analysis

ADC 12-1 was pulled down from mice serum using immunoprecipitation (IP) with streptavidin magnetic beads (Dynabeads M-280) coupled to biotinylated CD25 (antigen). Beads were washed 3 times with 100 µL of TBS 1×. Two microliters of 1 mg/mL biotinylated CD25 was added to 30 µL of each sample (serum from each time point) and incubated for 10 minutes at room temperature (RT). Samples were added to the pre-washed beads and incubated for 30 minutes at RT under gentle shaking. The flow through was discarded and beads were washed twice with 0.02% Rapigest in TBS 1×. Elution was performed with 30 µL of TFA 0.1% and 5 µL of each sample was analyzed in an UPLC/Synapt G2-S(Waters, Milford) equipped with a POROS column (ABSciex) using reverse phase gradient.

Figure 3:
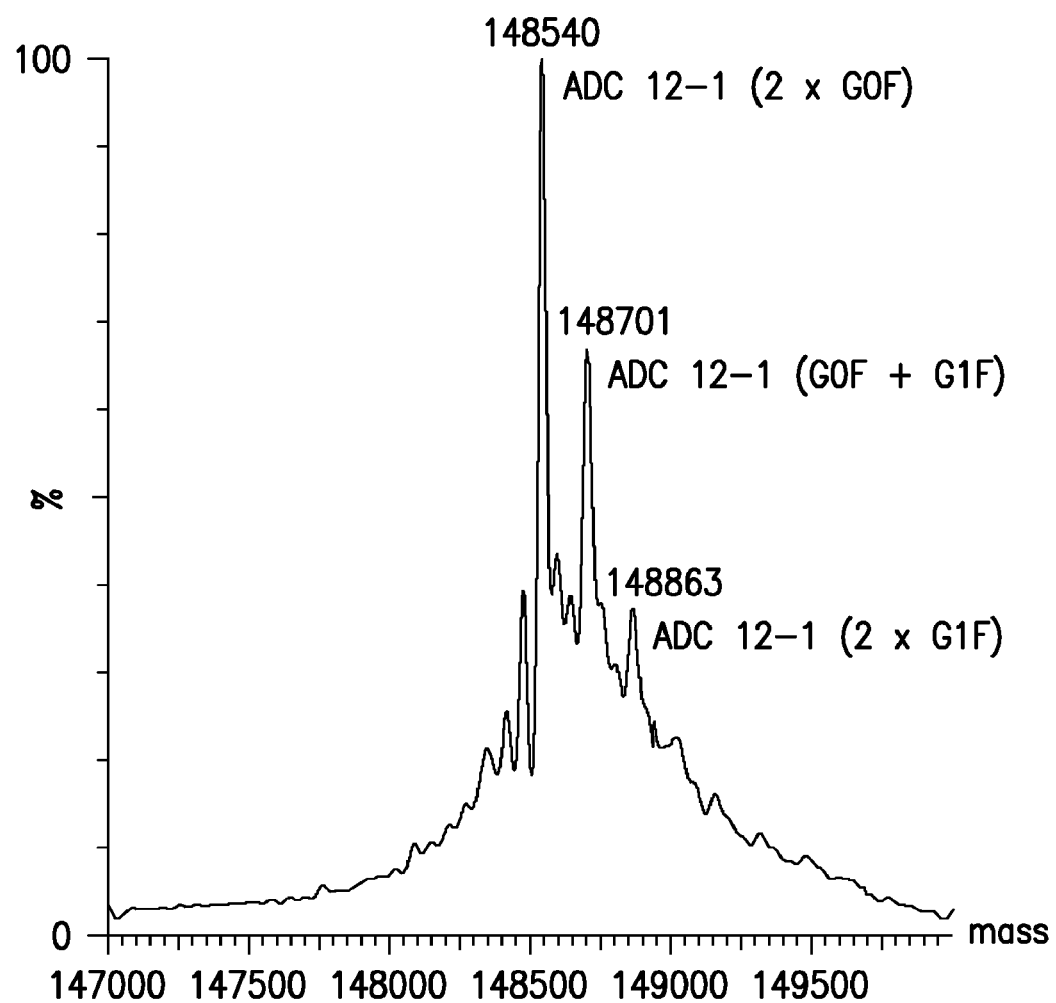
FIG. 3 is a graph showing deconvoluted intact mass spectrum for ADC 12-1 stock solution.
Figure 4A:
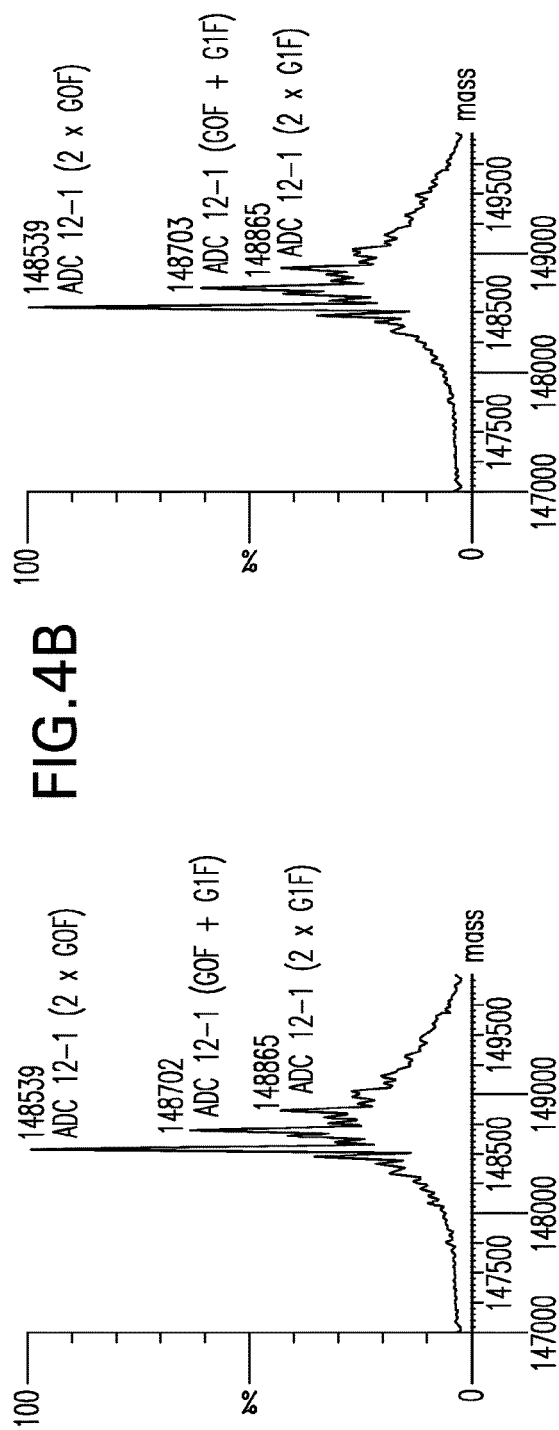
FIG. 4 is a graph showing deconvoluted intact mass spectra for in-vitro stability samples of ADC 12-1. incubated at 37° C. for: A) 1 hour, B) 8 hours, C) 14 days and D) 21 days.
Figure 4B:
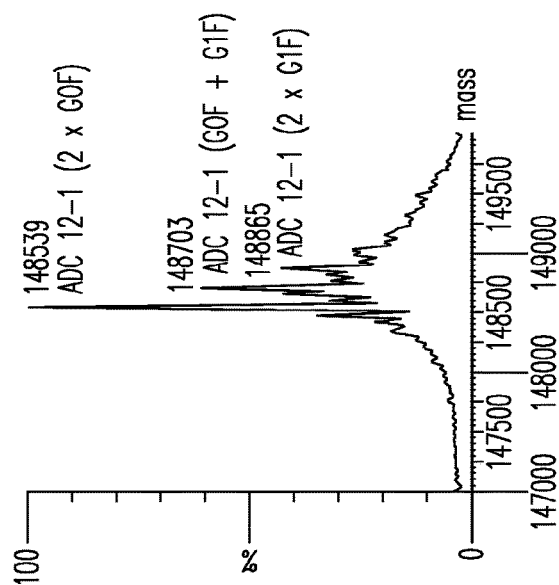
Figure 4C:
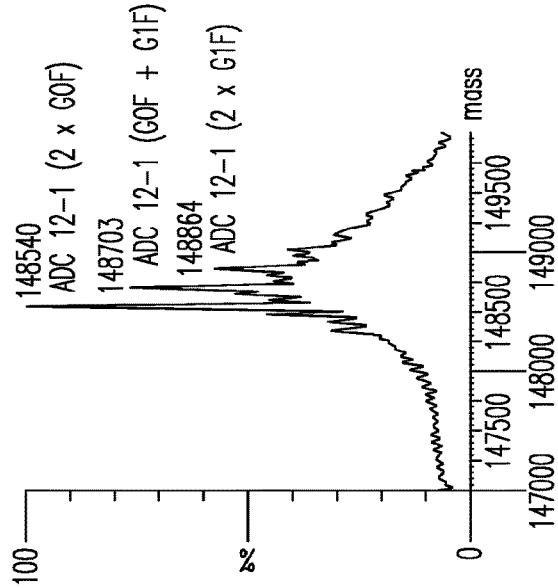
Figure 4D:
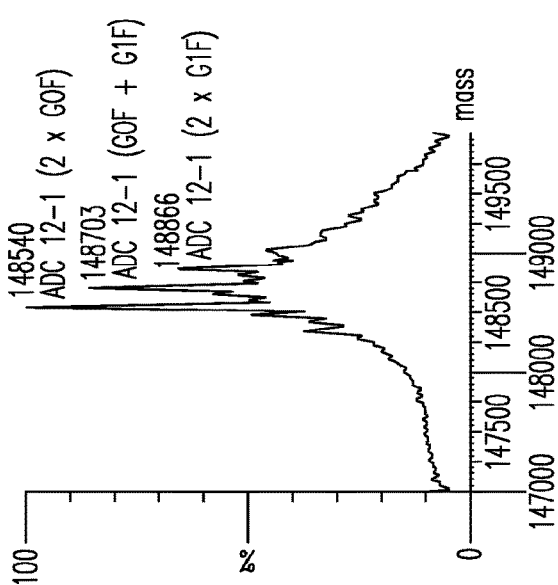

Spectra deconvolution was performed using MaxEnt1 software (Waters, Milford) and results were compared against the intact mass obtained for the ADC from a stock solution (FIG. 3). FIG. 3 shows a deconvoluted intact mass spectrum for the ADC 12-1 stock solution. G0F, G1F and G2F in the figure refer to the carbohydrate isoforms on the antibody portion of the antibody-drug conjugate.

The deconvoluted spectra of the stock solution (FIG. 3) revealed that the antibody-drug conjugate 12-1 intact mass in its predominant DAR 2 form contained two G0F sugar motifs. Additional peaks at about 162 Da apart showed two other glycoforms containing G0F/G1F (peak at 148701 Da) and 2×G1F (peak at 148863 Da). The glycan profile is typical of that for an IgG.

FIG. 4 shows the deconvoluted spectra of time points 1 hour, 8 hours, 14 days and 21 days from the in vitro stability study. The data analysis showed that no significant mass change occurred for the ADC over the incubation period evaluated in the study (Table 6: intact mass results for the in-vitro stability study).

TABLE 6

| In vitro Stability | |
|---|---|
| MW of the ADC 12-1 (2×G0F form) | Incubation Time |
| 148539 | 1 hour |
| 148539 | 8 hours |
| 148539 | 2 days |
| 148539 | 3 days |

TABLE 6-continued

| In vitro Stability | |
|---|---|
| MW of the ADC 12-1 (2×G0F form) | Incubation Time |
| 148540 | 7 days |
| 148540 | 14 days |
| 148540 | 21 days |

In Vivo Stability of ADC 12-1

Effective linker designs will not only provide stable tethering to a carrier in drug conjugates, but should also have minimal to no effect on the pharmacokinetic properties of the carrier itself. To establish the potential of this linker design for in vivo circulatory stability and to understand its impact on the pharmacokinetics of the conjugated carrier in the context of a drug conjugate, ADC 12-1 was dosed to DB1 mice and was monitored for degradation of the mAb, intactness of the antibody-drug conjugate, and loss of payload (dexamethasone). Importantly, the study showed that the inherent pharmacokinetics of naked (non-conjugated) anti-mouse CD25 was not adversely affected by the conjugation of two molecules of drug-linker 1-4 to the antibody. Furthermore, the study showed that no loss of drug linker and no measurable dexamethasone were observed over the course of the 5 day study. The data shows that drug-linker 1-4 was stable in circulation and retained payload on the carrier in this example of an antibody-drug conjugate.

In Vivo Pharmacokinetic (PK)/Stability Study

General Experimental for In Vivo PK Study of ADC 12-1

Figure 5:
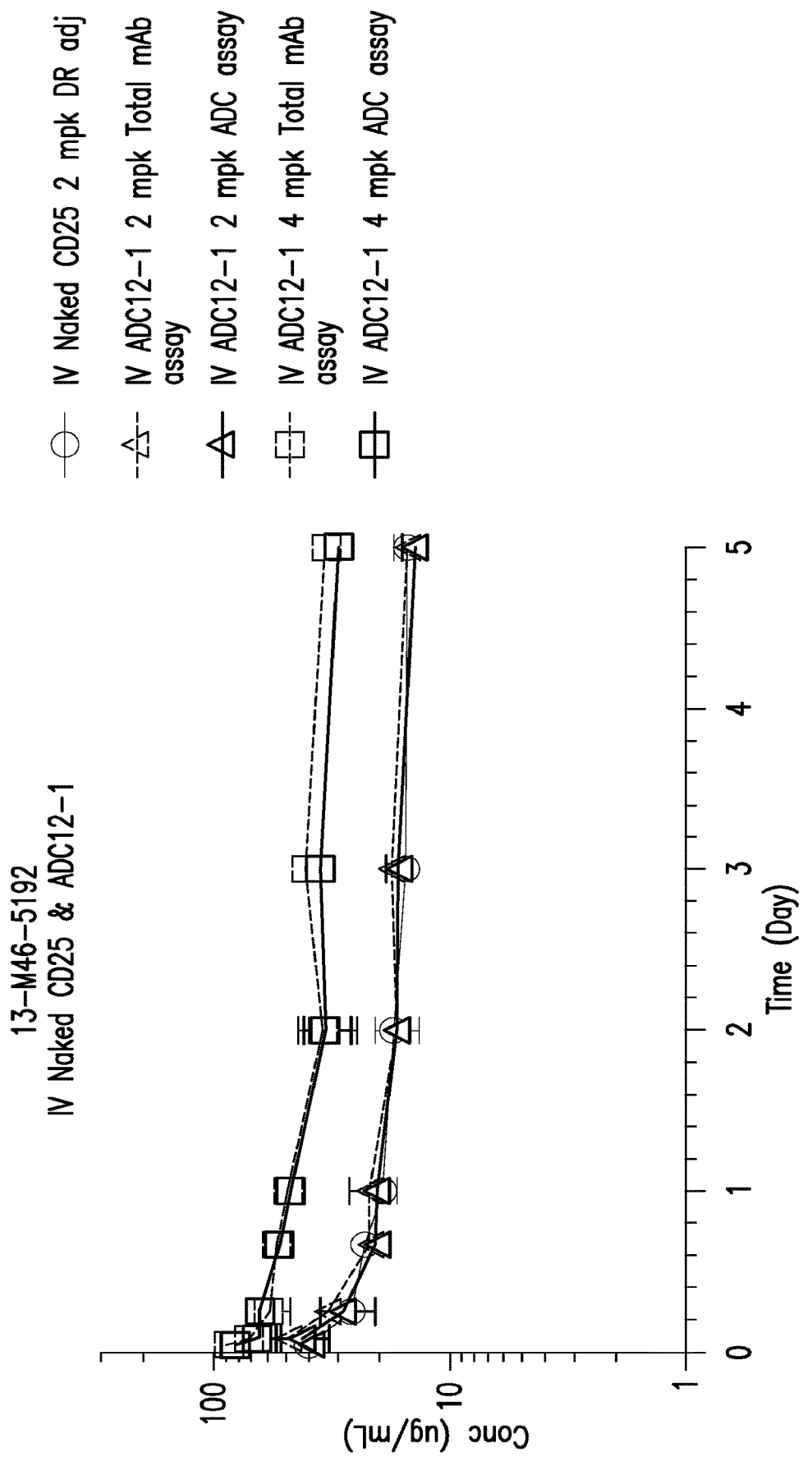
FIG. 5 is a graph showing In vivo stability of ADC 12-1 versus "naked" antibody (non-conjugated) following IV dosing to DBA1 mice.
Figure 6A:
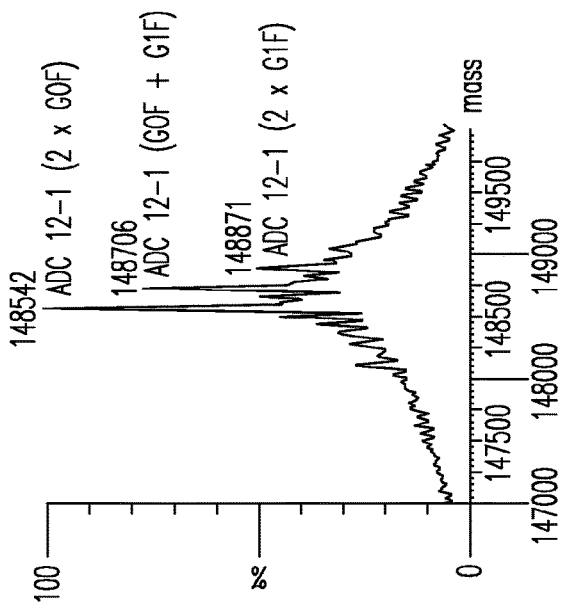
FIG. 6 is a graph showing deconvoluted intact mass spectra for the in vivo stability samples of ADC 12-1 from FIG. 5: A) sample B1 at 1 hour, B) sample H3 at 5 days, C) sample B7 at 1 hour and D) sample H9 at 5 days.
Figure 6B:
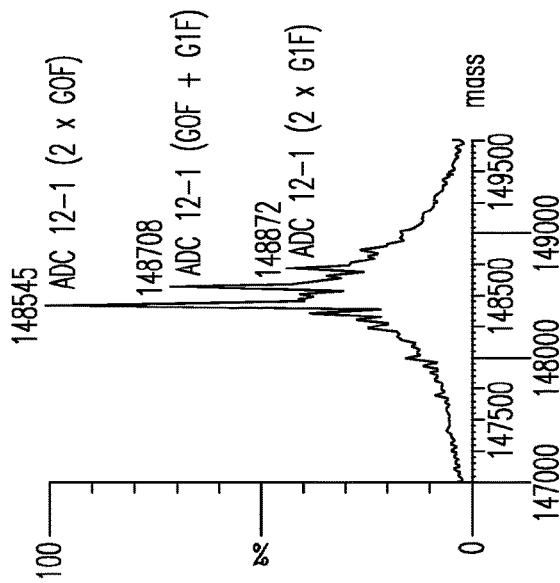
Figure 6C:
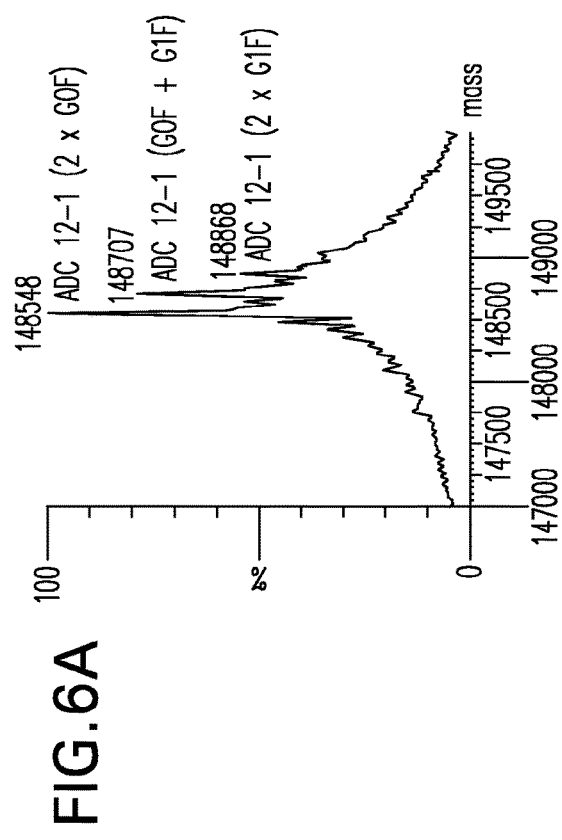
Figure 6D:
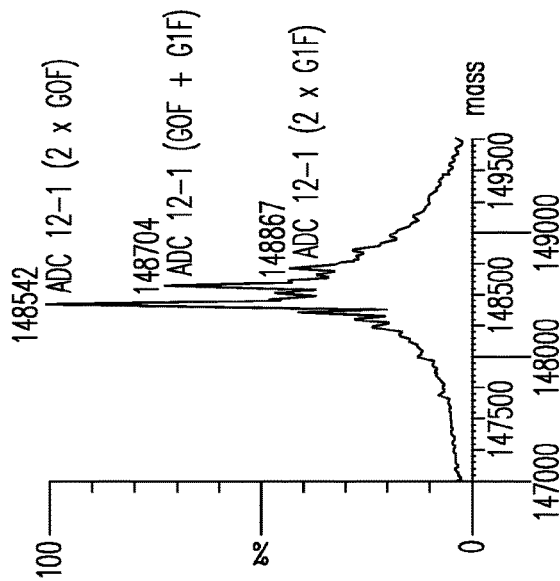

An in vivo study in DBA1 mice was performed in order to evaluate stability and pharmacokinetics of ADC 12-1. Naked antibody was administered intravenously in a single bolus to all groups. Group 1 was given a dose of 2mpk; Group 2 and Group 3 were dosed 2 and 4 mpk of ADC 12-1, respectively. Plasma samples were taken from all three groups at 1, 2, 6, 16 hrs and 1, 2, 3, 5 days after dosing. At each of these time points, three animals per group were sacrificed to obtain plasma sample. Samples from group 1 were analyzed for total naked antibody contents, samples from groups 2 and 3 were submitted for total antibody, intact antibody and free-payload analysis. FIG. 5 shows the In vivo stability of ADC 12-1 following IV dosing to DBA1 mice.

In Vivo Pharmacokinetic (PK)/Stability Study—Free Payload Analysis

PK study samples were evaluated for free dexamethasone using the method described above. For increased sensitivity, 100 µL of serum from one mice of each time point was submitted to protein precipitation with acetonitrile. Free dexamethasone was not detected in any PK samples.

In Vivo Pharmacokinetic (PK)/Stability Study—Intact Antibody Drug Conjugate Mass Analysis Samples from the ADC 12-1 PK study were also evaluated for stability using immunoprecipitation coupled to intact mass analysis. 50 µL of each sample was processed as described above. The results showed no molecular weight change for the antibody-drug conjugate over the study time range (from 1 hour to 5 days) (FIG. 6, Table 7).

TABLE 7

| In vivo PK/Stability Intact Mass Results | | | |
|---|---|---|---|
| Sample | MW of the 12-1 (2×G0F motif) | PK Group | Time Point |
| B1 | 148548 | G2 | 1 hour |
| C1 | 148547 | G2 | 1 hour |

TABLE 7-continued

In vivo PK/Stability Intact Mass Results

| Sample | MW of the 12-1 (2xG0F motif) | PK Group | Time Point |
|---|---|---|---|
| E1 | 148546 | G2 | 2 hours |
| F1 | 148548 | G2 | 2 hours |
| A2 | 148546 | G2 | 6 hours |
| C2 | 148546 | G2 | 16 hours |
| D2 | 148547 | G2 | 16 hours |
| F2 | 148545 | G2 | 1 day |
| G2 | 148548 | G2 | 1 day |
| A3 | 148546 | G2 | 2 days |
| D3 | 148548 | G2 | 3 days |
| G3 | 148550 | G2 | 5 days |
| H3 | 148542 | G2 | 5 days |
| B7 | 148542 | G3 | 1 hour |
| C7 | 148548 | G3 | 1 hour |
| E7 | 148547 | G3 | 2 hours |
| F7 | 148545 | G3 | 2 hours |
| A8 | 148547 | G3 | 6 hours |
| C8 | 148546 | G3 | 16 hours |
| D8 | 148546 | G3 | 16 hours |
| F8 | 148546 | G3 | 1 day |
| G8 | 148546 | G3 | 1 day |
| A9 | 148544 | G3 | 2 days |
| B9 | 148547 | G3 | 2 days |
| D9 | 148549 | G3 | 3 days |
| E9 | 148550 | G3 | 3 days |
| G9 | 148547 | G3 | 5 days |
| H9 | 148545 | G3 | 5 days |

In Vivo Pharmacokinetic (PK)/Stability Study—Naked/Total mAb Analysis

Plasma samples from in vivo PK study were analyzed for naked Antibody/total Antibody ADC 12-1 concentrations using Meso Scale Discovery (MSD) based electro-chemiluminescence method. The capture reagent is recombinant mouse IL-2R alpha (CD25) for both assays. The detection reagent may be goat anti-rat IgG for naked antibody/total Antibody and anti-dex mAb (e.g., Rabbit polyclonal anti-dexamethasone (Abcam Cat# ab35000)) may be used to detect ADC 12-1, respectively. Briefly, 96 well MSD plates were coated with the capture reagent and then washed. Plates were blocked for 1 hour and washed again. Samples were then added and incubated for 2 hours. Following incubation, plates were washed, incubated with the detection antibody for 1 hour, and washed again. The reading buffer was added and the plates were read using MSD plate reader.

Example 26

The payload-linkers made in Examples 20 and 21 were conjugated to an anti-human Her2 antibody (hHer2) comprising a para-acetyl phenylalanine (pAcF). Methods for making antibodies comprising an unnatural amino acid and conjugating molecules thereto is disclosed in U.S. Pat. No. 7,632,924 to Cho et al., which is incorporated by reference in its entirety.

Site Specific Conjugation Using Oxime Chemistry.

Para-acetyl phenylalanine (pAcF) containing antibodies were buffer exchanged into 50 mM sodium acetate; 2.5% trehalose; 0-20% Dimethylamine, pH 4.0-4.5 and concentrated to 1-20 mg/mL. 10-15 molar equivalents of aminooxy drug-linker were added and reacted for 16-72 hours at 28-30° C. The antibody conjugates were purified over a SP 650S column (Tosoh Biosciences) to remove excess reagents. The conjugates were buffer exchanged into 50 mM Histidine; 100 mM NaCl; 2.5% Trehalose; pH 6.0, 0.22 µm filtered, and stored at 4° C.

Conjugation Analysis.

Conjugation efficiency and DAR values were determined by reversed phase HPLC. The antibody-drug conjugate was run over a Zorbax 300SB-C3 column, 4.6×150 mm (Agilent) at 80° C. and eluted with a linear gradient from 30% B to 90% B (A: water, 0.1% TFA; B: acetonitrile, 0.1% TFA). An Agilent 1200 series HPLC system and Chemstation software were used to resolve and quantify percentage of antibody conjugated with drug-linker.

Cell Assay

Her2 positive SKBR3 and Her2 negative MDA-MD-468 breast adenocarcinoma cell lines (ATCC Manassas, Va., USA) were cultured in DMEM medium supplemented with 10% FBS and 100 µ/mL penicillin, 100 µg/mL streptomycin, or DMEM/F12 supplemented with 10% FBS and 100 µ/mL penicillin, 100 µg/mL streptomycin respectively. The cells were incubated with serial dilutions of Duocarmycin-405 conjugated to anti-Her2 or a non-targeting antibody, Duocarmycin free drug and naked anti-Her2 controls for 6 days. Live cells were measured with CellTiter Glo luminescent cell viability assay kit (Promega, Madison, Wis., USA) and the percentage of live cells determined relative to untreated cells.

Figure 8:
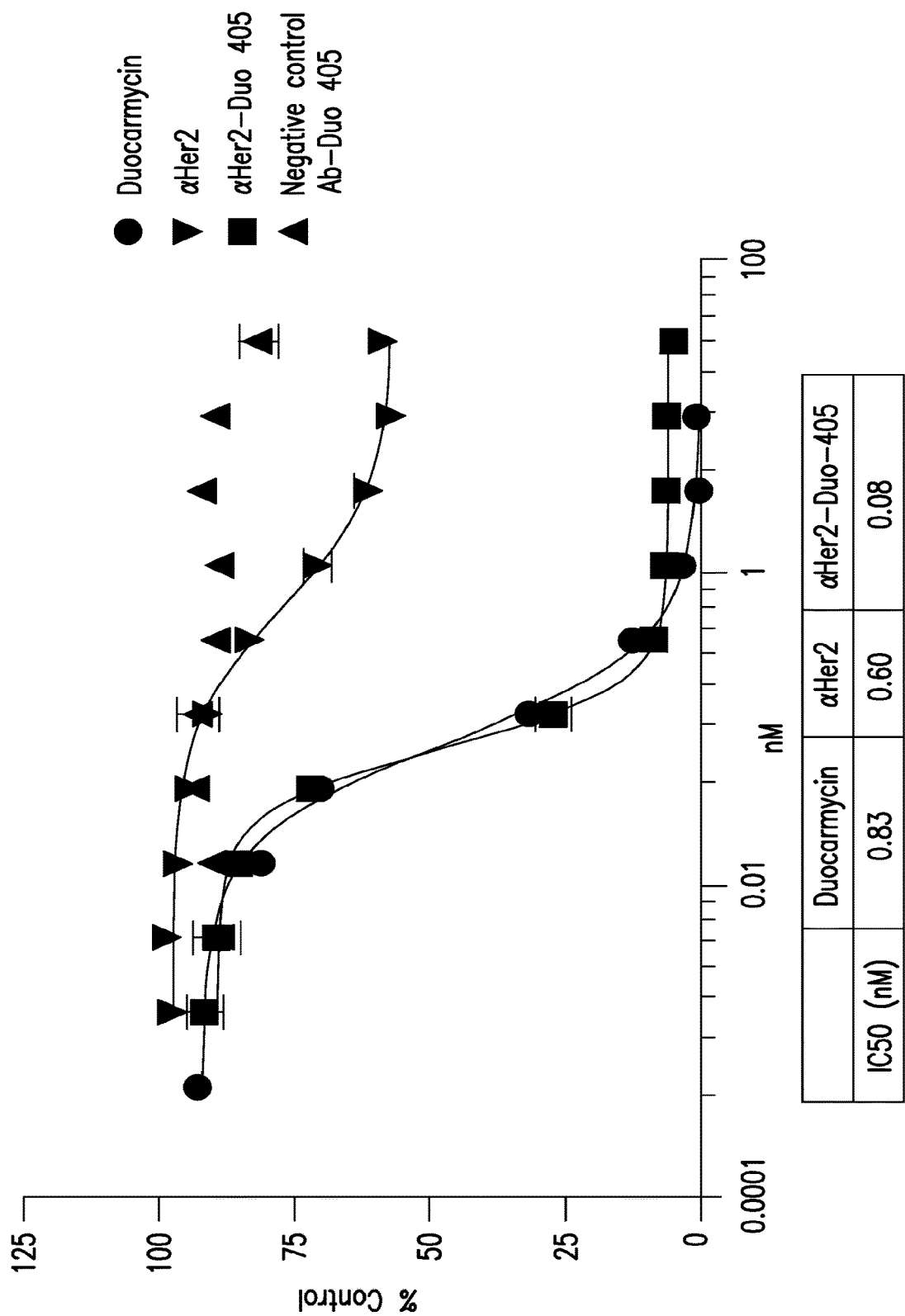
FIG. 8 shows the activity of αHer2-Duo-405 compared to that of a non-targeting antibody conjugated to Duo-405 on Her2 expressing SKBR3 cells.
Figure 9:
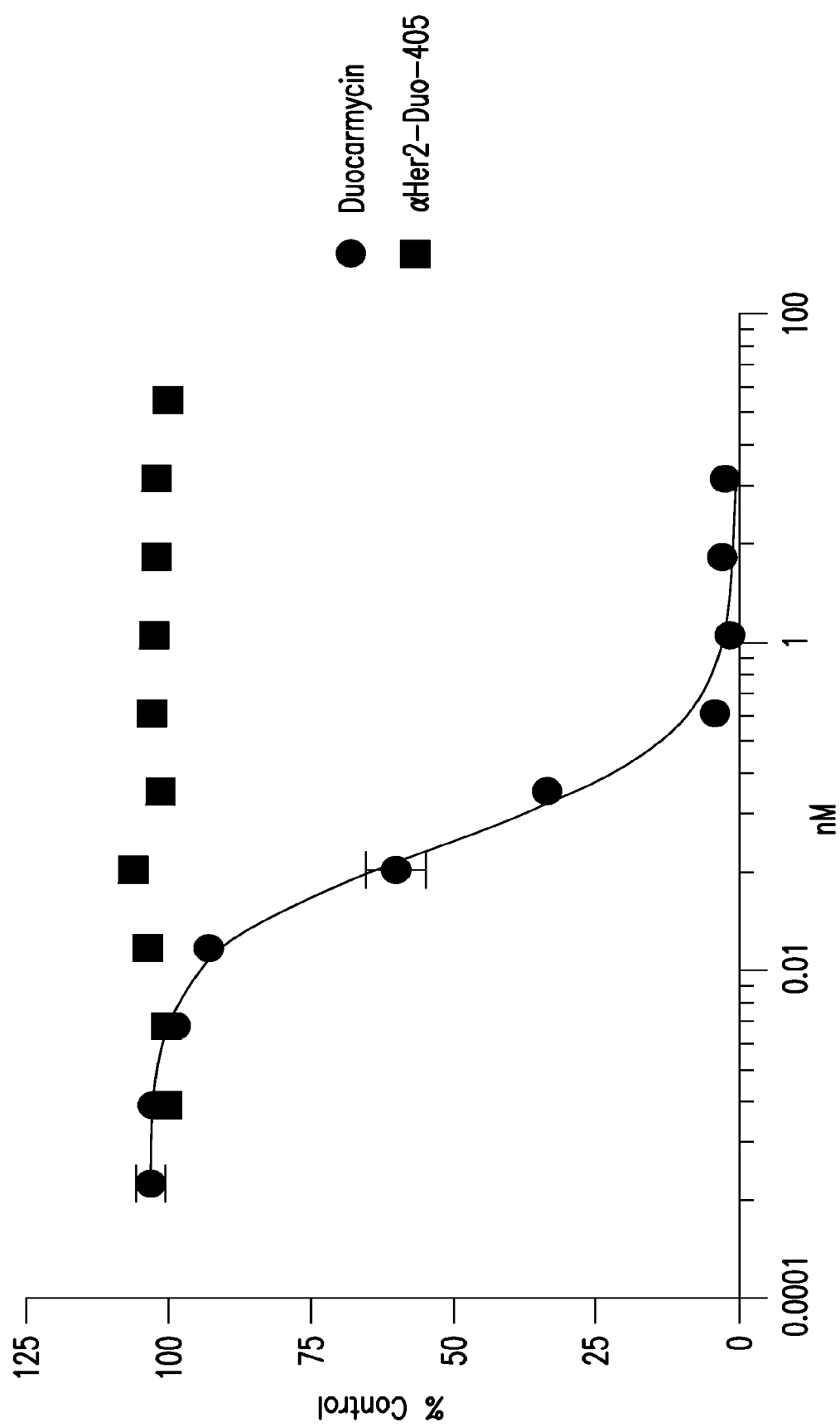
FIG. 9 shows the activity of αHer2-Duo-405 on Her2 negative MDA-MD-468 cells.

The results are shown in FIGS. 8 and 9. FIG. 8 shows that αHer2-Duo-405 was able to deliver its payload to Her2 expressing SKBR3 cells whereas a non-targeting antibody conjugated to Duo-405 was unable to. The Figure shows the specificity of the αHer2-Duo-405 conjugate and its ability to effectively deliver the payload. FIG. 9 shows that αHer2-Duo-405 had no activity on Her2 negative MDA-MD-468 cells.

Example 27

The example shows that conjugates comprising the phosphate-based links have little or no propensity to form aggregates.

Aggregation Assay

An SE-HPLC method was used to conduct the aggregation/% monomer analysis.

An isocratic gradient using 0.2 M potassium phosphate, 0.25 M potassium chloride pH 6.0 was used as the mobile phase at a flowrate of 0.5 mL/min. The column used was a Sepax Zenix-C SEC-300, 3 µm, 300 A, 7.8×300 mm (Cat#233300-7830). Detection of signal was monitored at 214 nm (280 for FIO). For a representative run, the analyte load was 10 µg.

The results are shown in Table 8.

TABLE 8

| Sample Name | Drug-Linker | % High Molecular Weight (aggregate) | % Monomer |
|---|---|---|---|
| mCD25 | Phos-21Dex365 (1-4) | 1.4 | 98.6 |
| hCD70 | Phos-21Dex365 (1-4) | 0.9 | 99.1 |
| hHer2 | Phos-Duo405 (21-5) | 0.5 | 99.5 |

Example 28

Figure 7:
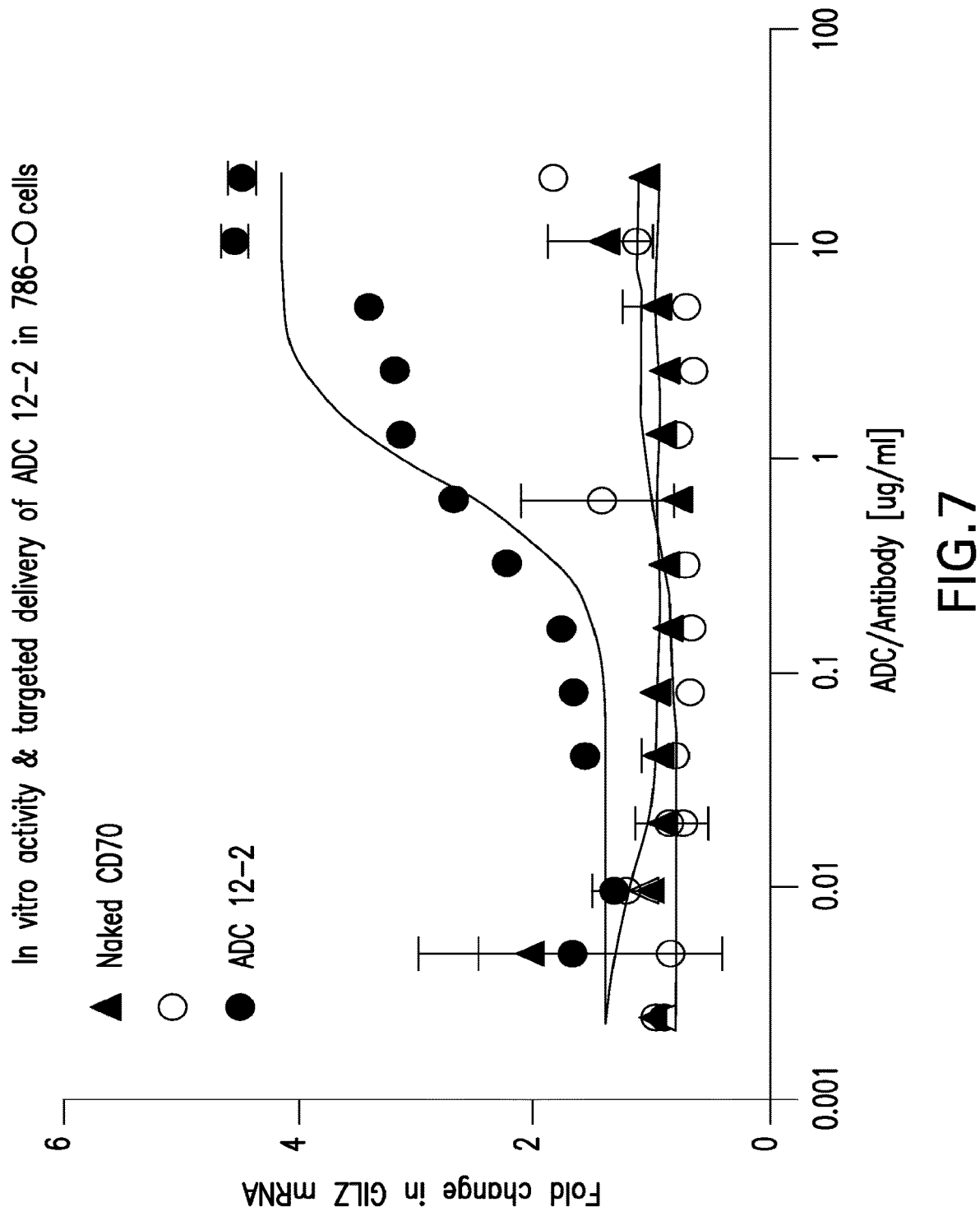
FIG. 7 is a graph showing In vitro activity of ADC 12-2 versus "naked" antibody (non-conjugated) in 786-O cells.

ADC 12-2 (FIG. 1) is anti-CD70 antibody 2H5 conjugated to exemplary drug-linker 1-4 as described in Example 24. In vitro activity and targeted delivery of ADC 12-2, naked antibody, and anti-hexon conjugate control were assessed by transfecting into 786-O (renal cell) and then measuring glucocorticoid-induced leucine zipper (GILZ) mRNA, a widely expressed dexamethasone-induced mRNA transcript. As shown in FIG. 7, ADC 12-2 displayed potent in vitro activity (0.7 ug/ml IP value) in 786-O cells that were confirmed to express CD70. This activity reflects dexamethasone conjugation and targeted delivery as the nonconjugated IgG variant and anti-hexon controls did not induce and observable GILZ in this cell line.

786-O cells were plated at 30K cells/well overnight at 37° C. in RPMI Media as suggested by ATCC (+10% HI FBS). Cells were stimulated with ADCs for 2, 6, or 24 hours at 37° C. Cells were lysed using RLT and RNA is isolated using RNeasy 96 Kits. PCR was used to measure GAPDH, PER1, or TSC22D3

Quantitation of Glucocorticoid-induced leucine zipper (GILZ) mRNA expression was determined as follows. Cellular quantitation of GILZ mRNA was conducted using the following method. Cells suspension were prepared in HBSS+2% FBS (assay buffer) and plated at $5 \times 10^4$ cells per well. Dosing solutions for free drug, ADCs and parental antibodies were prepared by serial dilution of each stock solution using 1:3 in in HBSS+2% FBS supplemented with 1% final concentration of (50 mM Histidine, 100 mM NaCl, 5% Trehalose, pH 6.0), and incubated with cells final concentrations ranging from 20 to 0.002 μg/ml and 100 to 0.0 ng dexamethasone/ml for 18 hours. Cell lysis, cDNA synthesis, and real-time PCR were performed according to manufacturer's instructions using TaqMan Gene Expression Cells-to-$C_T$™ Kit (Invitrogen, Carlsbad, Calif.). Specific primers against human GILZ and GAPDH were purchased from the Life Technologies (Invitrogen, Carlsbad, Calif.). Real-time PCR reactions were performed on the Applied Biosystems 7900 HT Fast Real-Time PCR System. Thermal cycling conditions consisted of an initial UDG incubation hold (50° C., 2 min) denaturing and enzyme activation step (95° C., 2 min) followed by 40 cycles of denaturing (95° C., 15 s), annealing and extending (60° C., 1 min). The mRNA levels were normalized to GAPDH (internal control) using the formula A threshold cycle (CT)=CT target−CT reference. The differential expression signal were expressed as delta Ct (ΔCt) by subtracting the Ct values of the unstimulated samples (containing only assay buffer or DMSO vehicle) from those of the stimulated samples and expressed as relative fold of change using the formula: $2^{\Delta\Delta CT}$.

Table of Sequences

| SEQ ID NO: | Description | Amino Acid Sequence |
|---|---|---|
| 1 | Anti-CD70 2H5 IgG1 X at position 119 is para-azido-phenylalanine (pAF) (CDR 1, 2, and 3 bold type; Fc underlined) | QVQLVESGGGVVQPGRSLRLSC AASGFTFSSYIMHWVRQAPGKG LEWVAVISYDGRNKYYADSVKG RFTISRDNSKNTLYLQMNSLRA EDTAVYYCARDTDGYDFDYWGQ GTLVTVSSXSTKGPSVFPLAPS SKSTSGGTAALGCLVKDYFPEP VTVSWNSGALTSGVHTFPAVLQ SSGLYSLSSVVTVPSSSLGTQT YICNVNHKPSNTKVDKKVEPKS CDKTHTCPPCPAPELLGGPSVF LFPPKPKDTLMISRTPEVTCVV VDVSHEDPEVKFNWYVDGVEVH NAKTKPREEQYNSTYRVVSVLT VLHQDWLNGKEYKCKVSNKALP APIEKTISKAKGQPREPQVYTL PPSRDELTKNQVSLTCLVKGFY PSDIAVEWESNGQPENNYKTTP PVLDSDGSFFLYSKLTVDKSRW QQGNVFSCSVMHEALHNHYTQK SLSLSPG |
| 2 | Anti-CD70 Kappa light chain (CDR 1, 2, and 3 bold type) | EIVLTQSPATLSLSPGERATLS CRASQSVSSYLAWYQQKPGQAP RLLIYDASNRATGIPARFSGSG SGTDFTLTISSLEPEDFAVYYC QQRTNWPLTFGGGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC |
| 3 | Anti-murine CD25 muIgG1 D265A X at position 115 is para-azido-phenylalanine (pAF) | QVKLLQSGAALVKPGASVKMSC KASGYSFPDSWVTWVKQSHGKS LEWIGDIFPNSGATNFNEKFKG KATLTVDKSTSTAYMELSRLTS EDSAIYYCTRLDYGYWGQGVMV TVSSXKTTPPSVYPLAPGSAAQ TNSMVTLGCLVKGYFPEPVTVT WNSGSLSSGVHTFPAVLQSDLY TLSSSVTVPSSTWPSETVTCNV AHPASSTKVDKKIVPRDCGCKP CICTVPEVSSVFIFPPKPKDVL TITLTPKVTCVVVAISKDDPEV QFSWFVDDVEVHTAQTQPREEQ FNSTFRSVSELPIMHQDWLNGK EFKCRVNSAAFPAPIEKTISKT KGRPKAPQVYTIPPPKEQMAKD KVSLTCMITDFFPEDITVEWQW NGQPAENYKNTQPIMDTDGSYF VYSKLNVQKSNWEAGNTFTCSV LHEGLHNHHTEKSLSHSPGK |
| 4 | Anti-murine CD25 muKappa | DVVLTQTPPTLSATIGQSVSIS CRSSQSLLHSNGNTYLNWLLQR PGQPPQLLIYLASRLESGVPNR FSGSGSGTDFTLKISGVEAEDL GVYYCVQSSHFPNTFGVGTKLE LKRADAAPTVSIFPPSSEQLTS GGASVVCFLNNFYPKDINVKWK IDGSERQNGVLNSWTDQDSKDS TYSMSSTLTLTKDEYERHNSYT CEATHKTSTSPIVKSFNRNEC |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A compound comprising the formula

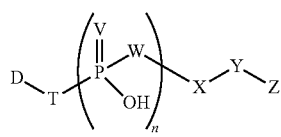

wherein

V is selected from O and S;

W is selected from O, N, and CH$_2$;

X is selected from a covalent bond; a carbon atom; a heteroatom; an optionally substituted group selected from the group consisting of acyl, aliphatic, heteroaliphatic, aryl, heteroaryl, and heterocyclic; a carbon atom linked to a trimethylammonium group by a C1-C5 hydrocarbon chain; nucleoside, protease sensitive group, cathepsin B sensitive group, or glycosidase sensitive group;

Y is selected from a covalent bond or a bivalent, straight or branched, saturated or unsaturated, optionally substituted C1-30 hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group;

T is an NR, O, or S;

Z is a cyclooctyne;

D is an anti-inflammatory agent;

Each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

2. The compound of claim 1, wherein the anti-inflammatory agent is a glucocorticoid receptor agonist.

3. The compound of claim 1, wherein the anti-inflammatory agent is Cortisol, cortisone acetate, beclometasone, prednisone, prednisolone, methylprednisolone, betamethasone, trimcinolone, budesonide, dexamethasone, fluticasone, fluticasone propionate, fluticasone furoate, compound 15-5, or mometasone.

4. The compound of claim 1, wherein the compound has a structure selected from the group consisting of

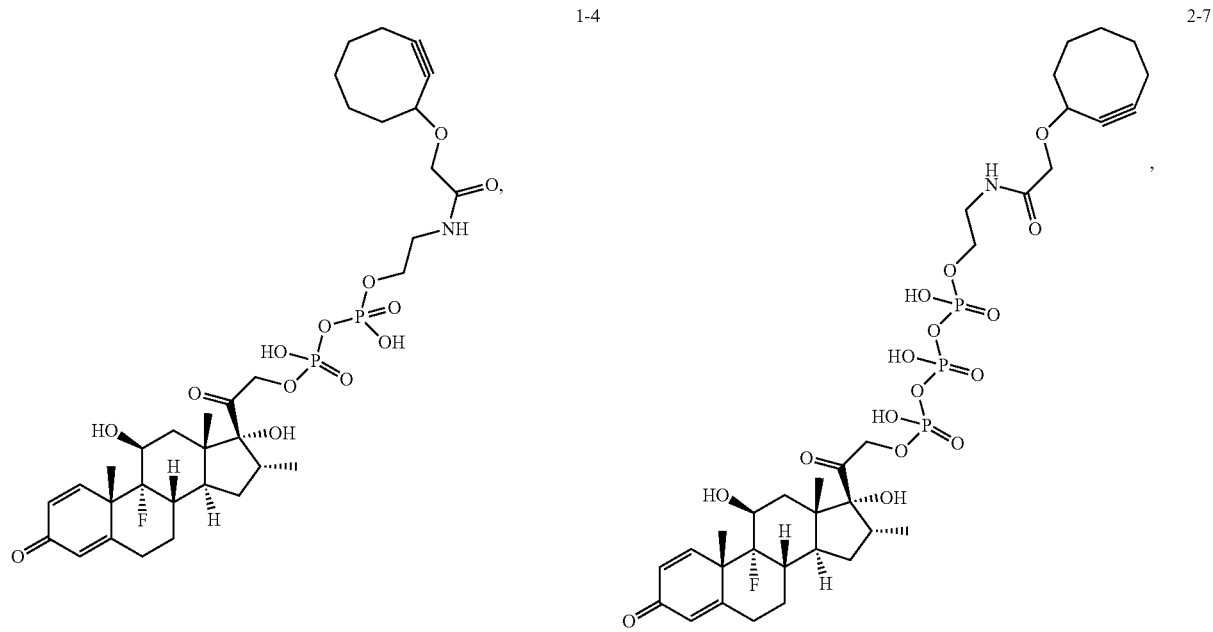

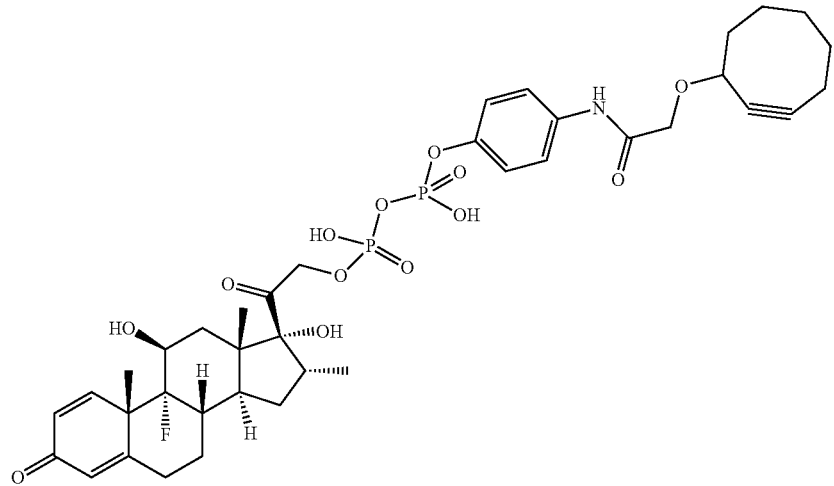
3-4
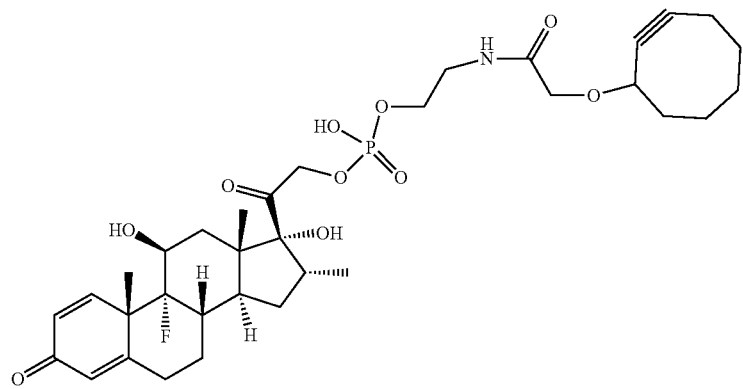
4-3
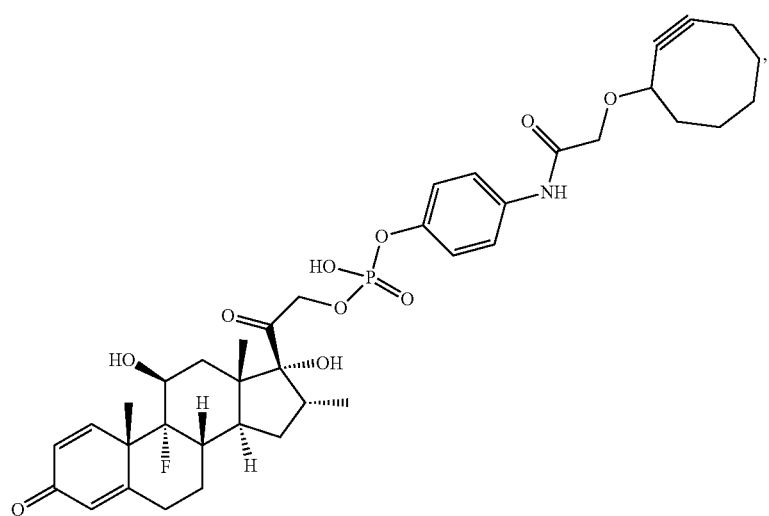
5-3

-continued
6-2
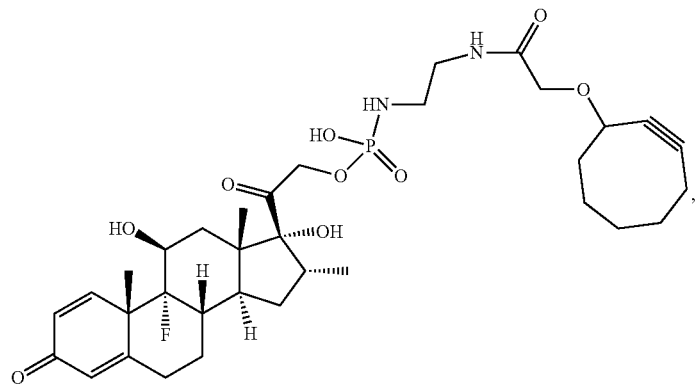
8-5
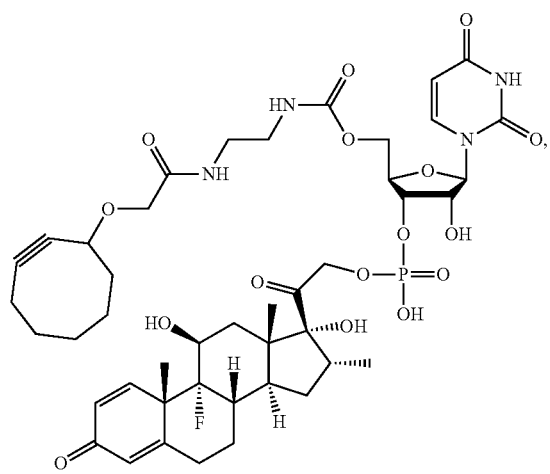
9-4
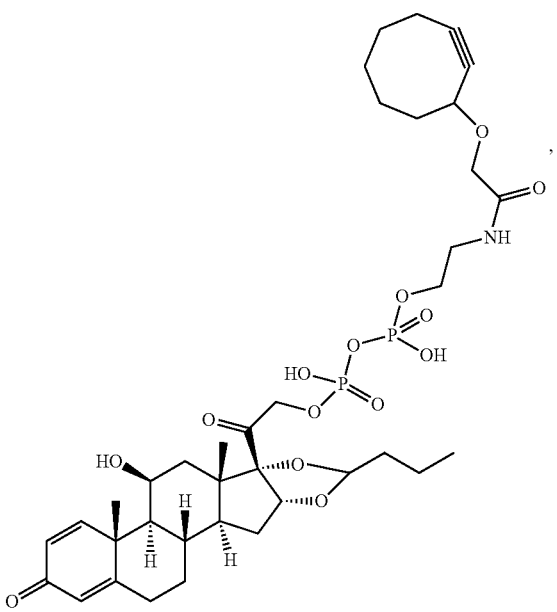
11-5
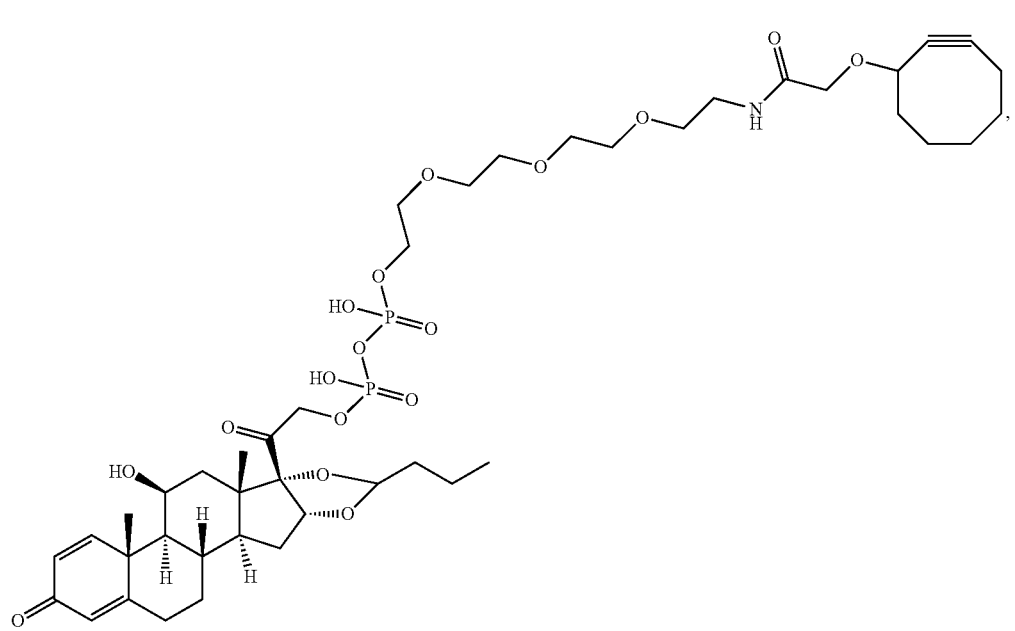

12-3
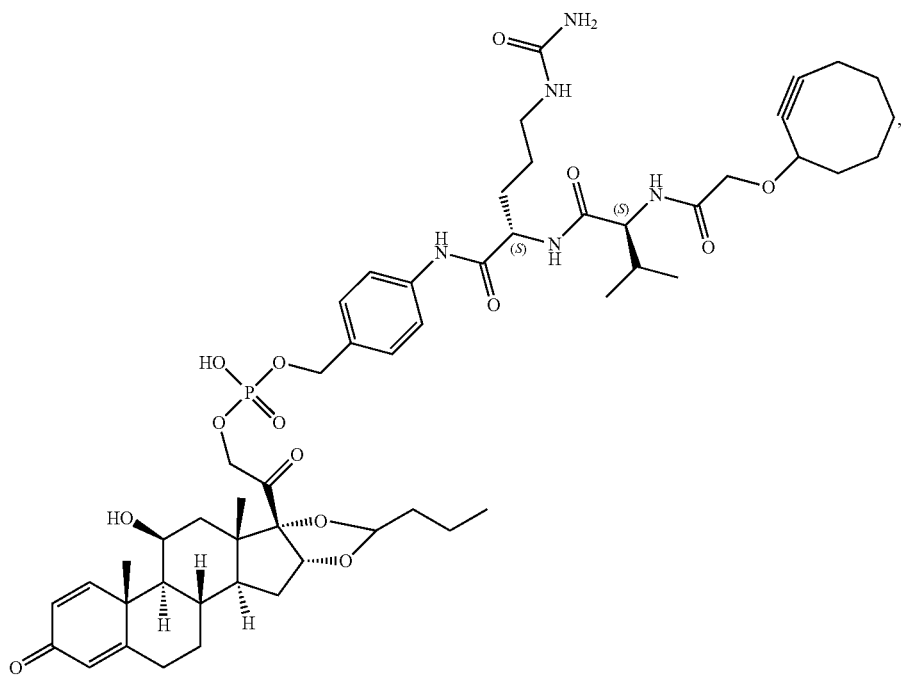
13-7
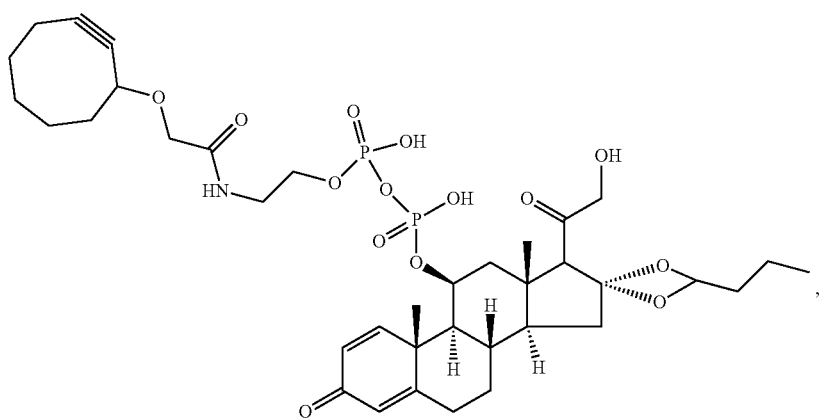
14-5
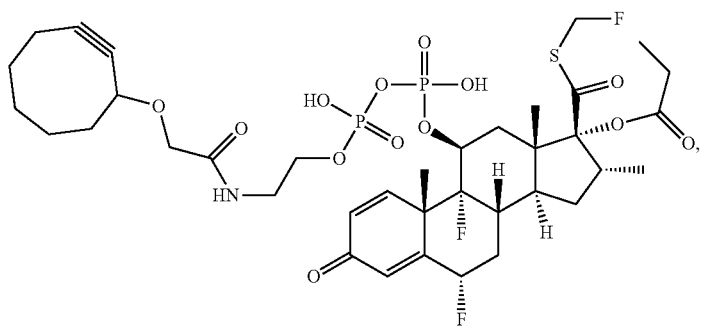

15-5
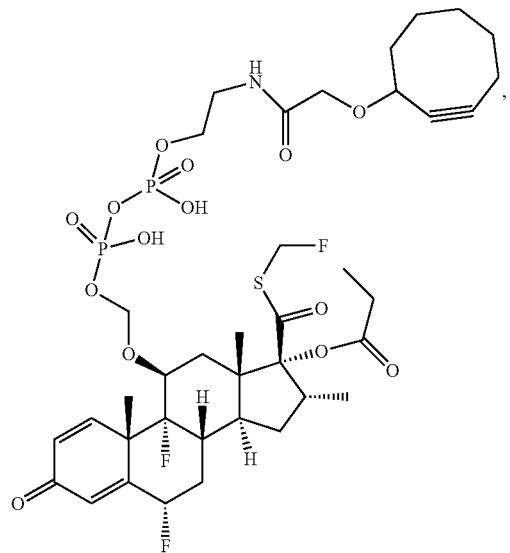
16-5
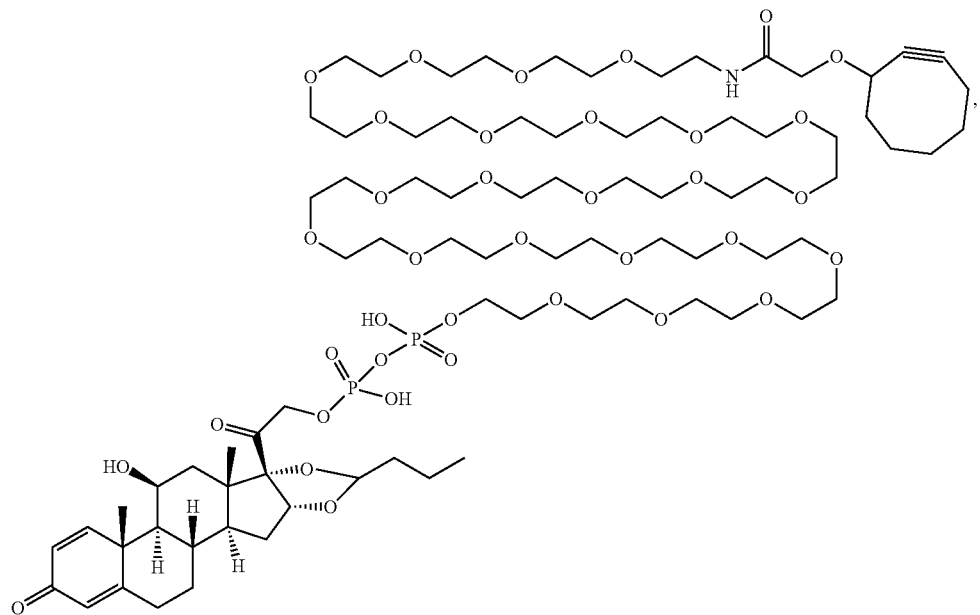
17-2
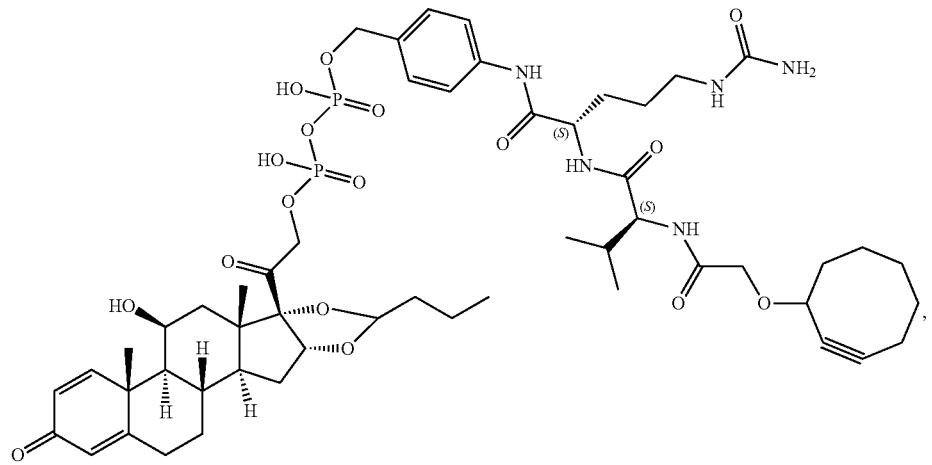

-continued
18-3
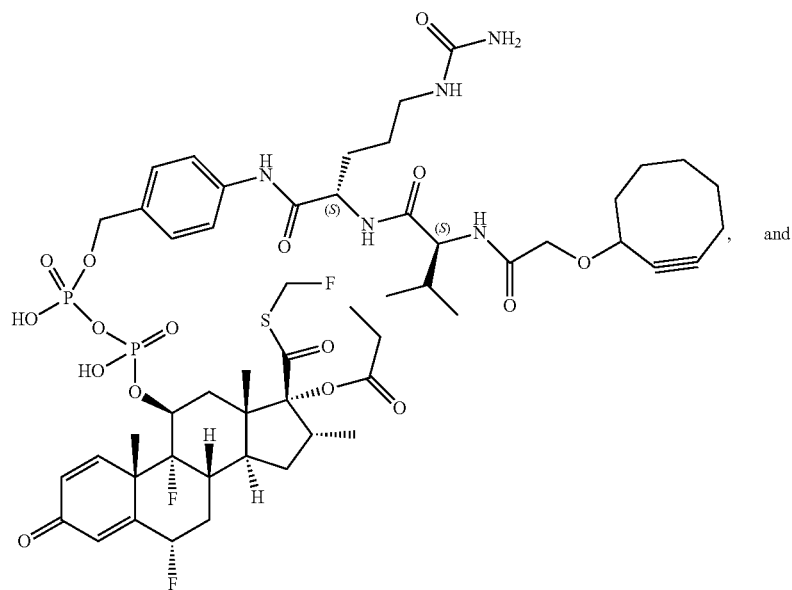
19-5
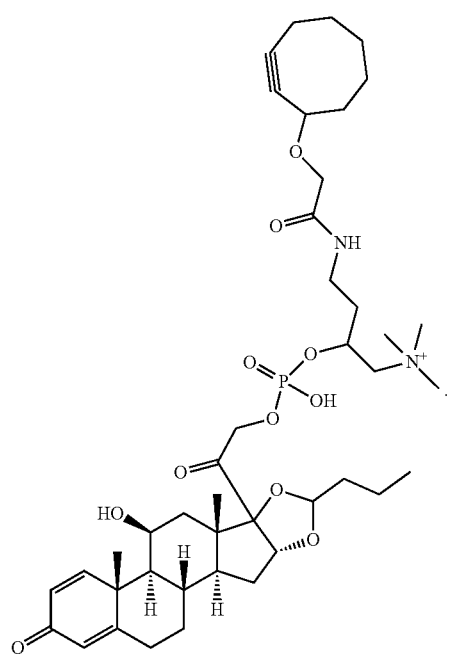
* * * * *